United States Patent [19]

Dutta

[11] Patent Number: 6,034,056
[45] Date of Patent: Mar. 7, 2000

[54] FIBRONECTIN ADHESION INHIBITORS

[75] Inventor: Anand Swaroop Dutta, Macclesfield, United Kingdom

[73] Assignee: Zeneca Limited, London, United Kingdom

[21] Appl. No.: 08/860,248

[22] PCT Filed: Dec. 21, 1995

[86] PCT No.: PCT/GB95/02992

§ 371 Date: Jun. 24, 1997

§ 102(e) Date: Jun. 24, 1997

[87] PCT Pub. No.: WO96/20216

PCT Pub. Date: Jul. 4, 1996

[30] Foreign Application Priority Data

Dec. 24, 1994 [GB] United Kingdom ............ 9426254
Mar. 24, 1995 [GB] United Kingdom ............ 9505905
Jul. 7, 1995 [GB] United Kingdom ............ 9513904

[51] Int. Cl.$^7$ .................... A61K 38/12; C07K 7/64
[52] U.S. Cl. ................ 514/9; 514/10; 514/11; 530/317
[58] Field of Search ................ 530/317; 514/9, 514/11

[56] References Cited

FOREIGN PATENT DOCUMENTS

| 0 341 915 | 11/1989 | European Pat. Off. . |
| 0 422 938 | 4/1991 | European Pat. Off. . |
| WO92/00995 | 1/1992 | WIPO . |
| 94 02445 | 2/1994 | WIPO . |
| 94 15958 | 7/1994 | WIPO . |
| 9415958 | 7/1994 | WIPO . |
| 96 14714 | 6/1995 | WIPO . |
| 96 00581 | 1/1996 | WIPO . |
| 96 06108 | 2/1996 | WIPO . |

OTHER PUBLICATIONS

Wayner: "Activation–dependent recognition by hematopoietic cells of the LDV sequence in the V region of fibronectin", Journal of Cell Biology, vol. 116, No. 2, 1992, pp. 489–497, cited in the application, see the whole document.

KISO: "Synthesis of ANP fragments with hypertensive action", Chemical Abstracts, vol. 110, No. 3, Jan. 16, 1989; abstract No. 24283k, pp. 592, col. 1; see abstract & PEP-T.CHEM.,–1987 pp. 512–516.

B. Weinstein "Chemistry and Biochemistry of Amino Acids, Peptides and Proteins", 1983, See pp. 338–pp. 4 241.

Aumailley et al., "Arg–Gly=Asp constrained within cyclic pentapeptides—Strong and selective ingibitors of cell adhesion of vitronectin and laminin fragment P1", Federation of European Biochemical Societies, Oct., 1991, pp. 50–54.

Lublin, "Susceptibility to experimental allergic encephaomyelitis in animal models of autoimmunity", Neurology and Neurosurgery, 1992, vol. 5, pp. 182–187.

Bowen et al., "Disease–Modifying Anti–Rheumatic Drugs: Strategies for Screening", Pharmac. Ther. 1992, vol. 56, pp. 287–306.

*Primary Examiner*—Cecilia J. Tsang
*Attorney, Agent, or Firm*—Phillsbury Madison & Sutro, LLP; Intellectual Property Group

[57] ABSTRACT

Cyclic peptides of formula (1):

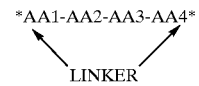

Wherein: AA1 is an L or D amino acid selected from Ile and Leu or amino acid analogue thereof; AA2 is an L amino acid selected from Leu or amino acids analogue thereof; AA3 is an L amino acid selected from Asp or amino acid analogue thereof containing a carboxy group in its side chain; AA4 is an L amino acid selected from Val or amino acid analogue thereof and; LINKER represents a linking moiety for linking N terminus of AA1 to C terminus of AA4 to form a cyclic peptide containing a heterocyclic ring having 17 to 30 members. The cyclic peptides inhibit the interaction of vascular cell adhesion molecule-1 and fibronectin with integrin very late antigen 4 and have therapeutic applications such as in rheumatoid arthritis or multiple sclerosis.

12 Claims, 22 Drawing Sheets

FIG. 1
Formula 1
Formula 2
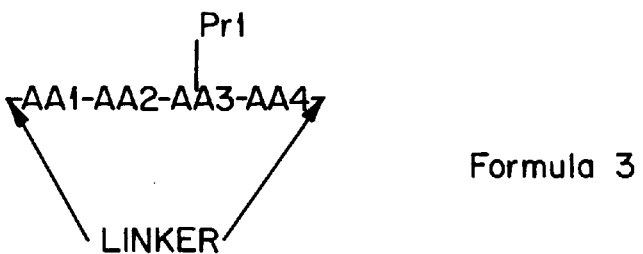
Formula 3
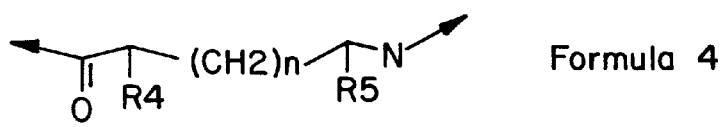
Formula 4
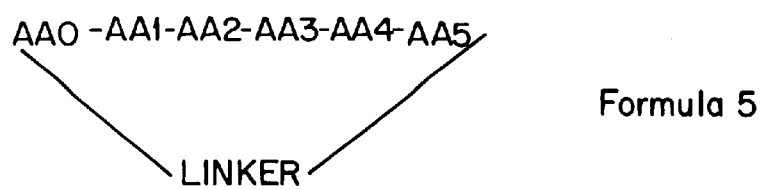
Formula 5

FIG. 2A
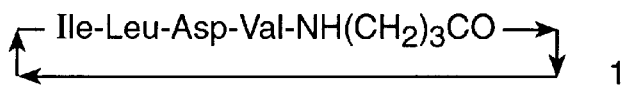
1
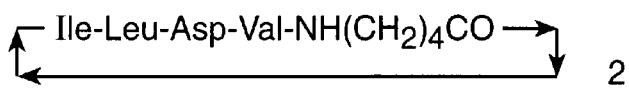
2
c(Ile-Leu-Asp-Val-NH-(CH$_2$)$_5$-CO-)   3
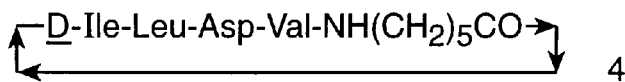
4
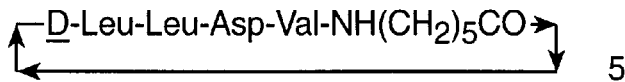
5
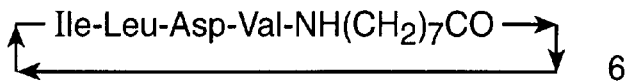
6
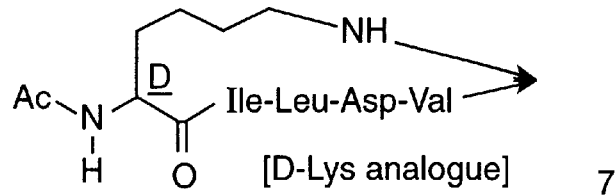
[D-Lys analogue]   7
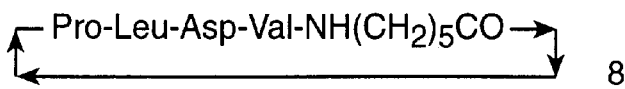
8
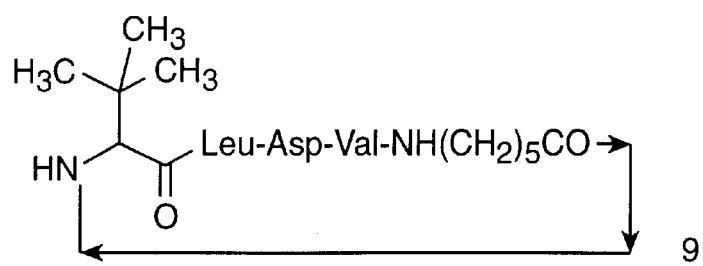
9

FIG. 2B
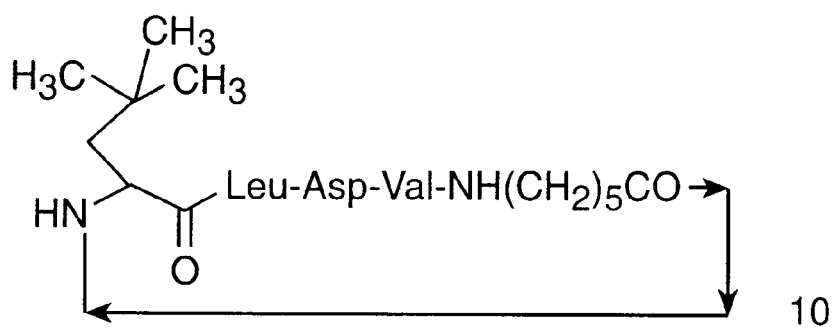
10
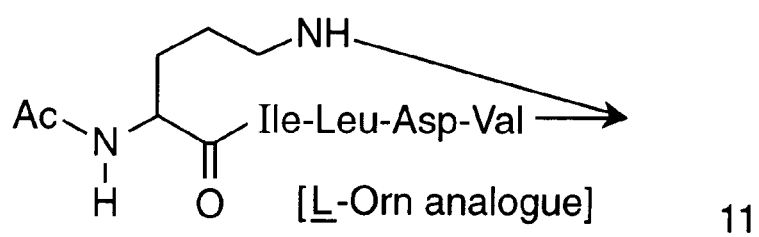
[L-Orn analogue] 11
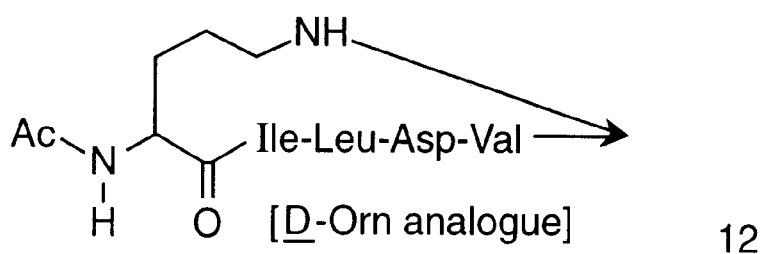
[D-Orn analogue] 12
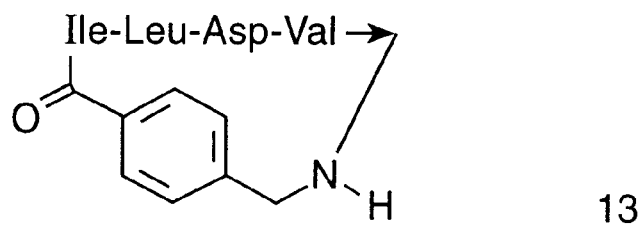
13
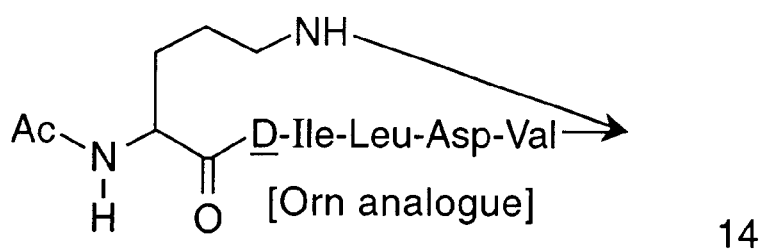
[Orn analogue] 14

FIG. 3

Step 1.

Fmoc–NH-(CH$_2$)$_5$-COO-Chlorotritylresin

↓

Step 2.

Fmoc-Ile-Leu-Asp(OBut)-Val–NH-(CH$_2$)$_5$-COO-Chlorotritylresin

↓ Piperidine

Step 3.

Ile-Leu-Asp(OBut)-Val–NH-(CH$_2$)$_5$-COO-Chlorotritylresin

↓ Acetic acid/Trifluoroethanol/Dichloromethane

Step 4.

Ile-Leu-Asp(OBut)-Val–NH-(CH$_2$)$_5$-COOH

↓ Cyclisation

Step 5.

c(Ile-Leu-Asp(OBut)-Val–NH-(CH$_2$)$_5$-CO)

↓ Trifluoroacetic acid/water/triisopropylsilane

Step 6.

c(Ile-Leu-Asp-Val–NH-(CH$_2$)$_5$-CO)

FIG. 4
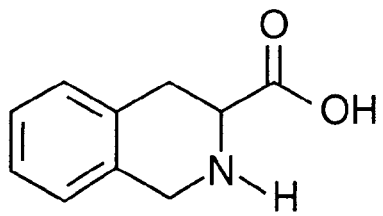
1,2,3,4-Tetrahydroisoquinoline-3-carboxylic acid
(Tic)
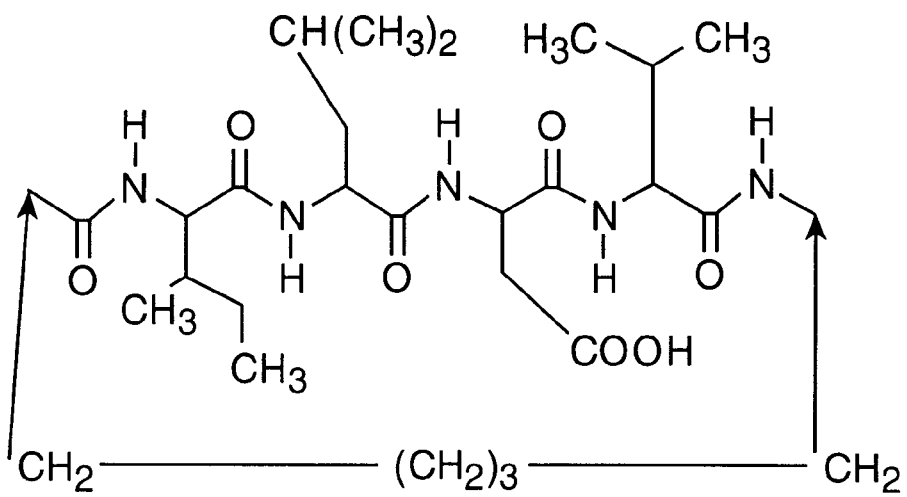
c(NH-(CH$_2$)$_5$-CO-Ile-Leu-Asp-Val)
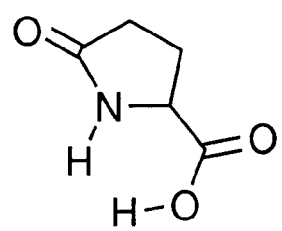
Pyr

FIG. 5
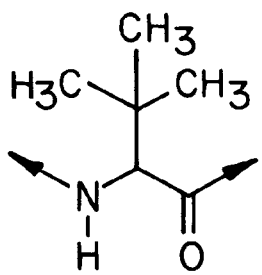
[t-butyl-glycine, t-leucine]
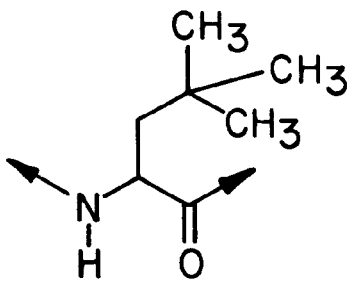
[t-butyl-alanine, neopentylglycine]
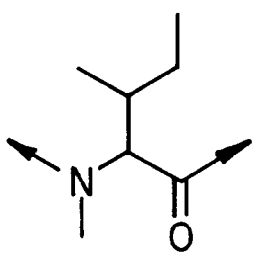
N-Me-Ile

FIG. 6
Step 1.
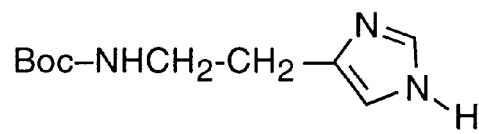
Step 2.
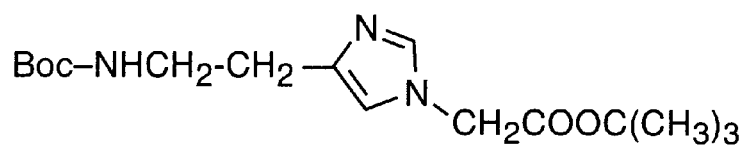
Step 3.
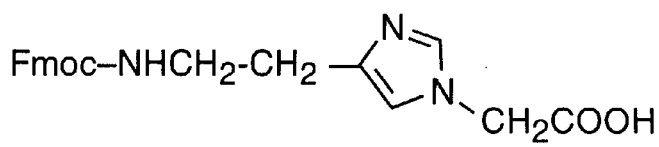
Step 4.
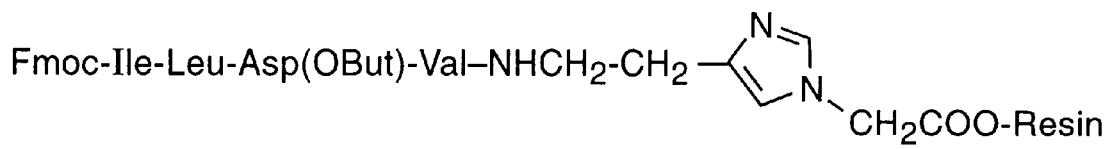
Step 5.
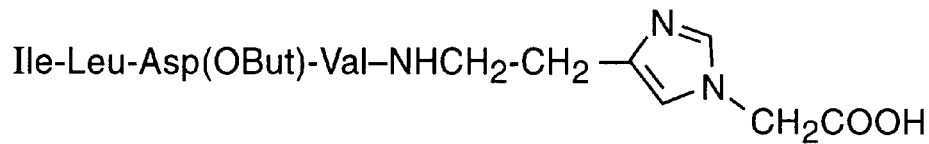
Step 6.
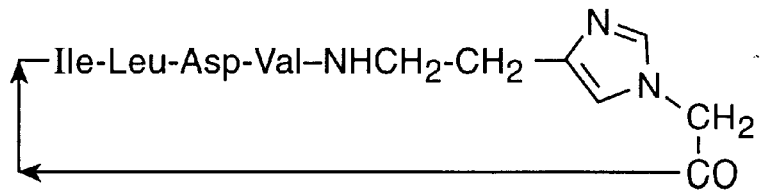

FIG. 8
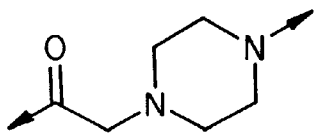
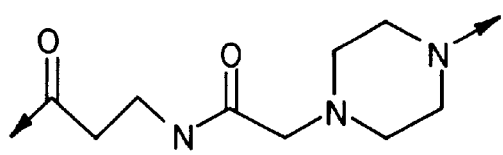
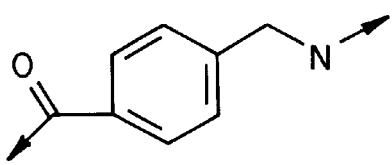
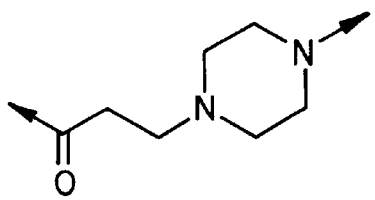
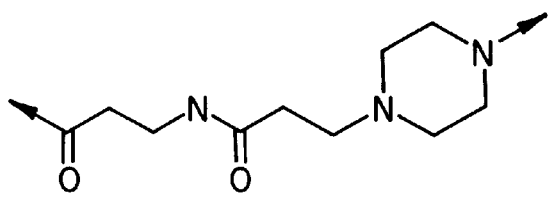
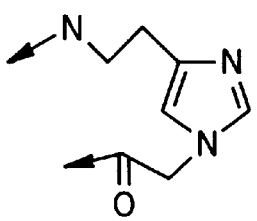

FIG. 9
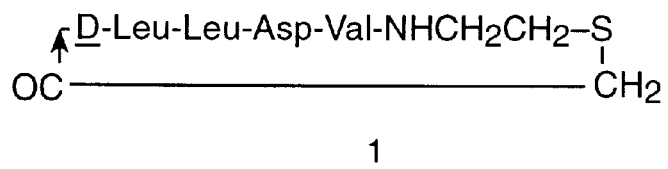
1
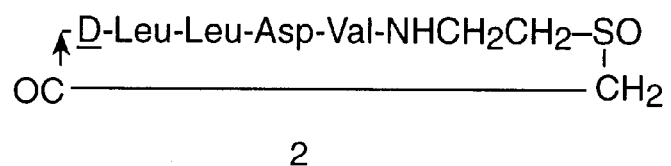
2
FIG. 10
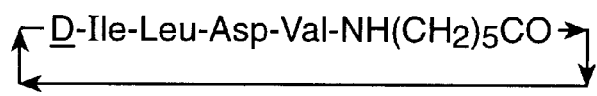
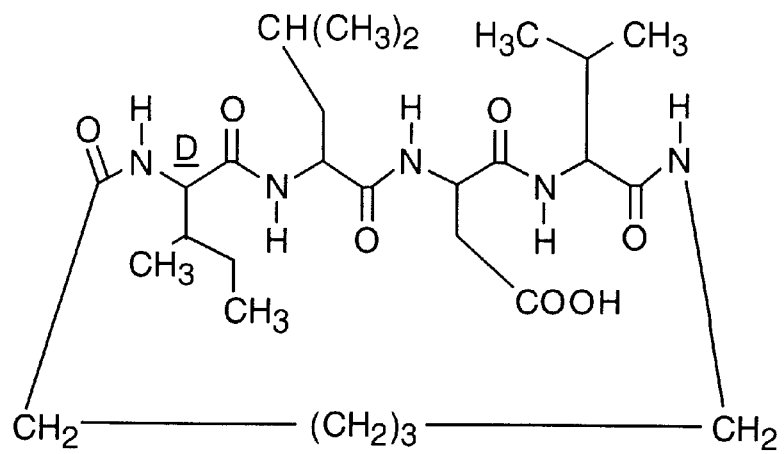

FIG. 11
Step 1.
Z-D-Lys(Fmoc)-Ile-Leu-Asp(OBut)–Val-Chlorotritylresin
↓ Piperidine
Step 2.
Z-D-Lys-Ile-Leu-Asp(OBut)–Val-Chlorotritylresin
↓ Acetic acid/Trifluoroethanol/Dichloromethane
Step 3.
Z-D-Lys-Ile-Leu-Asp(OBut)–Val
↓ Cyclisation
Step 4.
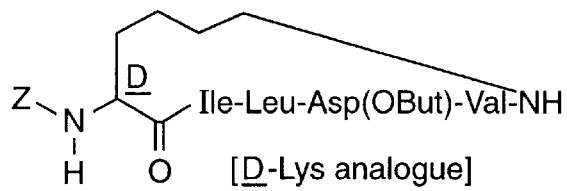
[D-Lys analogue]
↓ 1. H₂, Pd/C
  2. Acetic Anhydride
Step 5.
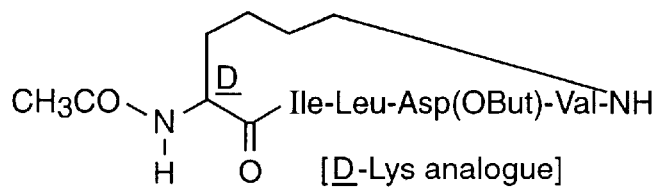
[D-Lys analogue]
↓ Trifluoroacetic acid - Water - Triisopropylsilane
Step 6.
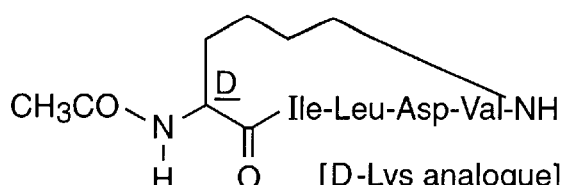
[D-Lys analogue]

FIG. 12
Step 1.
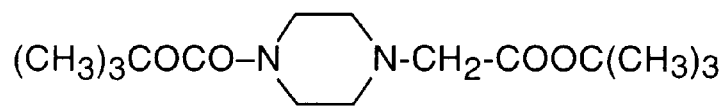
Step 2.
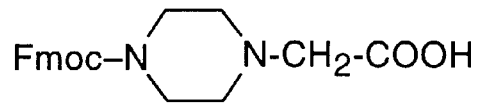
Step 3.
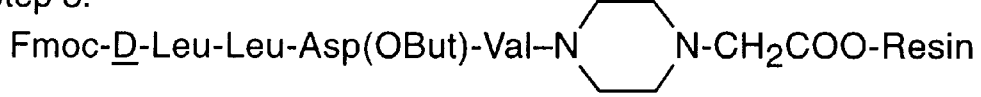
Step 4.
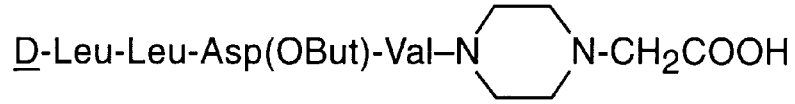
Step 5.
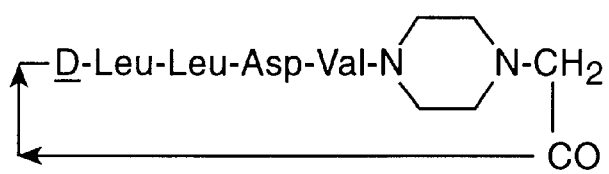

6 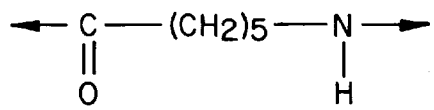
7 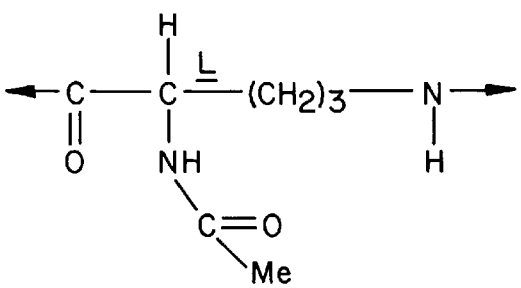
8 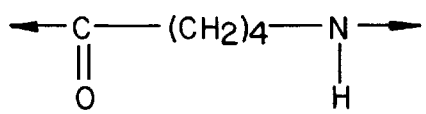
9 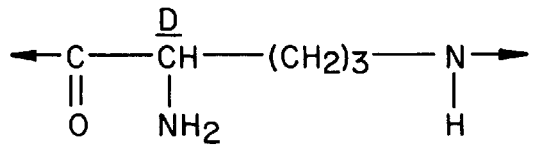
10 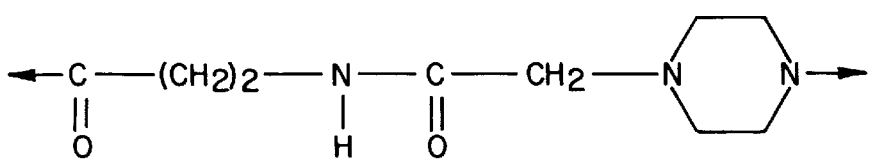
11 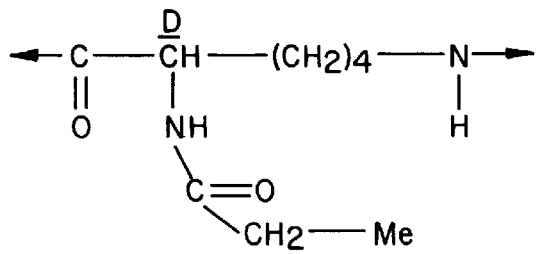
12 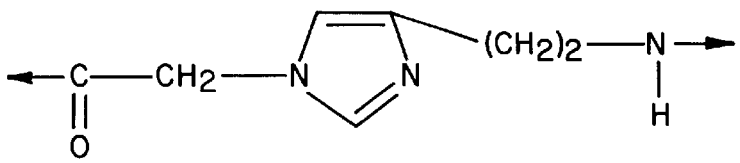
13 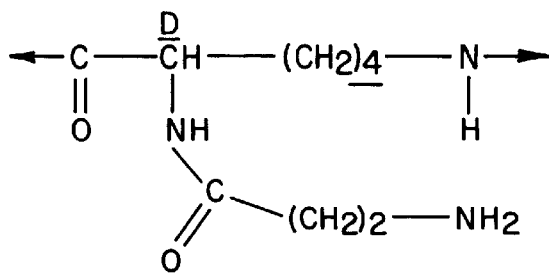
FIG. 13A

FIG. 13B
14 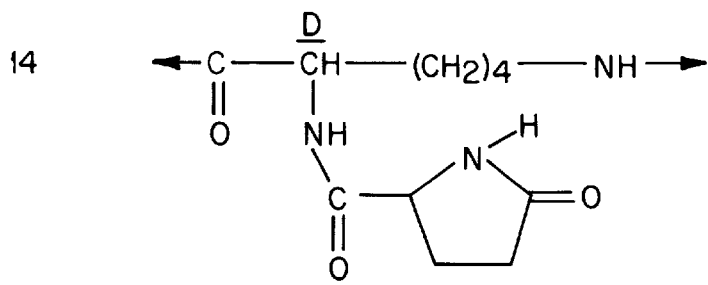
15 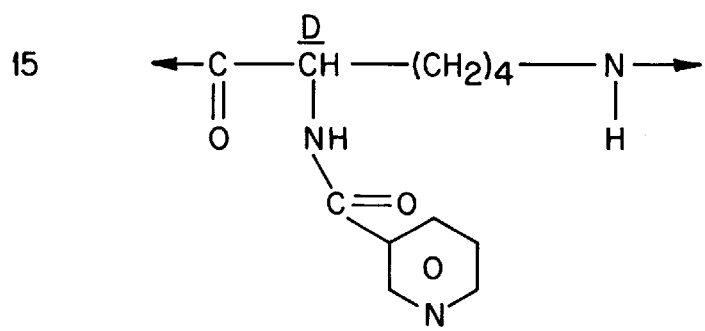
16 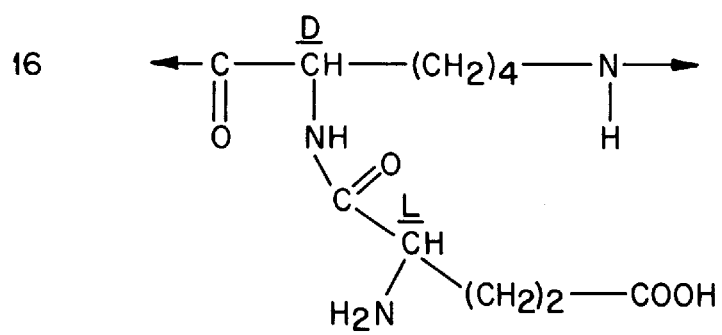
17 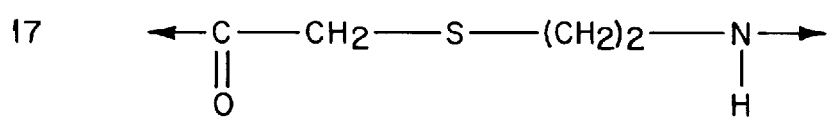
18 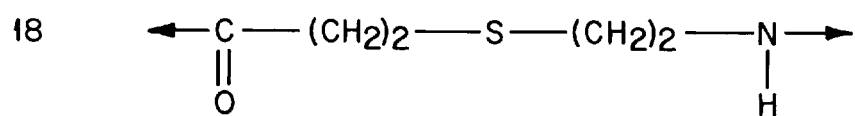

FIG. 13C
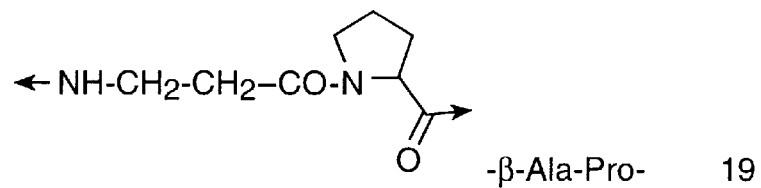
-β-Ala-Pro-    19
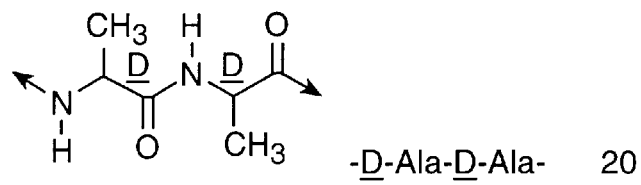
-D-Ala-D-Ala-    20
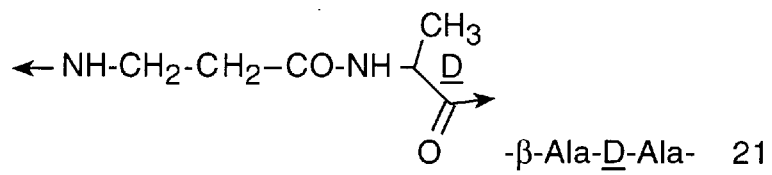
-β-Ala-D-Ala-    21
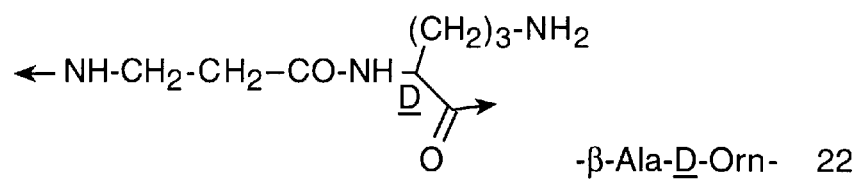
-β-Ala-D-Orn-    22
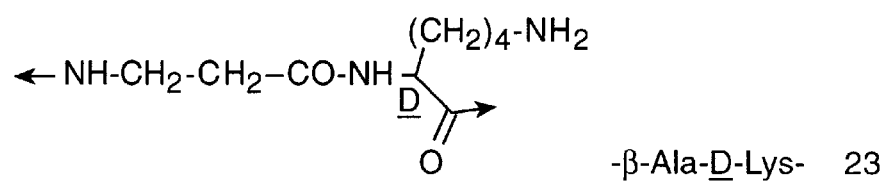
-β-Ala-D-Lys-    23
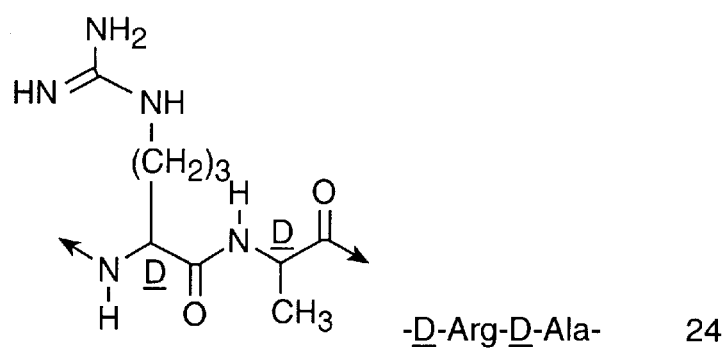
-D-Arg-D-Ala-    24

FIG. 13D
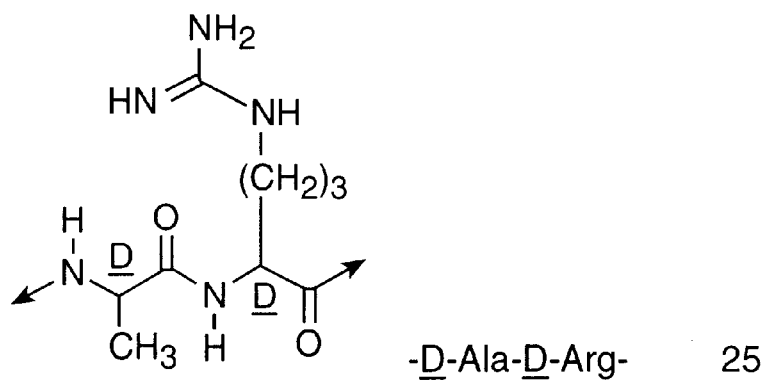
-D-Ala-D-Arg-    25
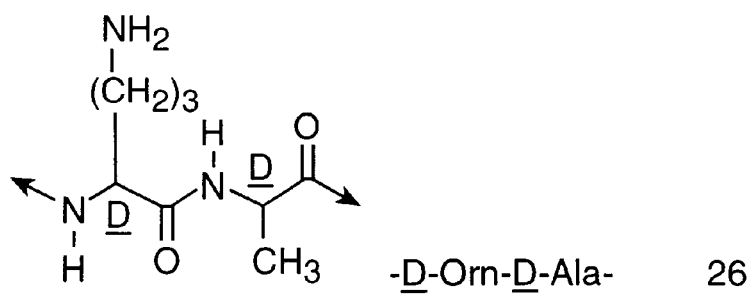
-D-Orn-D-Ala-    26
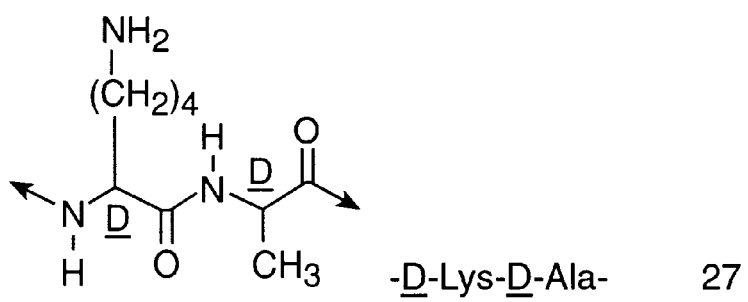
-D-Lys-D-Ala-    27
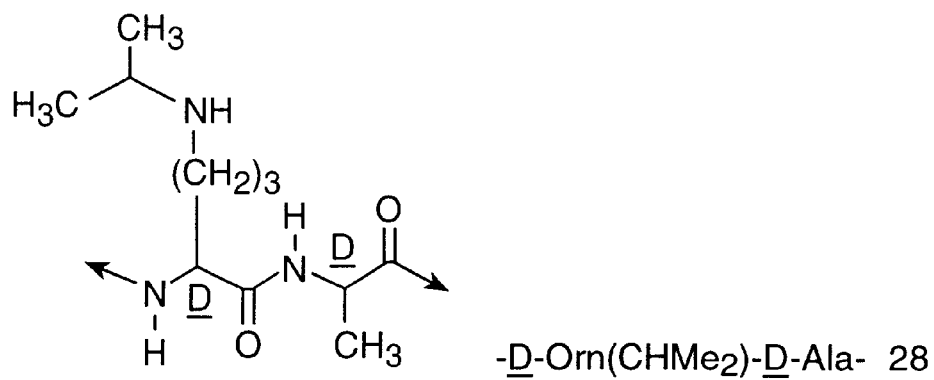
-D-Orn(CHMe₂)-D-Ala-  28

FIG. 13E
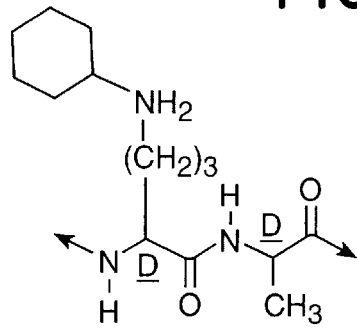
-D-Orn(cyclohexyl)-D-Ala-  29
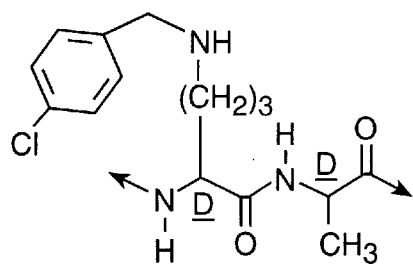
-D-Orn(4-chlorobenzyl)-D-Ala-  30
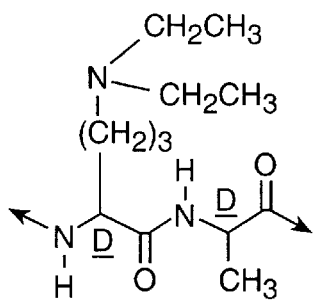
-D-Orn(Et2)-D-Ala-  31
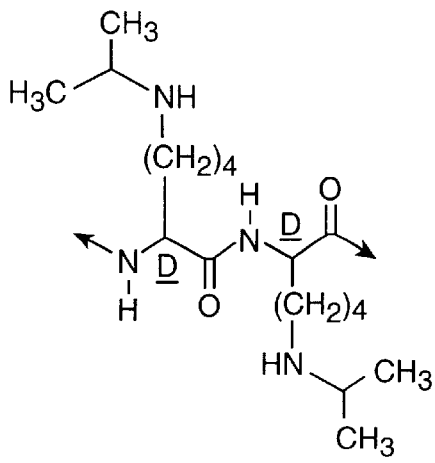
-D-Lys(CHMe2)-D-Lys(CHMe2)-  32

FIG. 13F
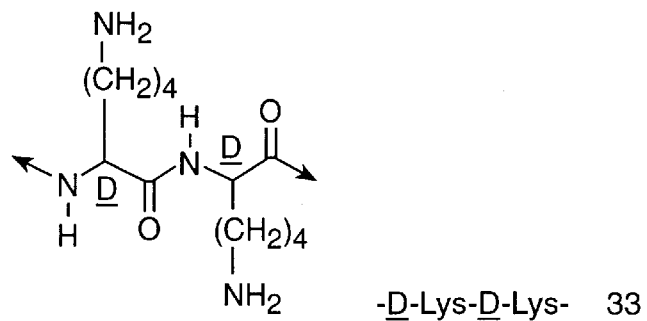
-D-Lys-D-Lys-  33
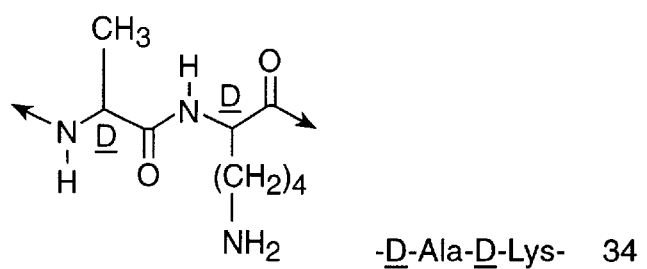
-D-Ala-D-Lys-  34
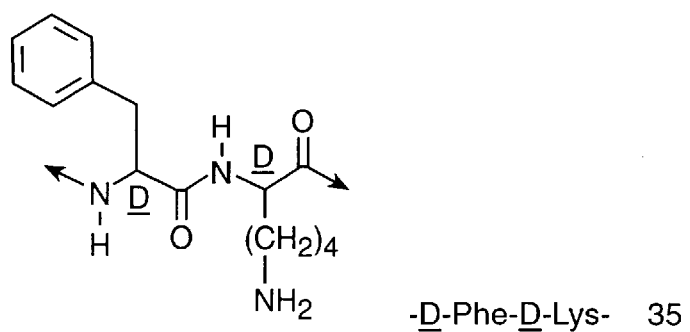
-D-Phe-D-Lys-  35
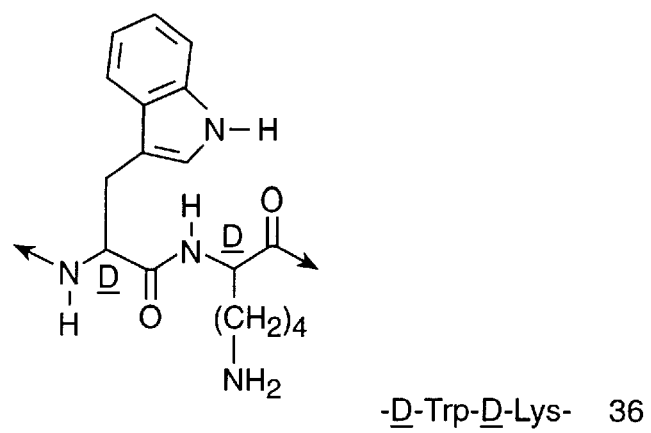
-D-Trp-D-Lys-  36

FIG. 13G
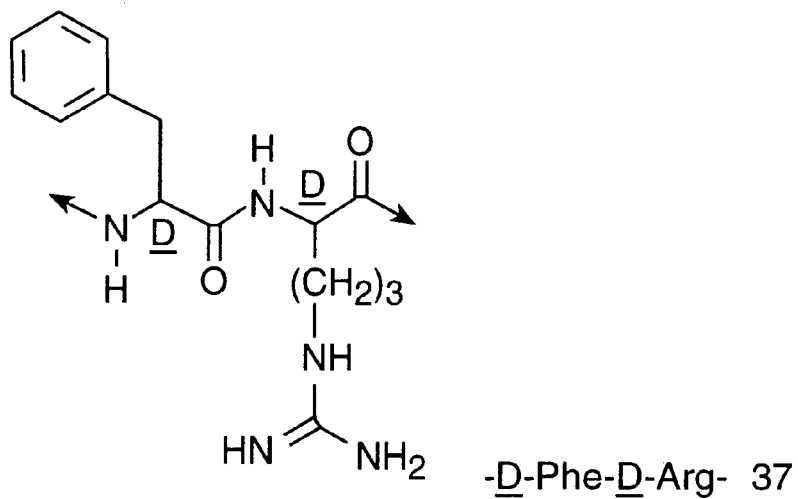
-D-Phe-D-Arg- 37
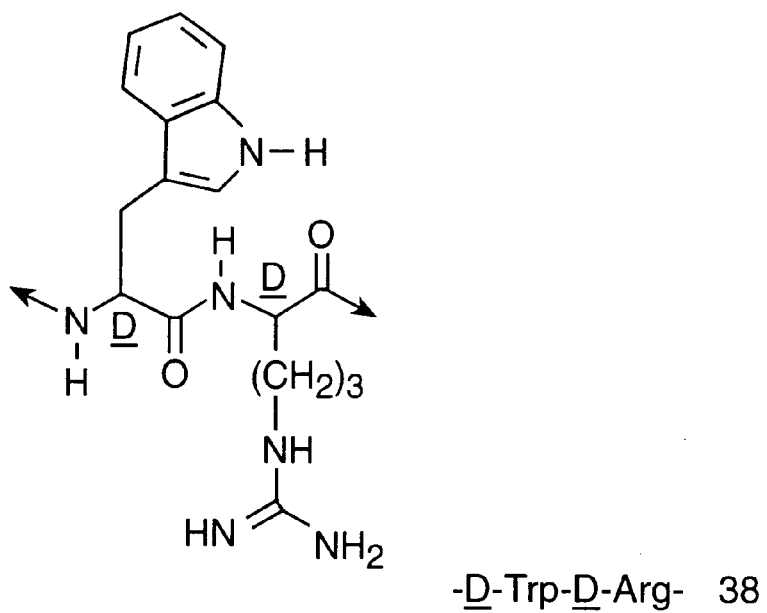
-D-Trp-D-Arg- 38
-D-Arg(Pmc)-D-Ala- 39
-D-Ala-D-Arg(Pmc)- 40
-D-Phe-D-Arg(Pmc)- 41
-D-Trp-D-Arg(Pmc)- 42

FIG. 13H
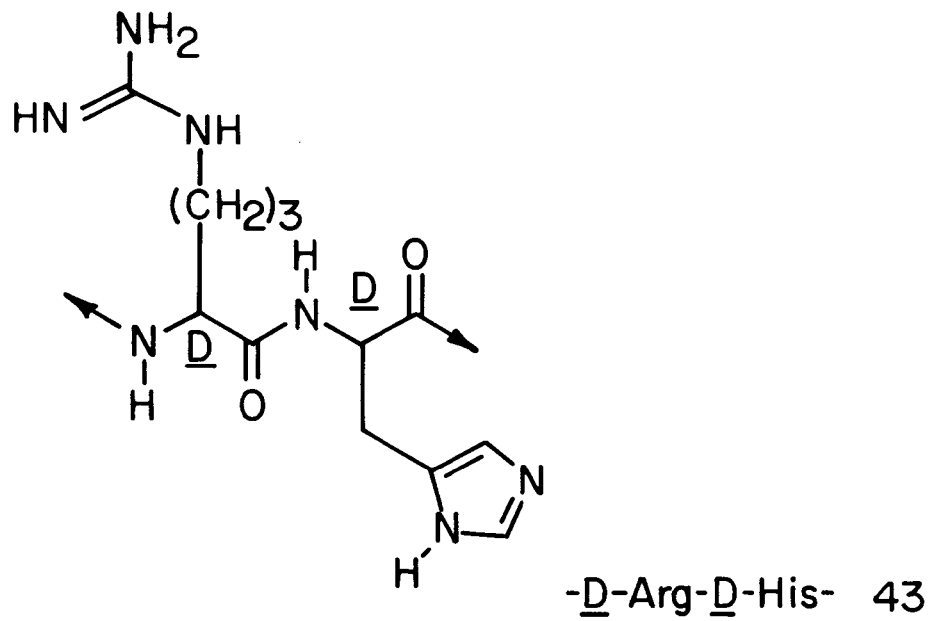
-D-Arg-D-His-  43
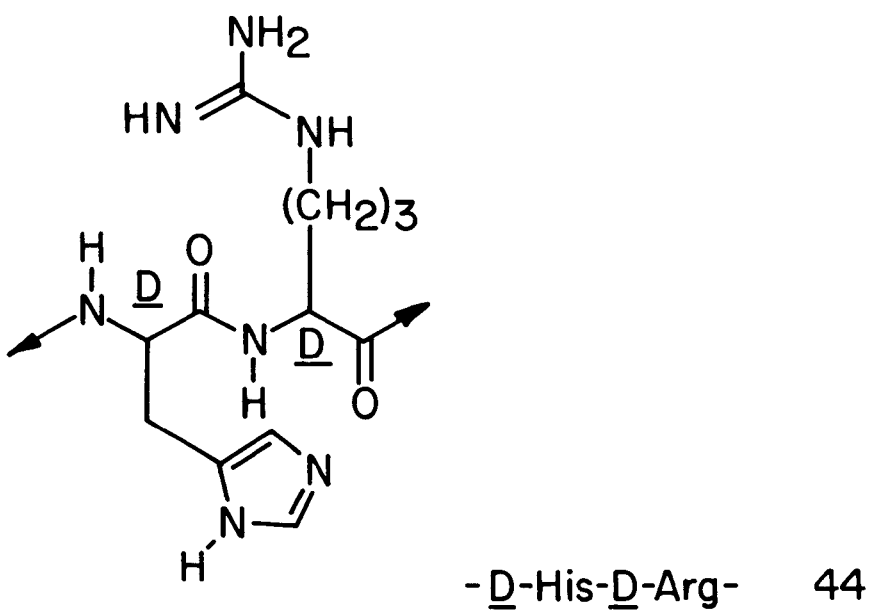
-D-His-D-Arg-  44

FIG. 14
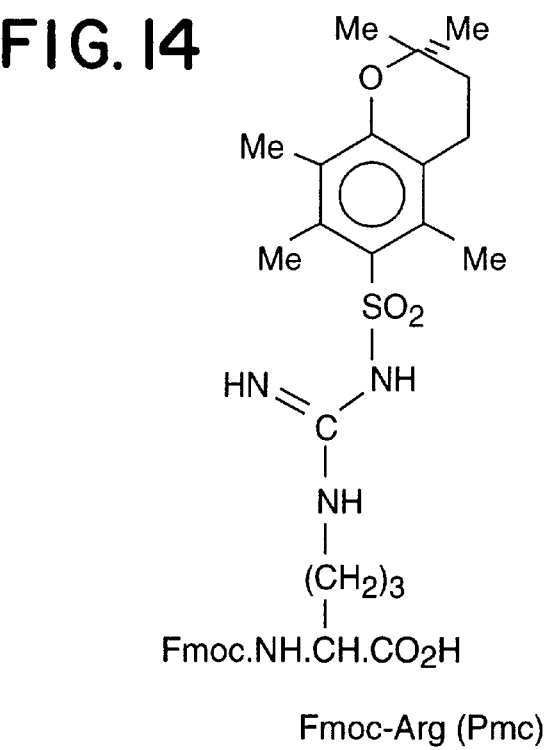
Fmoc-Arg (Pmc)
FIG. 15
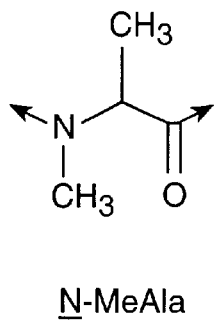
N-MeAla
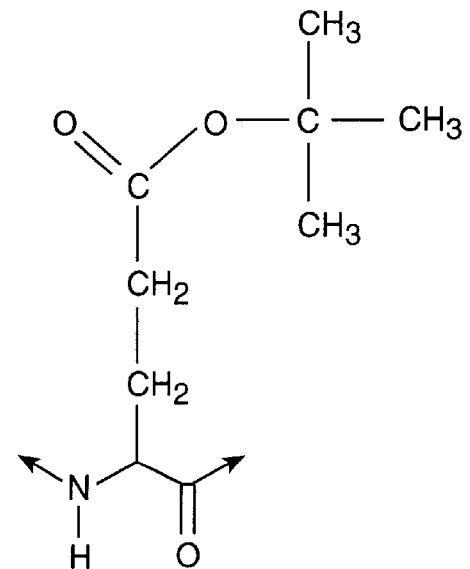
Asp (OBu$^t$)

FIG. 16
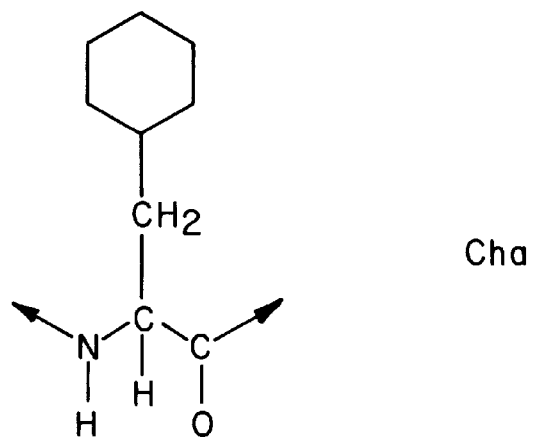
Cha
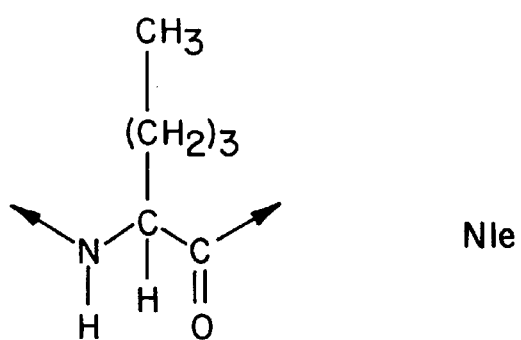
Nle
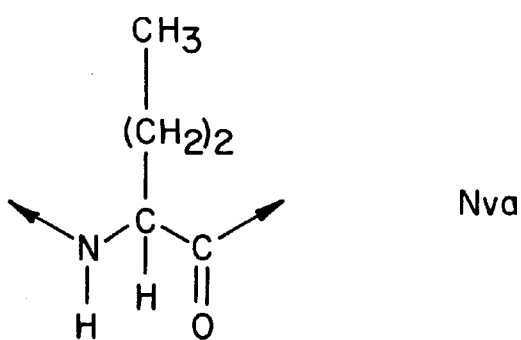
Nva

FIBRONECTIN ADHESION INHIBITORS

This application is the national phase of international application PCT/GB95/02992, filed Dec. 21, 1995 which was designated the U.S.

Many of the cell-cell and cell-extracellular matrix interactions are mediated by protein ligands (e.g. fibronectin, vitronectin and VCAM-1) and their integrin receptors [e.g. VLA-4 (α4β1]. Recent studies have shown these interactions to play an important role in many physiological (e.g. embryonic development and wound healing) and pathological (e.g. tumour-cell invasion and metastasis, inflammation, atherosclerosis and autoimmune diseases) conditions. Agents which can selectively inhibit some of these interactions are predictably useful for the treatment of a number of diseases.

Integrins are heterodimeric cell surface receptors that are composed of noncovalently associated α and β subunits. Using molecular biology and protein chemistry, a number of α and β subunits have been identified. The integrin family can be subdivided into classes based on the β subunits, which can be associated with one or more α subunits. The most widely distributed integrins belong to the β1 class, also known as the very late antigens (VLA). The second class of integrins are leukocyte-specific receptors and consist of one of three α subunits (αL, αM, or αX) complexed with the β2 protein. The cytoadhesins αIIbβ3 and αvβ3, constitute the third class of integrins.

A wide variety of proteins serve as ligands for integrin receptors. In general, the proteins recognised by integrins fall into one of three classes: extracellular matrix proteins, plasma proteins, and cell surface molecules. Extracellular matrix proteins such as collagen, fibronectin, fibrinogen, laminin, thrombospondin, and vitronectin bind to a number of integrins. Many of these adhesive proteins also circulate in plasma and bind to activated blood cells. Additional components in plasma that are ligands for integrins include fibrinogen and factor X. Cell-bound complement C3bi and several transmembrane proteins, such as Ig-like cell adhesion molecule (ICAM-1,2,3) and vascular cell adhesion molecule (VCAM-1), which are members of the Ig superfamily, also serve as cell-surface ligands for some integrins.

The target amino acid sequences for many integrins have been identified. For example, the target sequence in α5β1, αIIβ3, and αvβ3, is the Arg-Gly-Asp tripeptide found in proteins such as fibronectin, fibrinogen, thrombospondin, type 1 collagen, vitronectin and vWF. However, the Arg-Gly-Asp sequence is not the only integrin recognition motif used by adhesive ligands. Another integrin α4β1 binds the variable region (CS1) of fibronectin via the sequence Leu-Asp-Val and the platelet integrin αIIbβ3 also recognises the sequence His-His-Leu-Gly-Gly-Ala-Lys-Gln-Ala-Gly-Asp-Val at the carboxy-terminus of the gamma chain of fibrinogen.

The present invention principally relates to agents which block the interaction of the ligand VCAM-1 to its integrin receptor VLA-4 (α4β1). [Reference for a review on VLA-4: Structure of the Integrin VLA-4 and Its Cell-Cell and Cell Matrix Adhesion Functions, M. E. Hemler, M. J. Elices, C. Parker and Y. Takada, Immunological Reviews, 114 (1990) 45–65.] Integrin α4β1 is expressed on numerous hematopoietic cells and established cell lines, including hematopoietic precursors, peripheral and cytotoxic T lymphocytes, B lymphocytes, monocytes, thymocytes and eosinophils. Unlike other β1 integrins that are involved only in cellextracellular matrix interactions, α4β1 mediates both cell-cell and cell-extracellular matrix interactions. Cells expressing activated α4β1 bind to the carboxy-terminal cell binding domain of fibronectin (non Arg-Gly-Asp mediated), to VCAM-1 expressed on endothelial cells, and to each other to promote homotypic aggregation. The expression of VCAM-1 by endothelial cells is upregulated by proinflammatory cytokines such as INF-γ, TNF-α and IL-1β.

Regulation of α4β1-mediated cell adhesion is important in numerous physiologic processes, including T-cell proliferation, B-cell localisation to germinal centres, and adhesion of activated T cells and eosinophils to endothelial cells. In addition, integrin α4β1-mediated processes are implicated in several diseases such as melanoma cell invasion in metastasis, T-cell infiltration of synovial membranes in rheumatoid artritis, autoimmune diabetes, collitis and leukocyte penetration of the blood-brain barrier in experimental autoimmune encephalomyelitis, atherosclerosis, peripheral vascular disease, cardiovascular disease and multiple sclerosis. Evidence for the involvement of VLA-4/VCAM-1 interaction in the above disease processes has been accumulated by investigating the role of the peptide CS-1 and antibodies specific for VLA-4 or VCAM-1 in various in vitro and in vivo experimental models of inflammation (e.g. contact cutaneous hypersensitivity response in mice), experimental autoimmune encephalomyelitis, lung antigen challenge, diabetes, ulcerative colitis, nephritis and allograft rejection. Further relevant diseases include asthma, psoriasis, restenosis, myocarditis and inflammatory bowel disease.

For example, in an experimental model of arthritis (arthritis induced in inbred female Lewis rats with a single intraperitoneal injection of peptidoglycan-polysaccharide fragments from group A streptococcal cell walls), intravenous administration of CS-1 at the initiation of arthritis (days 0–4; 300 μg/day) or on days 11 to 16 in animals with established arthritis, was shown to suppress both acute and chronic inflammation. [Reference: Synthetic Fibronectin Peptides Suppress Arthritis in Rats by Interrupting Leukocyte Adhesion and Recruitment, S. M. Wahl, J. B. Allen, K. L. Hines, T. Imamichi, A. M. Wahl, L. T. Furcht and J. B. McCarthy, J. Clin. Invest., 94 (1994) 655–662].

In another model of inflammation (contact hypersensitivity response in oxazalone or 2,4-dinitrofluorobenzene-sensitised mice), intravenous administration of the anti-α-4 specific monoclonal antibodies R1-2 or PS/2 (4 to 6 hours prior to challenge) significantly inhibited (50–60% reduction in the ear swelling response) the efferent response. [Reference: Monoclonal Antibodies to the Integrin α-4 Subunit Inhibit the Murine Contact Hypersensitivity Response, P. L. Chisholm, C. A. Williams and R. R. Lobb, Eur. J. Immunol., 23 (1993) 682–688]. In an intestinal inflammation model (acute colitis in Cotton-top tamarin), anti-α4 integrin monoclonal antibody HP1/2 that binds VLA-4 resulted in significant attenuation of acute colitis. In contrast, two anti-E-selectin monoclonal antibodies (BB11 and EH8) slightly diminished colitis after the 10-day treatment period in Cotton-top tamarin [Reference: Attenuation of Colitis in the Cotton-top Tamarin by Anti-α 4 Integrin Monoclonal Antibody, D. K. Podolsky, R. Lobb, N. King, C. D. Benjamin, B. Pepinsky, P. Sehgal and M. deBeaumont, J. Clin. Invest., 92 (1993) 372–380].

The antibodies have also been shown to be effective in a model of autoimmune encephalomyelitis (EAE), an inflammatory condition of the central nervous system with similarities to multiple sclerosis. In both diseases, circulating leukocytes penetrate the blood-brain barrier and damage myelin, resulting in impaired nerve conduction and paralysis. EAE can be induced actively by priming an animal to CNS proteins like myelin basic protein (MBP), or adoptively by injection of activated lymphocytes that are specific for these CNS antigens. Various monoclonal antibodies, [MK/1 (anti-VCAM-1) and PS/12 and LPAM-1 (anti α4 integrin), when injected into irradiated female (PL/JxSJL)F1 mice delayed the onset of disease. When injection of antibody to α4 integrin (LPAM-1 and PS/2) was continued every 3 day until after onset of disease, not only was the onset of disease delayed, but in this case severity of disease was also significantly decreased. [Reference: Surface Expression of α4 Integrin by CD4 T Cells Is Required for Their Entry into Brain Parenchyma, J. L. Baron, J. A. Madri, N. H. Ruddle, J. Hashim and C. A. Janeway, Jr., J. Exp. Med., 177 (1993) 57–68].

Antibodies specific for both α4-integrin (LPAM-1) and one of its ligands, VCAM-1, were also shown to be effective in treating insulin-dependent diabetes mellitus in the non-obese diabetic mouse. Insulin-dependent diabetes mellitus is believed to be an autoimmune disease in which activated T lymphocytes destroy the insulin-producing β-cells of the pancreatic islets. The antibody R1-2 prevented the onset of insulitis in a dose-dependent manner in nonobese diabetic mice. The blocking of disease was accompanied by a marked decrease in lymphocytic infiltration of the islets of Langerhans. [Reference: The Pathogenesis of Adoptive Murine Autoimmune Diabetes Requires an Interaction Between α 4-Integrins and Vascular Cell Adhesion Molecule-1, J. L. Baron, E-P. Reich, I. Visintin and C. A. Janeway, Jr., J. Clin. Invest., 93 (1994) 1700–1708].

Cells expressing integrin α4β1 have been shown to bind to sequences in the heparin II binding domain and the alternatively spliced type III connecting segment (IIICS) located in the carboxy-terminal cell binding domain of fibronectin. Within the IIICS region, α4β1 binds with high affinity to a peptide sequence termed CS-1 (a 25-amino acid peptide), suggesting that this is the major site of α4β1 interaction in fibronectin. The tripeptide Leu-Asp-Val is the minimal sequence within CS-1 capable of supporting hematopoietic cell adhesion or of inhibiting α4β1-mediated cell binding to fibronectin. [References for CS1: The Minimal Essential Sequence for a Major Cell Type-Specific Adhesion Site (CS1) Within the Alternatively Spliced Type III Connecting Segrnent Domain of Fibronectin is Leucine-Aspartic Acid-Valine, A. Komoriya, L. J. Green, M. Mervic, S. S. Yamada, K. M. Yamada and M. J. Humphries, J. Biol. Chem., 23 (1991) 15075–15079; Activation-Dependent Recognition by Hematopoietic Cells of the LDV Sequence in the V Region of Fibronectin, E. A. Wayner and N. L. Kovach, J. Cell Biol., 116 (1992) 489–497.]

In addition to the Leu-Asp-Val containing sequences mentioned above, a cyclic octapeptide 1-adamantaneacetyl-Cys-Gly-Arg-Gly-Asp-Ser-Pro-Cys (containing a disulphide bridge between the two cysteine residues) has been reported to be as effective as the LDV containing peptide Cys-Leu-His-Gly-Pro-Glu-Ile-Ieu-Asp-Val-Pro-Ser-Thr in blocking Jurkat cell adhesion to CS-1 coated plates ($IC_{50}$ 30 μM). The cyclic peptide also inhibited the binding of Jurkat ceuls to fibronectin coated plates. In addition to inhibiting α4β1-induced adhesion, the octapeptide also inhibited function in αvβ3 as well as αIIbβIIIa-dependent assays. Therefore the peptide is not selective for α4β1-mediated adhesion. [Reference: Cyclic RGD Peptide Inhibits α4β1 Interaction with Connecting Fragment 1 and Vascular Cell Adhesion Molecule, P. M. Cardarelli, R. R. Cobb, D. M. Nowlin, W. Scholz, F. Gorcsan, M. Moscinski, M. Yasuhara, S-L. Chiang and T. J. Lobl, J. Biol. Chem., 269 (1994) 18668–18673.]

A few small non-peptidic compounds [Reference: Non-peptidic Surrogates of the Leu-Asp-Val Sequence and Their Use in the Treatment of Inflammation, Autoimmune Diseases and Tumour progression, YEDA Research and Development Co. Ltd, WO 94/02445, Publ. date Feb. 3, 1994] have also been reported to inhibit α4β1-induced adhesion.

A disulphide cyclic pentapeptide, Arg-Cys-Asp-thioproline-Cys (thioproline=thiazolidine-4-carboxylic acid), has also been reported to be an inhibitor of leukocyte cell adhesion to fibronectin. In addition, the cyclic peptide also inhibited the binding to the 120 kDa chymotryptic fragment of fibronectin, which contains the Arg-Gly-Asp central cell binding domain. Again, the peptide was not selective. It binds to both α4β1 and α5β1 [Reference: A Novel Cyclic Pentapeptide Inhibits α4β1 and α5β1 Integrin-Mediated Cell Adhesion, D. M. Nowlin, F. Gorcsan, M. Moscinski, S-L. Chiang, T. J. Lobl and P. M. Cardarelli, J. Biol. Chem., 268 (1993) 20352–20359.]

The present invention is based on the discovery that relatively small cyclic peptides can potently inhibit the interaction of VCAM-1 and fibronectin with integrin VLA4.

According to one aspect of the present invention there is provided a cyclic peptide of formula 1 (FIG. 1) wherein:

AA1 represents an L or D amino acid selected from Ile, Leu, Pro, Gly or Tic or amino acid analogue thereof AA2 represents an L amino acid selected from Leu, Ile, Phe or Val or amino acid analogue thereof AA3 represents an L amino acid selected from Asp or Glu or amino acid analogue thereof AA4 represents an L amino acid selected from Val, Leu, Ile, Phe or Cha (cyclohexylalanine) or amino acid analogue thereof LINKER represents a linking moiety for linking AA1 to AA4 to form a cyclic peptide in which the linking moiety is smaller in length than —$(CH_2)_{11}$— (preferably smaller than —C(O)—$(CH_2)_{11}$—NH—; preferably smaller than —C(O)—$(CH_2)_{10}$—NH—; preferably smaller than —C(O)—$(CH_2)_9$—NH—; preferably smaller than —C(O)—$(CH_2)_8$—NH—; preferably smaller than —C(O)—$(CH_2)_7$—NH—;);

the peptide preferably having an $IC_{50}$ of <20 μM, more preferably <15 μM, in the MOLT-4 cell/fibronectin assay described herein or the peptide having an $IC_{50}$ of <100 μM, preferably <50 μM, in the MOLT-4 cell/recombinant soluble VCAM-1 assay described herein and AA1-4 have the general formula 2 (FIG. 1) wherein R1 is the amino acid side chain and R2 and R3 independently represent H or $C_{1-4}$ alkyl (preferably H or Me, especially H). An amino acid analogue is defined herein as an amino acid having the same side chain characteristics, for example hydrophobicity or the presence of a functional group (e.g. COOH) or a mimetic thereof (such as for example tetrazole in the case of COOH), as the amino acid which it replaces.

Preferably the linking moiety is greater in length than —C(O)—$(CH_2)_2$—NH—. (Note the cyclic tetrapeptide Ile-Leu-Asp-Val linked N to C terminus by —C(O)—$(CH_2)_2$—NH—(β-alanine) was inactive in biological tests at 200 μM). The term LINKER does not include a replicate of AA1-AA4 per se. (A further aspect of the invention is set out below in which the LINKER is defined as being part of a heterocyclic ring formed with AA1-AA4. Where applicable, preferred values and explanations of terms apply to either way of defining the invention.).

In this specification the generic term "alkyl" includes both straight-chain and branched-chain alkyl groups. However references to individual alkyl groups such as propyl are specific for the straight chain version only and references to individual branched chain alkyl groups such as isopropyl are specific for the branched chain version only. An analogous convention applies to other generic terms. Compounds of the present invention include solvates such as for example hydrates. Compounds of the present invention include prodrugs such as for example in vivo hydrolysable esters. The terms "aryl" and "heteroaryl" include optional mono- or di-substition with groups independently selected from $C_{1-4}$alkyl, $C_{1-4}$alkoxy, hydroxy, halogen, cyano and trifluoromethyl.

Preferred values are:

AA1 is Ile, D-Ile, MeIle (especially D-Ile & MeIle); AA2 is Leu; AA3 is Asp; AA4 is Val Preferred Ile analogues are shown in FIG. 5. A preferred analogue of Ile is D-Ile. Preferred values for LINKER exclude disulphide bonds, especially between Cys residues. In this specification the tetrapeptide -AA1-AA2-AA3-AA4- has its N-terminus at AA1 and its C-terminus at AA4 unless otherwise stated or implicit; and amino acids have L configuration unless otherwise stated or implicit from the context.

Suitable values for AA1 include tert-Leu and tert-butyl-Ala.

LINKER is preferably a group of formula 4 (FIG. 1) wherein n=3–5 (especially n=3) and R4 and R5 represent H or;

R4 represents $NH_2$ optionally substituted with a $C_{1-10}$acyl or $C_{1-10}$.O.CO group (where $C_{1-10}$ is alkyl, aryl, heteroaryl, arylalkyl or heteroarylalkyl) such as for example $C_{2-5}$alkanoyl (especially isobutylcarbonyl, $CH_3C(O)$—, $CH_3CH_2C(O)$—, cyclopropylcarbonyl-, cyclobutylcarbonyl-), tert-butoxycarbonyl (Boc), benzyloxycarbonyl, pyridyl-carbonyl (especially pyridyl-3-yl-carbonyl);

or $NH_2$ is optionally substituted with amino acids via α-carboxyl such as for example Glu, Asp, Pro-Glu or Pro-Asp, the N terminus of the amino acid optionally being protected with a $C_{1-10}$acyl or $C_{1-10}$.O.COgroup (where $C_{1-10}$ is alkyl, aryl, heteroaryl, arylalkyl or heteroarylalkyl)group such as for example $CH_3C(O)$—, $CH_3CH_2C(O)$—, cyclopropylcarbonyl-, cyclobutylcarbonyl-, Boc;

or $NH_2$ is optionally mono or di substituted with $C_{1-4}$alkyl (especially diethyl) or $NH_2$ is optionally substituted with benzyl, pyridyl, carboxy$C_{2-5}$alkanoyl (especially 3-carboxy-propionyl), amino-$C_{2-5}$alkanoyl (especially 3-amino-propionyl), and R5 is H or;

R4 is H and R5 is COOH optionally substituted to give an ester such as for example —COOMe; COOEt, —COOPr, COOBu or R5 is an amide such as for example —$CONH_2$, —CONHMe, —CONHEt, —CONHPr, —CONHBu. R4=R5=H is especially preferred.

Suitable values for n include 3-9, 3-8, 3-7, 3-6, 3-5, 3-4, 3, 4, 5, 6, 7, 8 and 9.

Further preferred values for LINKER are shown in FIGS. 8 and/or 13.

According to one aspect of the present invention there is provided a cyclic peptide of formula 1 (FIG. 1) wherein:

AA1 is an L or D amino acid selected from Ile and Leu or amino acid analogue thereof;

AA2 is an L amino acid selected from Leu or amino acid analogue thereof;

AA3 is an L amino acid selected from Asp or amino acid analogue thereof containing a carboxyl group (or optionally a COOH mimetic, especially tetrazole) in its side chain and;

AA4 is an L amino acid selected from Val or amino acid analogue thereof.

LINKER represents a linking moiety for linking N terminus of AA1 to C terminus of AA4 to form a cyclic peptide containing a heterocyclic ring having 17 to 30 members; the cyclic peptide having an $IC_{50}$ of <20 μM (preferably, in increasing order, <10, <3, <1, <0.3, <0.1, <0.03 μM) in the MOLT-4 cell/fibronectin assay described herein and/or;

the cyclic peptide having an $IC_{50}$ of <100 μM (preferably, in increasing order, <50, <30, <10, <3, <1, <0.3, <0.1, <0.03 μM) in the MOLT-4 cell/recombinant soluble VCAM-1 assay described herein and;

AA1-4 have the general formula 2 (FIG. 1)

wherein R1 is the amino acid side chain and

R2 and R3, which may be the same or different for each of AA1-AA4, independently represent H or $C_{1-4}$alkyl;

or a salt thereof.

Preferred values for the number of members in the heterocyclic ring formed by the linking moiety (LINKER) for linking the N terminus of AA1 to the C terminus of AA4 are 17 to 29 members; more preferably 17 to 28 members; more preferably 17 to 27 members; more preferably 17 to 26 members; more preferably 17 to 25 members; more preferably 17 to 24 members; more preferably 17 to 23 members; more preferably 17 to 22 members: more preferably 17 to 21 members; more preferably 17 to 20 members; more preferably 17 to 19 members; more preferably 17 to 18 members and 18 members are especially preferred.

Where the heterocyclic ring formed by the linking moiety (LINKER) for linking the N terminus of AA1 to the C terminus of AA4 itself contains a ring (an internal ring) then the number of members in the heterocyclic ring is counted as including only those members of the internal ring which form the shortest route to completing the heterocyclic ring. For example compound 16 in Table 2 has 20 members in its heterocyclic ring within the meaning of this definition and likewise compound 17 has 18 members.

Preferably the cyclic peptide described above has the following values:

for AA1 the amino acid analogue is selected from Val, Pro, Gly, Tic, tert-Leu, tert-butyl-Ala, Phe, Nle, Met, Arg, Lys, Ala;

for AA2 the amino acid analogue is selected from Ile, Phe, Val, tert-Leu, Nle, Cha and tert-butyl-Ala;

for AA3 the amino acid analogue is Glu;

for AA4 the amino acid analogue is selected from Leu, Ile, Phe, Cha, Nle and Nva;

or a salt thereof.

More preferably the cyclic peptide described above has the following values:

AA1 is selected from Ile and Leu either of which is optionally N-methylated;

AA2 is Leu; AA3 is Asp and; AA4 is Val;

or a salt thereof.

Preferably the cyclic peptide described above has the following values:

LINKER is a group of formula 4 (FIG. 1)

wherein:

n=3–5 and

R4 and R5 represent H or; R4 represents $NH_2$ optionally substituted with a $C_{1-10}C(O)$— group;

or $NH_2$ is optionally substituted with natural amino acids via α-carboxyl, the N terminus of the amino acid optionally being substituted with a $C_{1-10}C(O)$— group;

or NH$_2$ is optionally mono or di substituted with C$_{1-4}$alkyl;

or NH$_2$ is optionally substituted with benzyl, pyridyl, carboxyC$_{2-5}$alkanoyl, amino-C$_{2-5}$alkanoyl, and R5 is H or;

R4 is H and R5 is COOH optionally substituted with C$_{1-4}$alkyl to give an ester or R5 is an amide of formula —CONR6R7 where R6 and R7 independently represent H or C$_{1-4}$alkyl;

or a salt thereof.

In this specification bonds illustrated with arrow heads indicate direct bonds or attachment points, that is not —CH$_2$— groups, unless otherwise stated or implicit. In this specification amino acids are linked in conventional manner unless otherwise indicated or implicit and amino acids have L configuration unless stated otherwise or implicit.

Preferably the cyclic peptide described above has the following values:

LINKER represents any one of formulas 6–44 as set out in FIG. 13, or a salt thereof.

More preferably the cyclic peptide described above has the following values:

LINKER represents any one of formulas 6, 7, 8, 13, 17, 18, 19, 20 or 21–44 as set out in FIG. 13, or a salt thereof.

Preferred cyclic peptides, in which annotations in square brackets refer to the LINKER portion thereof and MeIle represents N-methyl-Ile, are:

SEQ ID No: 3 c(Ile-Leu-Asp-Val-NH—(CH$_2$)$_5$—CO—)

SEQ ID No: 4

D-Ile-Leu-Asp-Val-NH(CH$_2$)$_5$CO

SEQ ID No: 11

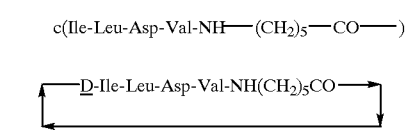
[D-Lys analogue]

SEQ ID No: 13

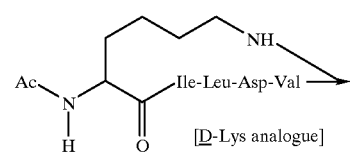
[L-Orn analogue]

SEQ ID No: 9

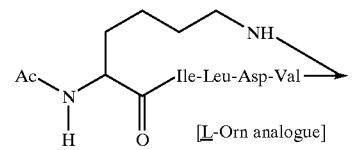

SEQ ID No: 14

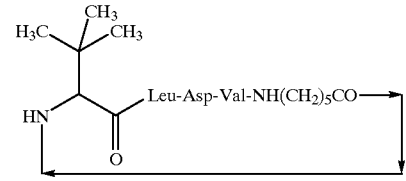
[D-Lys analogue]

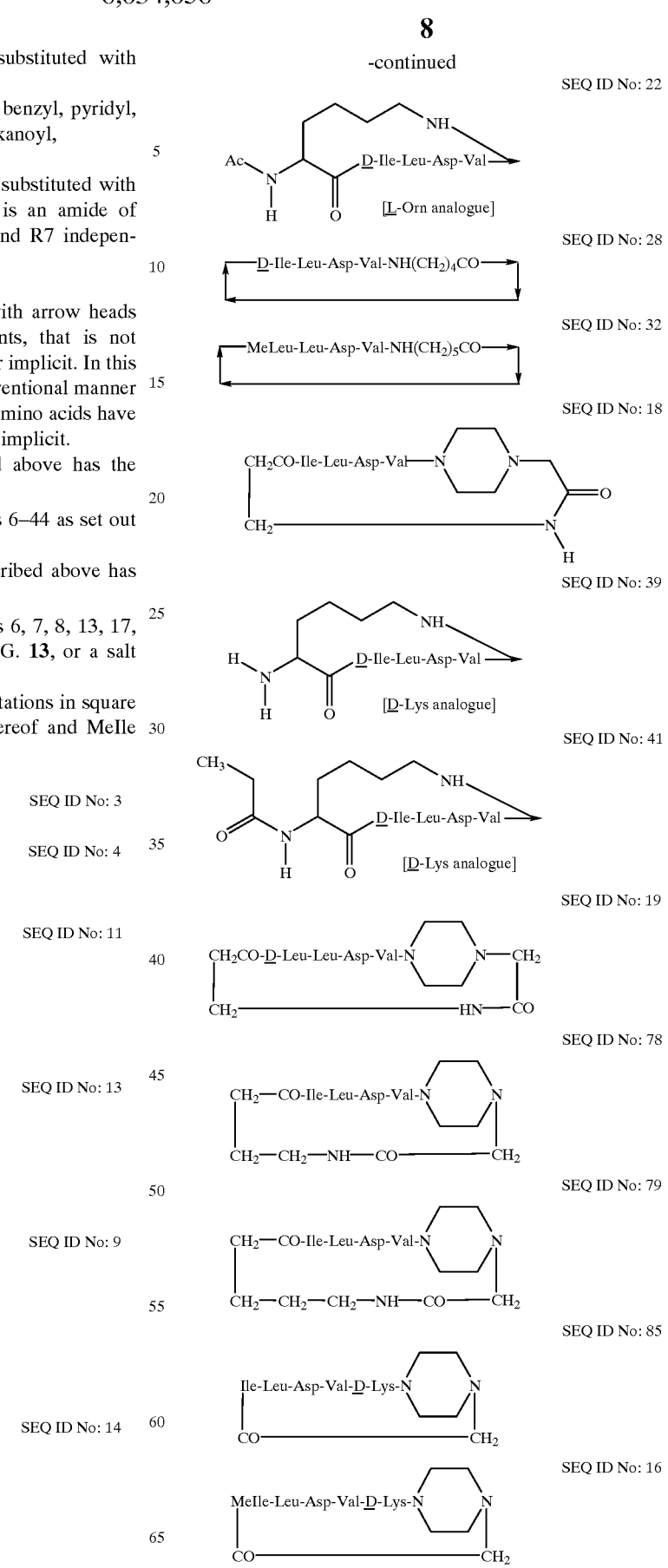

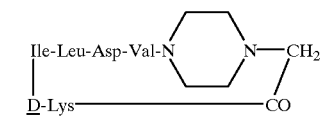

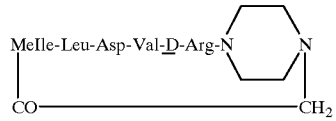

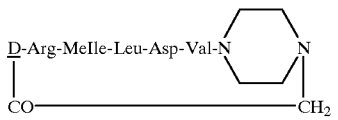

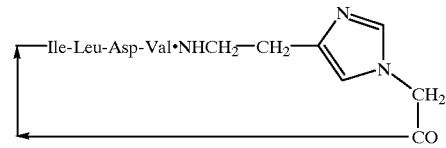

SEQ ID No: 44

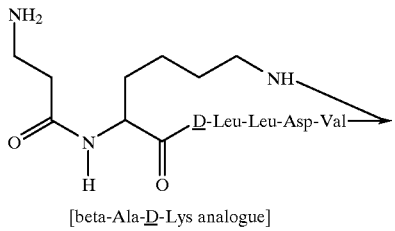

[beta-Ala-D-Lys analogue]

SEQ ID No: 49

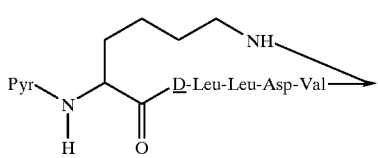

[N-Pyr-D-Lys analogue]

SEQ ID No: 47

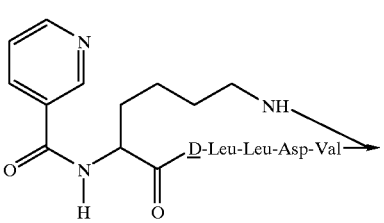

[N-Pyridylcarbonyl-D-Lys analogue]

SEQ ID No: 48

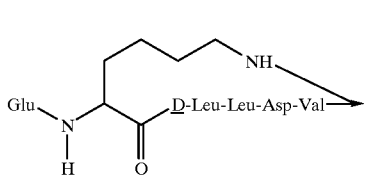

[alpha-Glu-D-Lys analogue]

SEQ ID No: 54

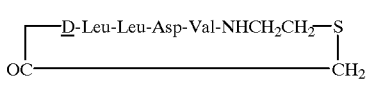

SEQ ID No: 55

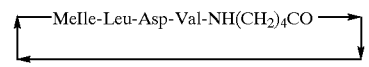

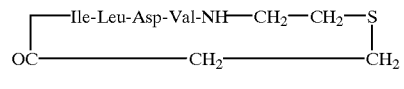

SEQ ID No: 58 c(D-Leu-Leu-Asp-Val-β-Ala-Pro)

SEQ ID No: 63 c(D-Leu-Leu-Asp-Val-D-Ala-D-Ala)

SEQ ID No: 64 c(D-Leu-Leu-Asp-Val-β-Ala-D-Ala)

SEQ ID No: 66

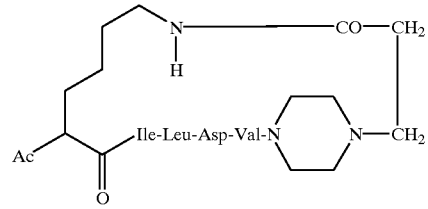

SEQ ID No: 80

(Seq I.D. 73)

c(MeIle-Leu-Asp-Val-β-Ala-Pro)

(Seq I.D. 74)

c(MeIle-Leu-Asp-Val-β-Ala-D-Ala)

(Seq I.D. 75)

c(MeIle-Leu-Asp-Val-D-Ala-D-Ala)

(Seq I.D. 76)

c(MeIle-Leu-Asp-Val-β-Ala-D-Orn)

(Seq I.D. 77)

c(MeIle-Leu-Asp-Val-β-Ala-D-Lys)

c(MeIle-Leu-Asp-Val-D-Arg-D-Ala)

c(MeIle-Leu-Asp-Val-D-Ala-D-Arg)

c(MeIle-Leu-Asp-Val-D-Orn-D-Ala)

c(MeIle-Leu-Asp-Val-D-Lys-D-Ala)

c(MeIle-Leu-Asp-Val-D-Orn(CHMe₂)-D-Ala)

c(MeIle-Leu-Asp-Val-D-Orn(cyclohexyl)-D-Ala)

c(MeIle-Leu-Asp-Val-D-Orn(4-chlorobenzyl)-D-Ala)

c(MeIle-Leu-Asp-Val-D-Orn(Et₂)-D-Ala)

c(MeIle-Leu-Asp-Val-D-Lys(CHMe₂)-D-Lys(CHMe2))

c(MeIle-Leu-Asp-Val-D-Lys-D-Lys)

c(MeIle-Leu-Asp-Val-D-Ala-D-Lys)

c(MeIle-Leu-Asp-Val-D-Phe-D-Lys)

c(MeIle-Leu-Asp-Val-D-Trp-D-Lys)

c(MeIle-Leu-Asp-Val-D-Phe-D-Arg)

c(MeIle-Leu-Asp-Val-D-Trp-D-Arg)

c(MeIle-Leu-Asp-Val-D-Arg-(Pmc)-D-Ala)

c(MeIle-Leu-Asp-Val-D-Ala-D-Arg(Pmc))

c(MeIle-Leu-Asp-Val-D-Phe-D-Arg(Pmc))

c(MeIle-Leu-Asp-Val-D-Trp-D-Arg(Pmc))

c(MeIle-Leu-Asp-Val-D-His-D-Lys)

c(MeIle-Leu-Asp-Val-D-Arg-D-Arg)

c(MeIle-Leu-Asp-Val-D-His-D-Arg)

c(MeIle-Leu-Asp-Val-D-Arg-D-His)

c(MeIle-Leu-Asp-Val-D-Ala-D-Orn)

c(MeIle-Leu-Asp-Val-D-Orn-D-Orn);

or a salt thereof.

According to another aspect of the present invention there is provided a cyclic peptide of formula 5 (see FIG. 1) wherein the variable groups are as defined for formula 1 and additionally AA0 represents Glu and AA5 represents Pro.

The cyclic peptides of the present invention have at least one of the following advantages: they are more potent than known compounds, e.g. CS1 in our tests; they are smaller than CS-1, a 25-amino acid peptide, and therefore easier to synthesise and; cyclic peptides are more stable to enzymic degradation.

Some preferred compounds are set out in FIG. 2. Especially preferred compounds have shown activity in in vivo screens [for example in the mouse in vivo CHS (contact hypersensitivity) model—Example 2.3] as set out below. CS1 at 10 mg/kg/day and 1 mg/kg/day gave 0% inhibition. Compound 3 (FIG. 2) and Compound 4 (FIG. 2) were active at 10 mg/kg/day (39% inhibition) and 1 mg/kg/day (19% inhibition). No toxicity at the effective dose was observed for compounds tested of the present invention.

According to a further feature of the invention there is provided a pharmaceutical composition which comprises a cyclic peptide of the invention in association with a pharmaceutically acceptable diluent or carrier.

The composition may be in a form suitable for oral use, for example a tablet, capsule, aqueous or oily solution, suspension or emulsion; for nasal use, for example a snuff, nasal spray or nasal drops; for vaginal or rectal use, for example a suppository; for administration by inhalation, for example as a finely divided powder or a liquid aerosol; for sub-lingual or buccal use, for example a tablet or capsule; or for parenteral use (including intravenous, subcutaneous, intramuscular, intravascular or infusion), for example a sterile aqueous or oily solution or suspension, or a depot formulation with drug incorporated in a biodegradable polymer. The composition may be in a form suitable for topical administration such as for example creams, ointments and gels. Skin patches are also contemplated. Formulation in general is described in Chapter 25.2 of Comprehensive Medicinal Chemistry, Volume 5, Editor Hansch et al, Pergamon Press 1990.

In general the above compositions may be prepared in a conventional manner using conventional excipients. However, in the case of a composition for oral administration, it may be convenient for the composition to include a coating to protect the cyclic peptide active ingredient from the actions of enzymes in the stomach.

A preferred composition of the invention is one suitable for oral administration in unit dosage form for example a tablet or capsule which contains from 2.5 to 500 mg, and preferably 10 to 100 mg, of cyclic peptide in each unit dose, or one suitable for parenteral administration which contains from 0.5 to 100 mg of cyclic peptide per ml, and preferably 1 to 10 mg of cyclic peptide per ml of solution.

A parenteral composition is preferably a solution in isotonic saline or isotonic dextrose buffered if necessary to a pH of 5 to 9. Alternatively, the parenteral composition may be one designed for slow release in which case the amount of cyclic peptide per unit dose is in general greater than that required when a conventional injectable formulation is used.

A preferred slow release formulation is a continuous release formulation, for example a formulation of the type described in European Patent Specification No. 58481. For slow release formulations containing polylactic/polyglycolic based polymers it is preferred to have a cyclic peptide of the invention containing a basic group in the LINKER. Further preferred values for cyclic peptides described herein are those in which LINKER represents a dipeptide (of formula ←NH—CHR'—CO—NH—CHR"—CO→ wherein R' and R" represent amino acid side chains and the dipeptide is optionally substituted by $C_{1-4}$alkyl (especially methyl) on N in the peptide backbone and/or side chain) preferably containing at least one basic amino acid or a salt thereof, more preferably the amino acids in the dipeptide are D amino acids or a salt thereof and especially the dipeptide is selected from any one of formulas 24–38, 43 and 44 as set out in FIG. 13 herein or a salt thereof. A basic amino acid is defined as one containing a basic functional group in its side chain, such as for example amino or guanidino either of which may be optionally substituted with $C_{1-4}$alkyl. A preferred slow release parenteral formulation contains from 10 to 100 mg of cyclic peptide per unit dose. In another embodiment of the invention in which LINKER represents a dipeptide one of the amino acids in the dipeptide can optionally be an amino acid without a side chain such as for example β-alanine.

The composition of the invention will normally be administered such that a daily oral dose will be from 0.1 mg/kg, to 50 mg/kg and a daily parenteral dose, will be from 20 micrograms/kg to 10 mg/kg.

According to a further feature of the invention there is provided a method for inhibiting the interaction between VCAM-1 and/or fibronectin and the integrin receptor VLA-4 in warm-blooded animals such as man in need of such treatment which comprises administering to said animal an effective amount of a cyclic peptide of formula I or a pharmaceutically acceptable salt thereof. The invention also provides the use of such a cyclic peptide of formula I or a pharmaceutically-acceptable salt thereof in the production of a new medicament for use in the treatment of a disease or medical condition mediated by the interaction between fibronectin and/or VCAM-1 (especially VCAM-1) and the integrin receptor VLA-4. Utility as tools for research is also contemplated.

According to another aspect of the present invention there is provided a pharmaceutical composition comprising a cyclic peptide as herein described in association with a pharmaceutically acceptable diluent or carrier. A preferred pharmaceutical composition is for parenteral administration designed for slow release over a period of at least 5 days.

According to another aspect of the present invention there is provided a cyclic peptide as herein described for use as a medicament. According to another aspect of the present invention there is provided a method for inhibiting the interaction between VCAM-1 and/or fibronectin and the integrin receptor VLA-4 in mammals in need of such treatment which comprises administering to said mammal an effective amount of a pharmaceutical composition as described herein or a pharmaceutically acceptable salt thereof. In a preferred embodiment the mammal in need of treatment is suffering from multiple sclerosis or rheumatoid arthritis.

According to another aspect of the present invention there is provided the use of a cyclic peptide of formula I or a pharmaceutically-acceptable salt thereof in the production of a medicament for use in the treatment of a disease or medical condition mediated by the interaction between VCAM-1 or fibronectin and the integrin receptor VLA-4.

Synthetic Details

A cyclic peptide of the invention of formula I may be prepared by any process well known in the art of peptide chemistry to be applicable to the synthesis of analogous compounds. Thus, for example, a cyclic peptide of the invention may be obtained by procedures analogous to those disclosed in "Solid Phase Peptide Synthesis: A practical approach" by Atherton and Sheppard (published by IRL press at Oxford University Press, 1989), "Solid Phase Peptide Synthesis" by Stewart and Young (published by the Pierce Chemical Company, Illinois, 1984), "Principles of Peptide Synthesis" by M. Bodanszky (published by Springer-Verlag, Berlin Heidelberg, 1984), "The Practice of Peptide Synthesis" by M. Bodanszky and A. Bodanszky (published by Springer-Verlag, Berlin Heidelberg, 1984), and a series of books "Amino Acids, Peptides and Proteins" (volumes 1–26; volume 26 published in 1995) (published by the Royal Society of Chemistry, Cambridge, UK). In addition to books, a number of reviews [e.g. "Solid Phase Peptide Synthesis: a Silver Anniversary Report", G. Barany, N. Kneib-Cordonier and D. G. Mullen, International Journal of Peptide and Protein Research, 30 (1987) 705–739; "Solid Phase Peptide Synthesis Utilising 9-Fluorenylmethoxycarbonyl Amino Acids", G. B. Fields and R. L. Noble, International Journal of Peptide and Protein Research, 35 (1990) 161–214] have also been published on the synthesis of peptides Synthetic advances are also published in the proceedings of the American, European and Japanese Peptide Symposiums. Synthesis may be achieved by automated or manual means.

According to another aspect of the present invention there is provided a process for the manufacture of a cyclic peptide of formula 1 selected from: (a) the removal of one or more conventional peptide protecting groups from a protected cyclic peptide of Formula 3 (FIG. 1) wherein Pr1 represents a protecting group on the acid group in the side chain of AA3 to give a cyclic peptide of the invention of formula I and optionally, simultaneously or subsequently, also removing any additional conventional peptide protecting groups present in the LINKER and optionally if desired converting the product thus obtained into a salt thereof;

(b) the formation of an amide bond by coupling two peptide units, one containing a carboxylic acid group, or a reactive derivative thereof, and the other containing an amino group, such that a protected or unprotected cyclic peptide having the sequence indicated in formula I is produced, and if necessary, the protecting groups are removed using process (a) above and optionally if desired converting the product thus obtained into a salt thereof;

(c) for a cyclic peptide according to formula 1, having —S(O)— or —S(O$_2$)— in the LINKER, oxidising —S— (or additionally —S(O)— in the case of —S(O$_2$)—) in the LINKER of a precursor cyclic peptide to give a cyclic peptide containing —S(O)— or —S(O$_2$)— in its LINER and optionally if desired converting the product thus obtained into a salt thereof.

The above deprotection and coupling steps can be performed either on a solid support (Solid Phase Peptide Synthesis) or in solution using normal techniques used in the synthesis of organic compounds. With the exception of the solid support, all the other protecting groups, coupling reagents, deblocking reagents and purification techniques are similar in both the solid phase and solution phase peptide synthesis techniques.

For the synthesis of peptides on the solid support, a suitable resin is selected which can either provide a free carboxyl group after cleavage from the resin or a peptide derivative which can be selectively deprotected to give a C-terminal carboxyl group. The solid support may consist of polystyrene beads, polydimethylacrylamide beads, polydimethylacrylamide/polystyrene composite (Polyhipe) or polystyrene-polyoxyethylene resin (Tentagel resins). A few examples of suitable linker group containing solid supports used in the solid phase synthesis of peptides are shown below. In addition to the linkers shown, some other linkers such as hydroxycrotonoylamidomethyl (HYCRAM) can also be used. The first amino acid is then coupled to the resin by the methods described in this application for the synthesis of peptides or by using any of the coupling reagents used in the synthesis of peptides. Examples of some of the coupling reagents are also described in this application.

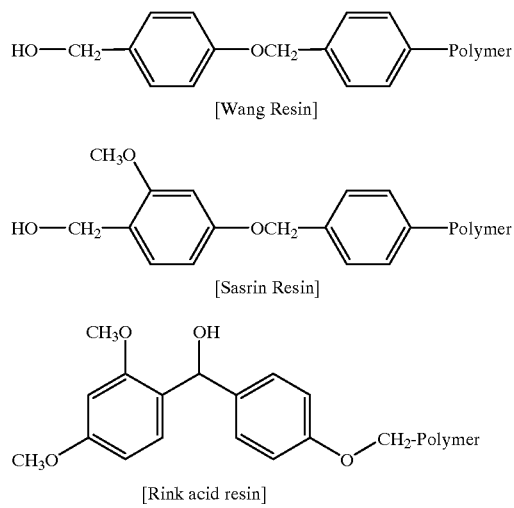

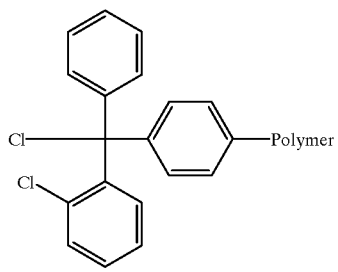

[2-Chlorotritylchloride resin]

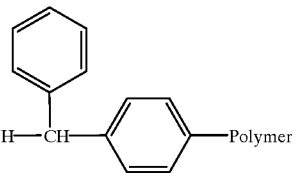

[HMPB Linker Resin]

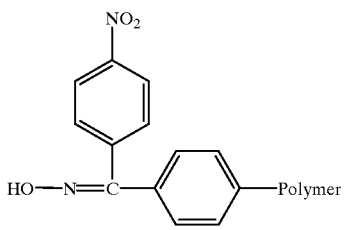

[Oxime resin]

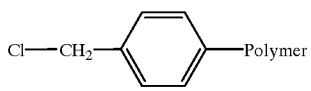 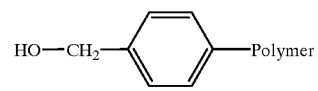

[Merrifield chloromethyl and hydroxymethyl resins]

During the assembly of peptides, the amino acid functional groups not taking part in the reaction are protected by various protecting groups. For example, the N-terminal and the side chain amino groups can be protected by using 9-fluorenylmethoxycarbonyl (Fmoc), t-butoxycarbonyl (Boc), biphenylisopropoxycarbonyl (Bpoc), 2-[3,5-dimethoxyphenyl]propyl-2-oxycarbonyl (Ddz), adamantyloxycarbonyl (Adoc), allyloxycarbonyl (Aloc), 2,2,2-trichloroethoxycarbonyl (Troc), benzyloxycarbonyl and various substituted benzyloxycarbonyl groups. These protecting groups can be cleaved when required by the standard techniques (e.g. acid or base treatment, catalytic hydrogenolysis and Pd(0) treatment or zinc/acetic acid treatment).

Suitable protecting groups used for the protection of the α-carboxyl or the side chain carboxyl groups include various esters (e.g. methyl, ethyl, t-butyl, benzyl, nitrobenzyl, allyl and 9-fluorenylmethyl).

Suitable protecting groups used for the protection of the side chain guanidino group in the peptides containing an arginine residue include a nitro, adamantyloxycarbonyl, 4-methoxy-2,3,6-trimethylbenzenesulphonyl (Mtr), 2,2,4,6,7-pentamethyldihydrobenzofuran-5-sulphonyl (Pbf) and 2,2,5,7,8-pentamethylchroman-6-sulphonyl (Pmc) groups. Suitable protecting groups used for the protection of the side chain imidazole group in the peptides containing a histidine residue include a trityl, tosyl, dinitrophenyl, Adoc, Boc or Fmoc group.

The protecting group cleavage reactions can be performed at temperatures between 4° C. to 40° C. (preferably at room temperature, about 25° C.). The cleavage reactions can take between 10 minutes to 24 hours.

Suitable coupling methods used for the coupling of the individual amino acids or the peptide fragments include the commonly used azide, symmetrical anhydride, mixed anhydride and various active esters and carbodiimides. In case of various carbodiimides (e.g. dicyclohexyl- or diisopropyl-carbodiimides), a number of additives [e.g. 1-hydroxybenzotriazole and N-hydroxysuccinimide] may also be added. In addition, the amino acid or fragment couplings can also be achieved by using a number of other reagents, e.g. 1H-benzotriazole-1-yl-oxy-tris-pyrrolidinophosphonium hexafluorophosphate (PyBOP), (2-(1H-benzotriazole-1-yl)-1,1,3,3-tetramethyluronium tetrafluoroborate (TBTU) and (2-(1H-benzotriazole-1-yl)-1,1,3,3-tetramethyluronium hexafluorophosphate (HBTU)].

The coupling reactions can be performed at temperatures between −20° C. to 40° C. The time required for completion of the reaction may be between 10 minutes to 24 hours.

Suitable purification methods for the intermediates and final products include counter current distribution, ion exchange, gel filtration and various other chromatographic techniques including high pressure liquid chromatography (HPLC) along with many other standard techniques used in organic chemistry (e.g. solvent extraction and crystallisation).

Salts may be prepared by any suitable method known in the art. Pharmaceutically acceptable salts include, but are not limited to, inorganic salts such as sodium, potassium, calcium and the like and organic salts with amines or organic bases.

BRIEF DESCRIPTION OF DRAWINGS

The invention will now be illustrated by the following non-limiting examples in which FIG. 1 illustrates chemical formulae.

FIG. 2 illustrates the structures of some preferred compounds of the present invention.

FIG. 3 illustrates a general procedure used for the synthesis of cyclic peptides in which the starting material was made by solid phase synthesis on chlorotrityl resin.

FIG. 4 illustrates the structures of Tic, Pyr and a detailed structure of compound 3 in FIG. 2.

FIG. 5 illustrates analogues of Ile.

FIG. 6 illustrates compounds mentioned in Example 1, paragraph 7.

FIG. 8 illustrates some preferred LINKER structures.

FIG. 9 illustrates compounds mentioned in Example 1, paragraph 22.

FIG. 10 compares different representations of the same cyclic peptide.

FIG. 11 illustrates synthesis of end product 11 (in Table 2).

FIG. 12 illustrates synthesis of end product 17 (in Table 2).

FIG. 13 illustrates some preferred LINKERs; note that structures 6–18 are written C terminus to N terminus and the remainder vice versa.

FIG. 14 illustrates the structure of Fmoc-Arg(Pmc).

FIG. 15 illustrates the structures of N-MeAla and Asp(OBu$^t$).

FIG. 16 illustrates the structures of norleucine (Nle), norvaline (Nva) and cyclohexylalanine (Cha).

Figure 7:
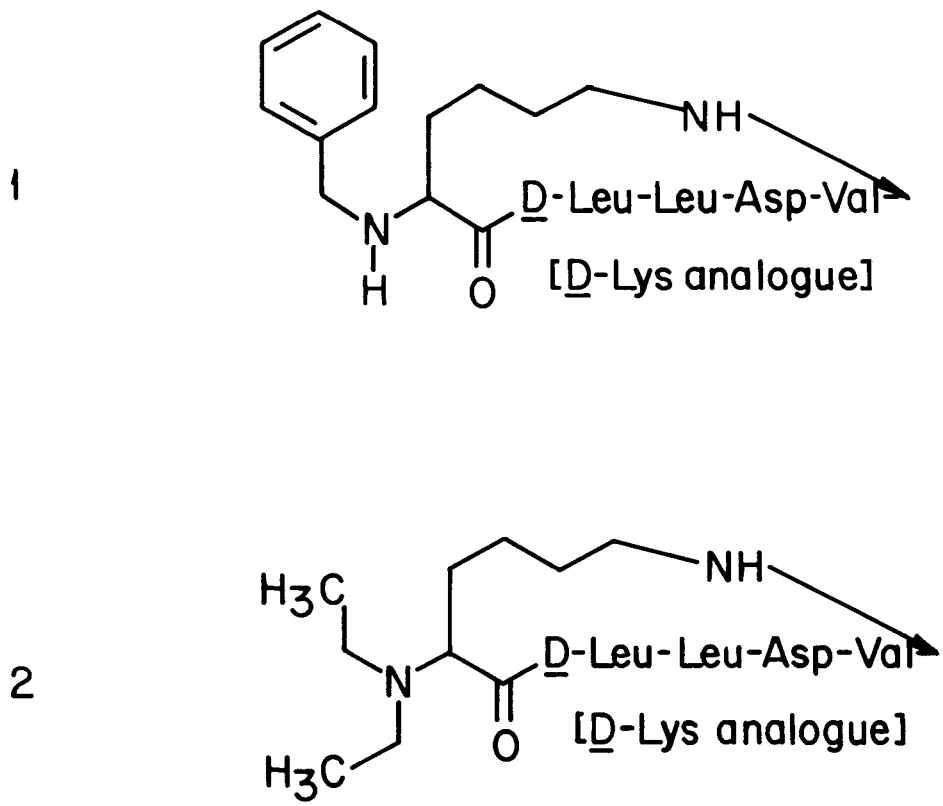
FIG. 7 illustrates end products mentioned in Example 1, paragraphs 17 & 16.

Table 1 illustrates synthesis and purification of cyclic peptides. Annotations in square brackets refer to the LINKER portion of the cyclic peptide. Table 2 illustrates characterisation of cyclic peptides. Annotations in square brackets refer to the LINKER portion of the cyclic peptide.

In the Figures and Tables arrowed bonds indicate attachment points or direct bonds only (ie not a —$CH_2$— group) unless otherwise stated or implicit. Illustrations of arrowed attachment points for linkers will be such that: a nitrogen atom will link to a —C(O)— at the C-terminus of the relevant peptide and; likewise a —C(O)— will link to a nitrogen atom at the N-terminus of the relevant peptide; unless otherwise stated or implicit. For further guidance: the structure of the linear precursor can be compared with the appropriate end product cyclic peptide in Table 1 and; FIG. 10 compares different representations of the same structure. The following abbreviations have been used.

| | |
|---|---|
| Ac | acetyl |
| Ahx | 6-amino-hexanoic acid |
| Boc | tert-butoxycarbonl |
| Cha | cyclohexylalanine |
| Dab | 2,4-diamino-butyric acid |
| Fmoc | 9-fluorenylmethoxycarbonyl |
| HPLC | high pressure liquid chromatography |
| Nle | norleucine |
| Orn | ornithine |
| Pmc | 2,2,5,7,8-pentamethylchroman-6-sulfonyl |
| Pyr | pyroglutamic acid (see FIG. 4) |
| Tic | 1,2,3,4-tetrahydroisoquinoline-3-carboxylic acid |
| Z | benzyloxycarbonyl |

EXAMPLE 1

Synthetic Details for Compounds 1–114 Listed in Tables 1 and 2

The end product cyclic peptides disclosed in tables 1 and 2 (refer to Table 2 for the numbering system) were obtained by cyclisation of the corresponding precursor (generally linear) peptides disclosed in table 1. (Note however that the final amide bond can be formed between any amino acid or LINKER position to give the same cyclic peptide). The general procedure used for one of the compounds, c(Ile-Leu-Asp-Val-NH—(CH$_2$)$_5$—CO) (compound no. 3, table 2) is shown in FIG. 3 and is described below in detail. In the case of other compounds, only the variations from the standard procedure are mentioned.

1. Synthesis of c(Ile-Leu-Asp-Val-NH—(CH$_2$)$_5$—CO) (compound 3, FIG. 3)

The cyclic peptide was prepared by the solid phase procedure using 2-chlorotritylchloride resin. After assembling the partially protected linear peptide on the resin, the peptide was cleaved from the resin and used in the subsequent steps without any purification. However, the final product was purified extensively by reverse phase high pressure liquid chromatography (HPLC) before characterisation.

1.1 Preparation of c(Ile-Leu-Asp-Val-NH(CH$_2$)$_5$—CO) [compound 3] (Step 6, FIG. 3)

The protected cyclic peptide, c(Ile-Leu-Asp(OBu$^t$)-Val-NH(CH$_2$)$_5$—CO), (125 mg, 0.2 mmole) was treated for 30 minutes with a mixture of trifluoroacetic acid-water (95:5, 15 ml) and triisopropylsilane (200 μl) to remove the aspartic acid side chain protecting group. Evaporation to a small volume, followed by trituration with ether yielded the crude cyclic peptide (75 mg). The crude product was purified by preparative reverse phase HPLC on a Vydac 218TP1022 column using a gradient of acetonitrile-water containing 0.1% trifluoroacetic acid (15–55%) over a period of 65 minutes at a flow rate of 10.0 ml/minute. The product-containing fractions were combined and freeze dried to give the purified cyclic peptide (50 mg). The peptide [single peak on HPLC, retention time 18.03 minutes on a Novapak C$_{18}$ column using a gradient of acetonitrile-water containing 0.1%-trifluoroacetic acid (10–60%) over a period of 30 minutes at a flow rate of 1.0 ml/minute] was characterised by amino acid analysis and mass spectroscopy (table 2). The protected cyclic peptide starting material was prepared as follows.

1.2 Preparation of Fmoc-NH(CH$_2$)$_5$—COO-chlorotrityl resin (Step 1, FIG. 3)

2-Chlorotritylchloride resin (Nova Biochem.; 1.6 mmole Cl/g; 1 g) was swollen in dichloromethane (10 ml) (dried over molecular sieve) for 5 minutes. A solution of Fmoc-NH—(CH$_2$)$_5$—COOH (355 mg, 1 mmole) and diisopropylethylamine (560 μl, 3.2 mmole) in dichloromethane (5 ml) was added and the suspension was shaken mechanically for 45 minutes. Methanol (9 ml) and diisopropylethylamine (1 ml) were added and the shaking was continued for a further five minute period. The resin was collected by filtration and washed successively with dichloromethane, dimethylformamide, dichloromethane, isopropanol and ether, and finally dried at 50° C. in a vacuum oven (weight 1.33 g)

1.3 Preparation of Ile-Leu-Asp(OBu$^t$)-Val-NH(CH$_2$)$_5$—COO-chlorotrityl resin (Steps 2 and 3, FIG. 3)

The above resin was placed in a reaction vessel fitted with a sintered glass disc. The following series of reactions were then carried out manually to obtain the desired peptide resin.
(a) Removal of the Fmoc group with two treatments (1×5 minutes and 1×15 minutes) of 20% piperidine in dimethylformamide followed by five washes with dimethylformamide to remove excess reagents and cleavage products.
(b) Acylation with Fmoc-Val (678 mg, 2 mmole) activated with O-(benzotriazol-1-yl)-1,1,3,3-tetramethyluronium hexafluorophosphate (HBTU) (760 mg, 2 mmole) and diisopropylethylamine (700 μl, 4 mmole) in dimethylformamide (4 ml) for 1 hour. The resin was again washed five times with dimethylformamide to remove excess reagents. The above deprotection and coupling cycles were repeated using Fmoc-Asp(OBu$^t$)—OH (822 mg, 2 mmole), Fmoc-Leu-OH (700 mg, 2 mmole) and Fmoc-Ile-OH (700 mg, 2 mmole) to give Fmoc-Ile-Leu-Asp(OBu$^t$)-Val-NH(CH$_2$)$_5$—COO-chlorotrityl resin. The N-terminal Fmoc group was cleaved (step 3) with 20% piperidine in dimethylformamide (1×5 minutes and 1×15 minutes) and the peptide resin, Ile-Leu-Asp(OBu$^t$)-Val-NH(CH$_2$)$_5$—COO-chlorotrityl resin, was washed successively with dimethylformamide, dichloromethane and ether and dried in a vacuum oven at 50° C. (weight 1.51 g).

1.4 Preparation of Ile-Leu-Asp(OBu$^t$)-Val-NH(CH$_2$)$_5$—COOH, HCl. (Step 4, FIG. 3)

The peptide resin, Ile-Leu-Asp(OBu$^t$)-Val-NH(CH$_2$)$_5$—COO-chlorotrityl resin, was suspended in a mixture of acetic acid-trifluoroethanol-dichloromethane (2:2:6) (25 ml) for 2 hours. The resin was removed by filtration and washed with the above solvent mixture. The combined filtrates were evaporated and the residue triturated with ether to give Ile-Leu-Asp(OBu$^t$)-Val-NH(CH$_2$)$_5$—COOH as an acetate salt (428 mg), [M+H]$^+$628.4, [M+Na]$^+$650.5. The acetate salt was then converted to a hydrochloride salt by dissolving it in a mixture of water-acetonitrile (2:1, 60 ml), cooling to 0° C., adding 1.05 equivalents of 1N HCl and freeze drying the contents.

1.5 Preparation of c(Ile-Leu-Asp(OBu$^t$)-Val-NH(CH$_2$)$_5$—CO) (Step 5, FIG. 3)

A part of the above linear peptide hydrochloride, Ile-Leu-Asp(OBu$^t$)-Val-NH(CH$_2$)$_5$—COOH (HCl), (190 mg, 0.288 mmole) was dissolved in dimethylformamide (300 ml) and O-(benzotriazol-1-yl)-1,1,3,3-tetramethyluronium hexafluorophosphate (HBTU) (109 mg, 0.288 mmole), 1-hydroxybenzotriazole (45 mg, 0.288 mmole) and diisopropylethylamine (117 μl, 0.86 mmole) were added to the solution. The reaction mixture was stirred for 3 hours at room temperature and then evaporated to dryness in vacuum. The residue was partitioned between ethyl acetate and water. The organic layer was then washed successively with 1M citric acid, saturated sodium chloride, 10% sodium bicarbonate, and saturated sodium chloride, dried over magnesium sulphate and evaporated to dryness in vacuum. The product was collected and dried over P$_2$O$_5$/KOH to give the crude product [125 mg; retention time 20.71 minutes on a Vydac 218TP54 column using a gradient of acetonitrile-water containing 0.1% trifluoroacetic acid (20–80%) over a period of 30 minutes at a flow rate of 1.0 ml/minute] which was used in the final step (see 1.1) without any purification.

2. Syntheses of Compounds 1, 2 and 4

The three compounds were synthesised by the procedure used for compound 3 except that Fmoc-NH(CH$_2$)$_3$—COOH (for compound 1), Fmoc-NH(CH$_2$)$_4$—COOH (for compound 2) and Fmoc-NH(CH$_2$)$_7$—COOH (for compound 4) derivatives were first coupled to the 2-chlorotritylchloride resin in place of Fmoc-NH(CH$_2$)$_5$—COOH used in the case of compound 3.

3. Syntheses of Compounds 5–10

The compounds were synthesised by the procedure used for compound 3 except that Fmoc-D-Ile (for compound 5), Fmoc-D-Leu (for compound 6), Fmoc-Pro (for compound 7), Fmoc-Gly (for compound 8), Fmoc-t-butyl-glycine (for compound 9) or Fmoc-t-butyl-alanine (for compound 10), derivatives were used in place of Fmoc-Ile. Structures of t-butyl-glycine (t-leucine) and t-butyl-alanine (neopentylglycine) are shown in FIG. 5.

4. Synthesis of Compound 11

The procedure used for the synthesis of compound 11 is shown in FIG. 11.

4.1 Synthesis of

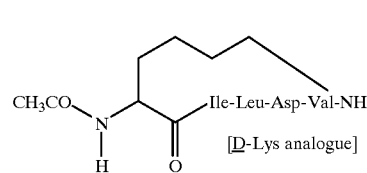

(Step 6, FIG. 11)

The crude cyclic peptide starting material was dissolved in a mixture of trifluoroacetic acid-water (95:5, 20 ml) and after adding triisopropylsilane (200 μl) the mixture was stirred at room temperature for 30 minutes. The solvent was evaporated off in vacuum and the crude product was purified by reverse phase HPLC to give the desired end product (yield 28 mg). The crude cyclic peptide starting material was prepared as follows.

4.2 Preparation of Z-D-Lys(Fmoc)-Ile-Leu-Asp(OBu$^t$)-Val-chlorotrityl resin (Step 1, FIG. 11).

Z-D-Lys(Fmoc)-Ile-Leu-Asp-Val was assembled on the chliorotrityl resin by a procedure similar to that described above for Ile-Leu-Asp(OBu$^t$)-Val-NH(CH$_2$)$_5$—COO-chlorotrityl resin used in the synthesis of compound 3 except that the resin was first reacted with Fmoc-Val in place of Fmoc-NH(CH$_2$)$_5$—COOH.

4.3 Preparation of Z-D-Lys-Ile-Leu-Asp(OBu$^t$)-Val, HCl. (Steps 2 and 3, FIG. 11)

By a procedure similar to that described above for the hydrochloride of Ile-Leu-Asp(OBu$^t$)-Val-NH(CH$_2$)$_5$—COOH, Z-D-Lys(Fmoc)-Ile-Leu-Asp(OBu$^t$)-Val-chlorotrityl resin was first treated with piperidine to cleave the Fmoc group and the peptide was then cleaved from the resin to give Z-D-Lys-Ile-Leu-Asp(OBu$^t$)-Val which was then converted to the hydrochloride salt.

4.4 Preparation of

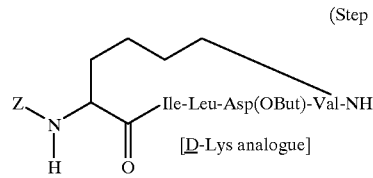

(Step 4, FIG. 11)

The linear peptide hydrochloride (236 mg, 0.291 mmole) was dissolved in dimethylformamide (350 ml) and after adding HBTU (110.5 mg, 0.291 mmole), HOBt (39.3 mg, 0.291 mmole) and diisopropylethylamine (152 μl, 0.873 mmole), the reaction mixture was stirred for two hours at room temperature. The solvent was removed in vacuum and the residue was partitioned between ethyl acetate and water. The organic phase was washed with 1N citric acid, saturated sodium chloride solution, 10% aqueous sodium hydrogen carbonate and saturated sodium chloride solution. The organic phase was then dried over magnesium sulphate and the solvent removed in vacuum. The crude product (retention time 25.24 min., Vydac column, 20–80% acetonitrile-water gradient over a period of 30 min.) was used in the next step without further purification.

4.5 Synthesis of (Step 5, FIG. 11)

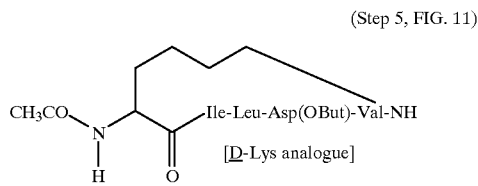

The crude cyclic peptide (157 mg, 0.207 mmole) was dissolved in a mixture of ethanol-water-acetic acid (40 ml/6 ml/10 ml) and Pd/C (about 200 mg) was added. Hydrogen gas was then bubbled through the stirred reaction mixture for a period of four hours to cleave the N-terminal benzyloxycarbonyl group. The catalyst was then removed by filtration and the filtrate was evaporated to dryness. The residue, dissolved in dimethylformamide (10 ml), was treated with an excess of acetic anhydride and the solution was left at room temperature for 16 hours. The solvent was removed in vacuo and the residue was collected with ether, washed with ether and used in step 6 (see 4.1).

5. Syntheses of Compounds 12, 13 and 14.

All of these compounds were prepared by procedures similar to those described above for compound 11. The structures of the corresponding linear peptides assembled on the resin are shown in table 1.

6. Synthesis of Compound 15

Compound 15 was synthesised by the procedure used for compound 3 except that N-Fmoc-aminomethylbenzoic acid was first coupled to the 2-chlorotritylchloride resin in place of Fmoc-NH(CH$_2$)$_5$—COOH used in the case of compound 3.

7. Synthesis of Compound 16 (FIG. 6)

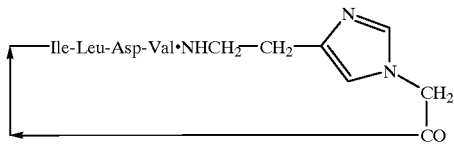

7.1 Preparation of Cyclic Peptide 16 (step 6, FIG. 6)

The linear peptide starting material was cyclised and deprotected by the procedures described above for c(Ile-Leu-Asp-Val-NH—(CH$_2$)$_5$—CO) in the equivalent steps in Example 1 (compound 3) to give the final cyclic peptide end product (16). The linear peptide starting material was prepared as follows.

7.2 Preparation of $N^\alpha$-Boc-Histamine (step 1, FIG. 6)

Di-tert-butyldicarbonate (24 g, 110 mmole) in methanol (50 ml) was added to a solution of histamine dihydrochloride (10 g, 54.3 mmole) and triethylamine (15.3 ml, 109 mmole) in methanol (100 ml) over 15 minutes with stirring. After stirring at room temperature for 24 hours, the solvent was removed by evaporation and the residue was partitioned between dichloromethane and water. The organic phase was washed twice with M citric acid solution and saturated sodium chloride solution, dried over MgSO$_4$ and evaporated to leave a solid. Recrystallisation from ethyl acetate gave $N^\alpha,N^\tau$-Boc-histamine [12.99 g, 76%, m.p. 125–126° C.; Thin layer chromatography on silica gel plates showed a single spot; R$_f$0.25 in ethyl acetate-isohexane (1:1) and 0.62 in methanol-chloroform (1:9)]. Diisopropylethylamine (1 ml) was added to a solution of $N^\alpha,N^\tau$-Boc-histamine (8.3 g, 26.7 mmole) in methanol (150 ml) and the solution was stirred at room temperature for 24 hours. The solvent was removed by evaporation and the residue was precipitated from ethyl acetate-isohexane [5.46 g, 97%, m.p. 93–95° C.; Thin layer chromatography on silica gel plates showed a single spot; R$_f$0.53 in acetonitrile-water (3:1), 0.23 in methanol-chloroform (1:9) and 0.73 in chloroform-methanol-water (55:40:10)].

7.3 Preparation of (step 2, FIG. 6)

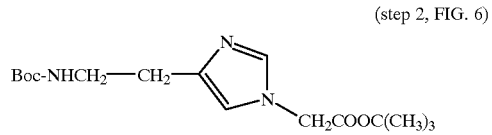

t-Butyl bromoacetate (2.31 g, 11.80 mmole) in dichloromethane (6 ml) was added to a stirred solution of $N^\alpha$-Boc-histamine (2.5 g, 11.8 mmole) and diisopropylethylamine (2.06 ml, 11.8 mmole) in dichloromethane (50 ml). The stirring was continued for 24 hours at room temperature. Additional dichloromethane (200 ml) was added and the solution was washed with M citric acid solution, saturated sodium chloride solution, dried over MgSO$_4$, and evaporated to dryness. The residual oil was used in the next step without further purification.

7.4 Preparation of (step 3, FIG. 6)

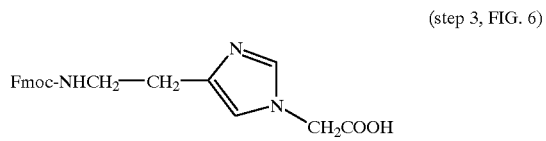

The above imidazole derivative was dissolved in trifluoroacetic acid:water (95:5; 100 ml) containing triisopropylsilane (1 ml) and left at room temperature for 90 minutes. The solvent was removed by evaporation under reduced pressure and the remaining oil was triturated with ether and dried under high vacuum over P$_2$O$_5$ and KOH to give a solid [3.9 g, (M+H)$^+$ 170, thin layer chromatography on silica gel plates showed a single spot; R$_f$0.35 in acetonitrile-water (3:1), and 0.37 in chloroform-methanol-water (55:40:10)].

The deprotected imidazole derivative (3.9 g, 14 mmole) was dissolved in water (50 ml), acetone (30 ml) and 1M sodium carbonate (30 ml) and the solution was cooled in an ice bath. 9-Fluorenylmethyl-N-hydroxysuccinimide (4.76 g) in acetone (30 ml) was added dropwise with stirring over a period of 20 minutes (pH maintained at 9 by the addition of 1M sodium carbonate solution) and the stirring was continued overnight. Acetone was removed by evaporation and the aqueous solution was acidified with 1M KHSO$_4$ and the product was extracted into ethyl acetate. The organic phase was washed with water and saturated sodium chloride solution, dried over MgSO$_4$, and evaporated to leave an oil. Trituration with ether and ether/isohexane gave a solid [3.66 g, 66%; (M+H)$^+$ 392].

7.5 Preparation of

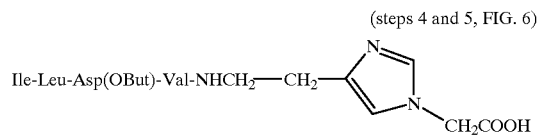

(steps 4 and 5, FIG. 6)

The Fmoc-histamine derivative (782 mg, 2 mmole) in dichloromethane (10 ml) and diisopropylethylamine (1.05 ml, 6 mmole) was added to 2-Chlorotritylchloride resin (Nova Biochem., 2 g) swollen in dichloromethane (25 ml) and the reaction mixture was shaken gently for 75 minutes. A 10% solution of diisopropylethylamine in methanol (20 ml) was added and the shaking was continued for 15 minutes. The resin was filtered off, washed successively with dichloromethane, dimethylformamide, dichloromethane, methanol and ether and dried at 50° C. in a vacuum oven for 16 hours (weight 2.16 g).

The above resin was placed in a reaction vessel fitted with a sintered glass disc and the tetrapeptide derivative was synthesised on the resin using standard methods (see equivalent steps in Example 1) (compound 3), then cleaved to give the desired linear peptide.

8. Synthesis of Compound 17

The synthetic route to compound 17 is shown in FIG. 12.

8.4. Synthesis of compound 17 (step 5, FIG. 12)

The linear peptide starting material was cyclised and deprotected by the procedures described above for c(Ile-Leu-Asp-Val-NH—(CH$_2$)$_5$—CO) in the equivalent steps in Example 1 (compound 3) to give the final cyclic peptide end product (17). The linear peptide starting material was prepared as set out below.

8.1. Synthesis of compound 17 (step 1, FIG. 12)

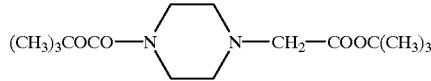

t-Butyl bromoacetate (4.88 g, 25 mmole) in dichloromethane (50 ml) was added to a solution of t-butyl-1-piperazine carboxylate (4.65 g, 25 mmole) and triethylamine (3.5 ml, 25 mmole) in dichloromethane (30 ml). The reaction mixture was stirred overnight, filtered to remove the solids separated overnight and the filtrate evaporated to dryness. The residue was partitioned between ethyl acetate and water, the organic layer was then washed with water, dried over MgSO$_4$ and evaporated to dryness. The residue was crystallised from ether-isohexane to yield the product (5.66 g, 75%, m.p. 99–100° C.). [Elemental analysis: Found C 59.8%, H 9,6%, N 9.1%; C$_{15}$H$_{28}$N$_2$O$_4$ requires C 60.0%, H 9.4%, N 9.33%]. [Thin layer chromatography on silica gel plates showed a single spot; R$_f$ 0.38 in ethyl acetate-isohexane (1:1) and 0.68 in methanol-chloroform (1:9)].

8.2. Synthesis of Compound 17 (step 2, FIG. 12)

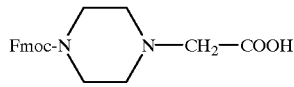

The compound described in section 8.1 (5 g, 16.6 mmole) was treated with a mixture of trifluoroacetic acid-water (95:5; 50 ml) for 1 hour. The acid was removed by evaporation in vacuum and the residual oil was triturated with ether to give a solid which was collected, washed with ether and dried over P$_2$O$_5$/KOH under vacuum (6.25 g, m.p. 177–182° C.). The solid was then dissolved in a mixture of water and acetone (1:1, 150 ml) containing potassium carbonate (6.92 g, 3 equivalents). 9-Fluorenylmethyl-N-hydroxysuccinimide (5.66 g, 16.7 mmole) in acetone (30 ml) was added over a period of 20 minutes with stirring. The pH of the solution was maintained at about 9 by the addition of M K$_2$CO$_3$ solution. After stirring overnight at room temperature, the acetone was removed by evaporation under vacuum and the aqueous solution was acidified with KHSO$_4$ solution. The product was extracted into ethyl acetate and the solution was washed with water (6 times) and with saturated NaCl solution. The organic layer was dried over MgSO$_4$ and evaporated to give an oil which solidified on trituration with isohexane and ether (yield 3.72 g, 60%). A sample was recrystallised from ethanol-ether, m.p. 179–182° C., (M+H)$^+$ 367.

8.3. Synthesis of compound 17 (steps 3 and 4, FIG. 12)

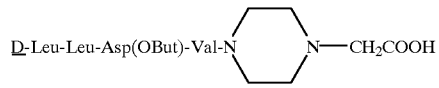

The above Fmoc-piperazine derivative (366 mg, 1 mmole) in dichloromethane (15 ml) and diisopropylethylamine (525 µl, 3 equivalents) were added to 2-chlorotritylchloride resin (Nova Biochem., 1 g) and the reaction mixture was shaken gently for 75 minutes. A 10% solution of diisopropylethylarnine in methanol (10 ml) was added and the shaking was continued for 10 minutes. The resin was filtered off, washed successively with dichloromethane, dimethylformamide, dichloromethane, ether and dried at 50° C. in a vacuum oven (weight 1.13 g).

The above resin was placed in a reaction vessel fitted with a sintered glass disc. The following series of reactions were then carried out manually to obtain the desired peptide resin.

(a) Removal of the Fmoc group with two treatments (1×5 minutes and 1×15 minutes) of 20% piperidine in dimethylformamide followed by five washes with dimethylformamide to remove excess reagents and cleavage products.

(b) Acylation with Fmoc-Val (678 mg, 2 mmole) activated with O-(benzotriazol-1-yl)-1,1,3,3-tetramethyluronium hexafluorophosphate (HBTU) (760 mg, 2 mmole) and diisopropylethylamine (700 µl, 4 mmole) in dimethylformamide (4 ml) for 1 hour. The resin was again washed five times with dimethylformamide to remove excess reagents. The above deprotection and coupling cycles were repeated using Fmoc-Asp(OBu$^t$)-OH (822 mg, 2 mmole), Fmoc-Leu-OH (700 mg, 2 mmole) and Fmoc-D-Leu-OH (700 mg, 2 mmole) to give the protected tetrapeptide derivative attached to the chlorotrityl resin (step 3). The N-terminal Fmoc group was cleaved with 20% piperidine in dimethylformamide (1×5 minutes and 1×15 minutes) and the peptide resin was washed successively with dimethylformamide; dichloromethane and ether and dried in a vacuum oven at 50° C.

The peptide resin was suspended in a mixture of acetic acid-trifluoroethanol-dichloromethane (2:2:6) (25 ml) for 2 hours. The resin was removed by filtration, washed with the above solvent mixture. The combined filtrates were evaporated and the residue triturated with ether to give the linear tetrapeptide derivative as an acetate salt. The acetate salt was then converted to a hydrochloride salt by dissolving it in a mixture of water-acetonitrile (2:1, 60 ml), cooling to 0° C., adding 1.05 equivalents of 1N HCl and freeze drying the contents.

9. Syntheses of Compounds 18 and 19.

Both of these compounds were synthesised by the procedures described above for compound 17. The linear peptides (structures shown in table 1) were cyclised and deprotected by the procedures described above for c(Ile-Leu-Asp-Val-NH—(CH$_2$)$_5$—CO) in the equivalent steps in Example 1 (compound 3) to give the final cyclic peptide end products (18 and 19).

10. Syntheses of Compounds 20 to 27.

All of these compounds were prepared by procedures similar to those described above for compound 11 (FIG. 11). The structures of the corresponding linear peptides assembled on the resin are shown in table 1.

11. Syntheses of Compounds 28 to 38.

The compounds were synthesised by the procedure used for compound 3 (FIG. 3). The first amino acid on the resin was aminohexanoic acid in the case of compounds 30–32 and aminovaleric acid in the case of compounds 28–29 and 33–38. The required linear peptides (amino acid sequences shown in table 1) were prepared by substituting Ile or Val residues in compound 3 by an amino acid present in the corresponding position in compounds 28–38. Structures of unnatural amino acids, [N-Me-Ala, N-Me-Ile, t-butylglycine (t-leucine) and t-butyl-alanine (neopentylglycine)), are shown in FIGS. 5 and 15.

12. Syntheses of Compounds 39 and 40

Compound 40 was prepared by a procedure similar to that described above for compound 11 (FIG. 11). The N-terminal benzyloxycarbonyl group was cleaved by the procedure described for the corresponding step in compound 11 to give compound 39.

13. Synthesis of compound 41.

The partially protected cyclic peptide containing an amino group at the N-terminus (structure shown below; used in the synthesis of compound 14) was synthesised by the route used for the synthesis of compound 11 (scheme 11).

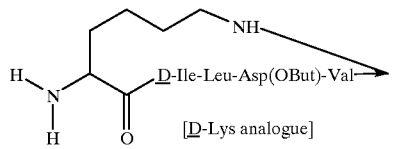

Propionic anhydride (72 μl, 0.563 mmole) was added to a solution of the above peptide (80 mg, 0.141 mmole) in dimethylformamide (7 ml). After stirring overnight at room temperature the solvent was evaporated off in vacuum and the residue purified by HPLC to give the desired peptide 41.

14. Syntheses of Compounds 42 and 43

Both these compounds were synthesised by the same method and using the same quantity of the intermediate peptide as described above for compound 41. In place of propionic anhydride, succinic anhydride (56.3 mg, 0.564 mmole) was used in the case of compound 42 and isovaleric anhydride (105 mg, 0.564 mmole) was used in the case of compound 43.

15. Synthesis of compound 44.

The partially protected cyclic peptide used in the synthesis of compound 44 (structure shown below) was synthesised by the same method as described for compound 11 (FIG. 11) except that Fmoc-D-Leu was used in place of Fmoc-Ile.

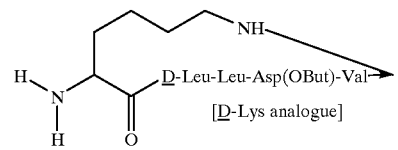

The above peptide (100 mg, 0.16 mmole) was dissolved in dimethylformamide (5 ml) and Fmoc-β-Ala (50 mg, 0.16 mmole), HBTU (60.7 mg, 0.16 mmole), HOBt (22 mg, 0.16 mmole) and diisopropylethylamine (83 μl, 0.48 mmole) were added and the reaction mixture stirred for 16 hours at room temperature. The solvent was evaporated off in vacuo and the crude peptide was deprotected (both Fmoc and OBu$^t$groups) and purified by the standard methods to give 44.

16. Synthesis of compound 45.

The precursor cyclic peptide.(deprotected at the N-terminal end) (100 mg) was dissolved in dimethylformamide (5 ml) and acetaldehyde (9 μl) was added. The mixture was stirred at room temperature for 5 minutes and sodium cyanoborohydride (11.1 mg) was then added along with a drop of acetic acid and the stirring was continued for 30 minutes. The solvent was then removed by evaporation and the crude product deblocked (to cleave the Asp t-butyl ester group) and purified by HPLC.

17. Synthesis of compound 46.

The precursor cyclic peptide (deprotected at the N-terminal end) (120 mg) was dissolved in dimethylformamide (10 ml) and benzaldehyde (20 μl) was added. The mixture was stirred at room temperature for 5 minutes and sodium cyanoborohydride (11.1 mg) was then added along with a drop of acetic acid and the stirring was continued for 30 minutes. The solvent was then removed by evaporation and the crude product deblocked (to cleave the Asp t-butyl ester group) and purified by HPLC.

18. Syntheses of compound 47, 48 and 49.

The above three compounds were synthesised by the same method and by using the same partially protected peptide intermediate as described above for compound 44. In place of Boc-β-Ala, 3-pyridylacetic acid, Fmoc-Glu(OBu$^t$) and pyroglutamic acid were used, respectively, for compounds 47, 48 and 49.

19. Syntheses of Compounds 50–53.

The above four compounds were synthesised by the procedure used for compound 3 except that Fmoc-NH-(CH$_2$)$_2$—COOH (for compound 50), Fmoc-NH(CH$_2$)$_4$—COOH (for compound 51), Fmoc-NH(CH$_2$)$_5$—COOH (for compound 52) and Fmoc-NH(CH$_2$)$_7$—COOH (for compound 53) derivatives were first coupled to the 2-chlorotritylchloride resin in place of Fmoc-NH(CH$_2$)$_5$—COOH used in the case of compound 3. The linear peptides (sequences in table 1) were then assembled on the resin and the desired cyclic peptides obtained by the standard procedures. Both the side chain Asp(OBu$^t$) and Glu(OBu$^t$) protecting groups were removed in the final deblocking step.

20. Synthesis of compound 54.

Compound 54 was synthesised by the procedure used for compound 3 except that Fmoc-NH(CH$_2$)$_2$—S—CH$_2$—COOH was first coupled to the 2-chlorotritylchloride resin in place of Fmoc-NH(CH$_2$)$_5$—COOH used in the case of compound 3. The linear peptide (sequence in table 1) was then assembled on the resin and the desired cyclic peptides obtained by the standard procedures.

Fmoc-NH(CH$_2$)$_2$—S—CH$_2$—COOH (used above) was obtained from 2-aminoethanethiol and 2-bromoacetic acid.

2-Aminoethanethiol hydrochloride (5.68 g, 50 mmole) was dissolved in water (200 ml) and sodium hydrogen carbonate (25.2 g, 300 mmole) was added to it. 2-Bromoacetic acid (6.95 g, 50 mmole) dissolved in acetonitrile (100 ml) was added in portions over 30 minutes to the stirred solution prepared above. After 1 hour at room temperature, a solution of 9-fluorenylmethyl-N-hydroxysuccinimide (Fmoc-OSu) (16.85 g, 50 mmole) in acetonitrile (150 ml) was added and the stirring was continued for 16 hours. The slightly turbid solution was evaporated to remove most of the acetonitrile and the remaining aqueous solution was extracted with ethyl acetate (3×50 ml) and acidified (pH 2) by the addition of hydrochloric acid. The white solid was collected, washed with water and dried in vacuo at 45° C. Yield 17 g (95%), $(M+H)^+$ 358.0.

21. Syntheses of Compounds 55 and 56.

Both these compounds were synthesised starting from by the procedure described for compound 3 (FIG. 1), except that $Fmoc-NH(CH_2)_4$—COOH was first coupled to the 2-chlorotritylchloride resin in place of $Fmoc-NH(CH_2)_5$—COOH used in the case of compound 3. The linear peptides (sequences shown in table 1) were assembled and the cyclic peptides obtained by the standard procedures.

22. Synthesis of compound 57.

The parent cyclic peptide (compound 54, 266 mg) was dissolved in a mixture of water-acetonitrile (1:1, 50 ml) and hydrogen peroxide (150 μl) was added to the stirred solution in five equal parts over a period of five days. The solvent was then removed by evaporation and the residue was purified by high pressure liquid chromatography to give the product (140 mg).

23. Synthesis of compound 58.

Compound 58 was synthesised by the procedure used for compound 3 except that $Fmoc-NH(CH_2)_2$—S—$(CH_2)_2$—COOH was first coupled to the 2-chlorotritylchloride resin in place of $Fmoc-NH(CH_2)_5$—COOH used in the case of compound 3. The linear peptide (sequence in table 1) was then assembled on the resin and the desired cyclic peptides obtained by the standard procedures. $Fmoc-NH(CH_2)_2$—S—$(CH_2)_2$—COOH was obtained by the procedure described above for $Fmoc-NH(CH_2)_2$—S—$CH_2$—COOH (synthesis of compound 54) by using 3-bromopropionic acid and 2-aminoethanethiol. $(M+H)^+$ 372.

24. Syntheses of Compounds 59–69

The compounds were synthesised by the procedures described above for compound 3. The linear peptides (structures shown in table 1) were synthesised on the resin, cyclised by the standard procedures, deprotected and purified by HPLC to give the final cyclic peptide end products 59–69.

25. Synthesis of compound 70

The linear peptide required for the synthesis of this compound (table 1) was prepared by coupling Fmoc-isoglutamine to Ile-Leu-Asp(OBu$^t$)-Val-OTrt resin. The tetrapeptide resin was prepared in the usual way (compound 3) starting from 2-chlorotritylchloride resin. The linear peptide was then cyclised, deprotected and purified in the standard manner to give cyclic peptide 70.

26. Syntheses of Compounds 71–77

The compounds were synthesised by the procedures described above for compound 3. The linear peptides (structures shown in table 1) were synthesised on the resin, cyclised by the standard procedures, deprotected and purified by HPLC to give the final cyclic peptide end products 71–77.

27. Syntheses of Compounds 78 and 79.

Both of these compounds were synthesised by the procedures described above for compound 17 (FIG. 12). The linear peptides (structures shown in table 1) were synthesised on the resin, cyclised by the standard procedures, deprotected and purified by HPLC to give the final cyclic peptide end products 78 and 79.

28. Synthesis of compound 80.

The linear peptide required for the synthesis of this peptide (table 1) was assembled on the 2-chlorotritylchloride resin. 3-Bromopropionic acid was reacted with the resin in a manner similar to that described in example 1 (compound 3) for $Fmoc-NH(CH_2)_5$—COOH. A five-fold excess of piperazine was then added to the 3-bromopropionyl-O-(2-chlorotrityl)-resin to give piperazine-N-propionyl derivative linked to the resin (structure shown below)

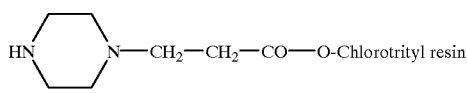

The linear peptide was then assembled on the resin, cleaved and cyclised by the procedures described for compound 11 (FIG. 11). The N-terminal benzyloxycarbonyl group was removed by catalytic hydrogenolysis (using 5% Pd/C) by using the procedure described for the corresponding step in compound 11. The N-terminal amino group was then acetylated by reacting the cyclic peptide with acetic anhydride in dimethylformamide. Cleavage of the Asp(OBu$^t$) group followed by purification of the crude peptide by HPLC gave the desired cyclic compound 80.

29. Synthesis of compound 81.

Compound 81 was synthesised by the procedures described above for compound 16 (FIG. 6). The linear peptide (structures shown in table 1) was synthesised on the resin, cyclised by the standard procedure, deprotected and purified by HPLC to give the final cyclic peptide end product.

30. Synthesis of compound 82.

An analogue of compound 11 containing a benzyloxycarbonyl group at the N-terminus and a D-leucine residue in place of Ile (structure shown below) was synthesised by the same method as described for compound 11 (FIG. 11).

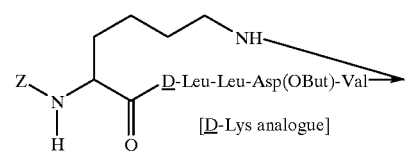

The N-terminal benzyloxycarbonyl group was cleaved by the same method and the resulting compound (350 mg, 0.56 mmole) was dissolved in dimethylformamide (15 ml)-2-Bromoacetic acid (86 mg) was then added followed by diisopropylcarbodiimide (97 μl). After 16 hours at ambient temperature, piperazine (5-fold excess) was added and the reaction mixture was kept at ambient temperature for further 24 hours. The solvent was evaporated off in vacuo and the crude peptide was deprotected and purified by the standard methods.

31. Syntheses of Compounds 83 and 84.

The D-Lys-D-Leu containing cyclic peptide [structure shown above (synthesis of compound 82)] was treated with trifluoroacetic acid for 30 minutes to give the fully deprotected cyclic peptide (structure shown below) which was used in the preparation of 83 and 84.

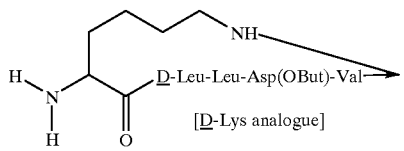

[D-Lys analogue]

For the synthesis of peptide 83, Boc-4-aminobutyric acid (55 mg) was dissolved in dimethylformamide (2 ml) and reacted with diisopropylcarbodiimide (41 μl) and HOAt (36 mg). After 30 minutes at ambient temperature, the reaction mixture was added to a solution of the above cyclic peptide (177 mg, 0.26 mmole) and diisopropylethylamine (92 μl) in DMF (10 ml) and the mixture was stirred for 6 hours at ambient temperature. The solvent was then vaporated off in vacuo and the residue was treated with trifluoroacetic acid to cleave the N-terminal Boc group and the crude peptide was purified (HPLC) to give pure 83. Cyclic peptide 84 was prepared by the same procedure as compound 83, except that Nα-Boc-Arg(HCl) was used in place of Boc-4-aminobutyric acid.

32. Syntheses of Compounds 85 to 89.

The compounds 85 to 89 were synthesised by the procedures used in the case of compound 17 (FIG. 7). The structures of the linear peptides assembled on the resin are shown in table 1.

33. Syntheses of Compounds 90 to 105.

The compounds were synthesised by the procedures described above for compound 3. The linear peptides (structures shown in table 1) were synthesised on the 2-chlorotritylchloride resin, cyclised by the standard procedures, deprotected and purified by HPLC to give the final cyclic peptide end products 90–105. In the compounds containing a D-Arg residue (90, 91, 97, 98, 101, 102 and 103), the arginine residue was incorporated by using the Fmoc-Arg(Pmc) derivative (FIG. 14). During the final deprotection procedure using trifluoroacetic acid, some partially protected compounds (106–109; still containing Pmc group) were also isolated and characterised by the normal methods.

34. Syntheses of Compounds 110 to 114.

The above cyclic peptides were prepared by reacting the cyclic peptide c(MeIle-Leu-Asp-Val-D-Orn-D-Ala) (92) or c(MeIle-Leu-Asp-Val-D-Lys-D-Lys) (95) with the required aldehyde or ketone and sodium cyanoborohydride. For example, compound 111 was prepared by dissolving the cyclic peptide 92 (64 mg, 100 μmole) in dry acetone (2 ml) and reacting with sodium cyanoborohydride (63 mg, 10 equivalents). After an hour, the reaction mixture was evaporated to dryness and the residue, dissolved in water (5 ml), was acidified with acetic acid and evaporated under high vacuum. The crude peptide was purified by HPLC.

EXAMPLE 2

In Vitro and In Vivo Assays

The following abbreviations and sources of materials are used in this example. MOLT-4—cells -lymphocytic T cell line (ATCC derived) Fibronectin—Reagent grade human fibronectin. Purified from human plasma by gelatin-sepharose affinity chromatography. Source: Bio Products Elstree UK. Product No. 9136. A review article on fibronectins is Fibronectins—Adhesive Glycoproteins of Cell Surface and Blood, K. M. Yamada and K. Olden, Nature, 275 (1978) 179–184. rsVCAM-1-(Reference source: Biochem Biophys Res Comm 1991 178 N3; 1498–1504). VCAM-1 is a cell surface glycoprotein produced by the vascular endothelium, as well as on macrophage-like and dandritic cell types, in response to certain inflammatory stimuli. VCAM-1 interacts with the integrin VLA-4 present on mononuclear leukocytes.

The cDNA for VCAM-1 was isolated by screening a cDNA library from IL-1β-activated human endothelial cells. Large quantities of the protein were expressed in insect cells using a baculovirus expression system. VCAM-1 expressing cells were shown to bind specifically to a variety of VLA-4 expressing cell lines (Jurkat, THP-1, U937).

Another reference on VCAM-1 is Expression and Functional Characterisation of Recombinant Human Vascular Cell Adhesion Molecule-1 (VCAM-1) Synthesised by Baculovirus-Infected Insect Cells, J. K. Stoltenborg, R. A. Straney, R. J. Tritch, W. M. Mackin and H. J. George, Protein Expression and Purification, 4 (1993) 585–593.

RPMI 1640—Cell media. Source Gibco BRL (Life technologies; Cat No 31870-025). FCS—Foetal calf serum. Source Advanced protein products (West Midlands UK) Cat No AS-302-50.

BCECF-AM—2',7'-bis (2 carboxyethyl)-5-(ε6)-carboxyfluoroscein acetoxymethyl ester). source: Molecular Probes Inc USA; Cat No B-1150.

CHO DG44—Chinese hamster ovary cell line (ATCC derived; Reference: Som Cell Mol Gen 1986; 12; 555–666)

DMEM—Dulbecco's modified eagle medium. Source Gibco BRL (Life technologies; Cat No 41966-029.

Antibiotic—Penicillin-steptomycin. Source Gibco BRL (Life Technologies; Cat No 15070-022).

Fluorskan™—is a fluorimeter.

HUVEC—Human umbilical cord endothelial cells. Primary cultures prepared from tissue samples. (Reference: J Clin Invest. 1973 52; 2745–2747.

Recombinant human TNFα—Tumor necrosis factor. Alzet osmotic minipump—Subcutaneous implanted micro osmotic pump, Alza Corporation Palo Alto, Calif.

2.1 MOLT-4 cell/Fibronectin-VCAM-1 Adhesion Assay.

The MOLT-4 cell/Fibronectin-VCAM-1 adhesion assay is used to investigate the interaction of the integrin VLA4 (Very Late Antigen, α4/β1) expressed on the MOLT-4 cell membrane with fibronectin or recombinant soluble VCAM-1 (rsVCAM-1). Fibronectin or rsVCAM-1 are coated overnight at 4° C. onto polystyrene 96-well microtitre plates at concentrations of 20 μg/ml and 1 μg/ml respectively. Following this, a concentrated BSA solution (10 mg/ml) is added to block non-specific binding sites. After aspiration of these solutions, equal volumes of compound and MOLT-4 cell suspension (1×10E6 cells/ml) are added. Adhesion takes place during a 2 hour incubation at 37° C., non or loosely adherent cells are removed by gentle agitation followed by vacuum aspiration. Quantitation of the remaining adherent cells is by means of a calorimetric assay of acid phosphatase activity, which is read on a spectrophotometer. Compounds which inhibit adhesion result in a lower absorbance reading. Standard, control and test conditions are assayed in triplicate, percentage inhibition being calculated with respect to total (no inhibitor) and non-specific (no fibronectin) standards on each plate.

2.2 Cell—Cell Assays 2.2.1. VCAM-1 CHO cells

MOLT-4 cells (RPMI 1640 supplemented with 5% FCS and 2mM L-Glutamine) are labelled with the fluorescent dye BCECF-AM (30 μg/ml per 3×10E6 cells). CHO DG44 transfected with full length VCAM-1 cDNA were selected for VCAM-1 expression by FACS analysis and grown to confluence in 96 well tissue culture plates. Prior to use in the adhesion assay CHO DG44 cells are washed three times (DMEM supplemented with 5% FCS, 2 mM L-Glutamine and 2% antibiotic). MOLT-4 (10E5 cell/well) cells are over laid on the VCAM-1 expressing CHO cells and incubated for 30 minutes at 37° C., 5% $CO_2$. The non-adherent cells are removed by washing the plate three times (RPMI 1640 supplemented with 5% FCS and 2 mM L-Glutamine) following which the plates are blotted dry on tissue paper. 100 μl of 2% Triton X-100 is added to each well and the plates read using a Fluoroskan (excitation=485 nM, emission=538 nM). Compounds are dissolved in appropriate solvents and added to the MOLT-4 cells prior to addition to HUVEC cultures, inhibition of adhesion is calculated comparing level of adhesion (fluorescence) of control vehicle treated cells with compound treated cells.

2.2.2 Human Umbilical Vein Endothelial Cells.

MOLT-4 cells (RPMI 1640 supplemented with 5% FCS and 2 mM L-Glutamine) are labelled with the fluorescent dye BCECF-AM (30 μg/ml per 3×10E6 cells). Primary HUVEC are grown to confluence in 96 well tissue culture plates and incubated for 18 hours with 2 U/ml recombinant human TNFα. Prior to use in the adhesion assay the primary HUVEC monolayers are washed (M199 supplemented with 5% FCS, 2 mM L-Glutamine and 2% antibiotic). MOLT-4 (10E5cell/well) cells are overlaid on the primary HUVEC and incubated for 30 minutes at 37° C., 5% $CO_2$. The non-adherent cells are removed by washing the plate three times (RPMI 1640 supplemented with 5% FCS and 2 mM L-Glutamine) and dried by blotting on tissue paper. 100 μl of 2% Triton X-100 is added to each well and the plates read using a Fluoroskan (excitation=485 nM, emission=538 nM). Compounds are dissolved in appropriate solvents and added to the MOLT-4 cells prior to addition to HUVEC cultures, inhibition of adhesion is calculated comparing level of adhesion (fluorescence) of control vehicle treated cells with compound treated cells.

2.3 In Vivo Contact hypersensitivity Response.

Balb/C male mice (20–25 g) are sensitised with oxazolone (50 μl of 0.24% in acetone/olive oil) by topical application to the shaved skin area of the back. Seven days later the mice are challenged by topical application of oxazolone (25 μl of 0.25% in acetone/olive oil) to the surface of the ear. Swelling of the ear develops over a 24 hour period following which ear thickness is measured and compared to the pre-challenge thickness, the percentage increase in ear thickness is calculated. Compounds are delivered via Alzet osmotic minipump daily dosing (once/day) which are implanted 24 hours prior to the oxazolone challenge, inhibition of the inflammatory response is calculated comparing vehicle treated animals and compound treated groups (n=6 animals per group).

2.4 In Vivo Ovalbumin Delayed type Hypersensitiivity Model.

Balb/C female mice (20–25 g) are immunised on the flank with an emulsion of ovalbumin (Sigma; 0.1 ml subcutaneous injection of 2 mg/ml solution mixed (1:1) with complete Freunds adjuvant; Difco). Seven days later the mice are challenged by subplantar injection of ovalbumin (30 μl of 1% heat aggregated ovalbumin in saline) into the left hind foot pad. Swelling of the foot develops over a 24 hour period following which foot pad thickness is measured and compared to the pre-challenge thickness, the percentage increase in in foot pad thickness is calculated. Compounds are delivered via Alzet osmotic minipump daily dosing (once/day) which are implanted 24 hours prior to the ovalbumin challenge and the inhibition of the inflammatory response is calculated comparing vehicle treated animals and compound treated groups (n=5 animals per group).

2.5 In Vivo Antigen Induced Arthritis Model.

Mice are immunised and boosted 7 days later with a combination of 100 μg methylated BSA in complete Freund's adjuvant (s.c.) followed by an intraperitoneal injection of bordetella pertussis organisms. Two weeks after boost animals are challenged with 100 μg methylated-bovine serum albumin (BSA) intra-articularly and the degree of inflammation/arthritis determined by measuring knee joint swelling, histology and changes in acute phase proteins. Compounds are dosed for 7 to 14 days commencing the day prior to challenge and the degree of inflammation/arthritis compared with the control animals and contralateral knee.

2.6 Experimental Autoimmune Encephalomyelitis Model.

Disease induced by s.c. injection of a mixture of spinal cord homogenate, myelin basic protein (MBP) or encephalogenic peptides with complete Freund's adjuvant (CFA), coupled with an i.p. injection of pertussis toxin. For acute disease, pertussis injection is repeated 2 days after immunisation. For chronic disease, pertussis is omitted and mice receive two injections of antigen in CFA, with an interval of 7 days. Disease is assessed by clinical scoring supported by histology. Compounds are dosed for 7 to 14 days commencing the day prior to challenge and the symptoms compared with the control animals.

Notes on Tables 1 and 2

For the sake of clarity each compound listed in the Tables has been given a different number. However some compounds with different numbers are in fact the same compound; these are listed below.

92=224=225=226=227
95=228
155=156=157=161
158=159=160=162=163=196=197=198
54=171

TABLE 1

Synthesis and purification of cyclic peptides

| NO: | Precursor | SEQ ID NO: | End Product Cyclic Peptide | High Pressure Liquid Chromatography (HPLC) (Gradient system and time) |
|---|---|---|---|---|
| 115 | Ile-Leu-Asp(OBu$^t$)-Val-NH(CH$_2$)$_3$-COOH | 1 | c[Ile-Leu-Asp-Val-NH-(CH$_2$)$_3$-CO] | 15–55% water-acetonitrile (65 min.) |
| 116 | Ile-Leu-Asp(OBu$^t$)-Val-NH(CH$_2$)$_4$-COOH | 2 | c[Ile-Leu-Asp-Val-NH-(CH$_2$)$_4$-CO] | 15–55% water-acetonitrile (65 min.) |
| 117 | Ile-Leu-Asp(OBu$^t$)-Val-NH(CH$_2$)$_5$-COOH | 3 | c[Ile-Leu-Asp-Val-NH-(CH$_2$)$_5$-CO] | 15–55% water-acetonitrile (65 min.) |
| 118 | Ile-Leu-Asp(OBu$^t$)-Val-NH(CH$_2$)$_7$-COOH | 4 | c[Ile-Leu-Asp-Val-NH-(CH$_2$)$_7$-CO] | 20–55% water-acetonitrile (65 min.) |
| 119 | D-Ile-Leu-Asp(OBu$^t$)-Val-NH-(CH$_2$)$_5$-COOH | 5 | c[D-Ile-Leu-Asp-Val-NH-(CH$_2$)$_5$-CO] | 15–55% water-acetonitrile (65 min.) |
| 120 | D-Leu-Leu-Asp(OBu$^t$)-Val-NH-(CH$_2$)$_5$-COOH | 6 | c[D-Leu-Leu-Asp-Val-NH-(CH$_2$)$_5$-CO] | 15–55% water-acetonitrile (65 min.) |
| 121 | Pro-Leu-Asp(OBu$^t$)-Val-NH-(CH$_2$)$_5$-COOH | 7 | c[Pro-Leu-Asp-Val-NH(CH$_2$)$_5$CO] | 10–40% water-acetonitrile (60 min.) |
| 122 | Gly-Leu-Asp(OBu$^t$)-Val-NH-(CH$_2$)$_5$-COOH | 8 | c[Gly-Leu-Asp-Val-NH(CH$_2$)$_5$CO] | 5–25% water-acetonitrile (60 min.) |
| 123 | t-Leu-Leu-Asp(OBu$^t$)-Val-NH-(CH$_2$)$_5$-COOH | 9 | c[t-Leu-Leu-Asp-Val-NH(CH$_2$)$_5$CO] | 15–55% water-acetonitrile (65 min.) |
| 124 | t-ButylAla-Leu-Asp(OBu$^t$)-Val-NH-(CH$_2$)$_5$-COOH | 10 | c[t-ButylAla-Leu-Asp-Val-NH(CH$_2$)$_5$CO] | 15–55% water-acetonitrile (65 min.) |
| 125 | Z-D-Lys-Ile-Leu-Asp(OBu$^t$)-Val-OH | 11 | c[Ac-D-Lys-Ile-Leu-Asp-Val] [D-Lys analogue] | 15–55% water-acetonitrile (65 min.) |

TABLE 1-continued

Synthesis and purification of cyclic peptides

| NO: | Precursor | SEQ ID NO: | End Product Cyclic Peptide | High Pressure Liquid Chromatography (HPLC) (Gradient system and time) |
|---|---|---|---|---|
| 126 | Z-D-Orn-Ile-Leu-Asp(OBu$^t$)-Val-OH | 12 | cyclic[Ac-D-Orn-Ile-Leu-Asp-Val] [D-Orn analogue] | 15–55% water-acetonitrile (65 min.) |
| 127 | Z-Orn-Ile-Leu-Asp(OBu$^t$)-Val-OH | 13 | cyclic[Ac-Orn-Ile-Leu-Asp-Val] [L-Lys analogue] | 15–55% water-acetonitrile (65 min.) |
| 128 | Z-D-Lys-D-Ile-Leu-Asp(OBu$^t$)-Val-OH | 14 | cyclic[Ac-D-Lys-D-Ile-Leu-Asp-Val] [D-Lys analogue] | 15–55% water-acetonitrile (65 min.) |
| 129 | Ile-Leu-Asp(OBu$^t$)-Val-N(H)-CH$_2$-C$_6$H$_4$-COOH | 15 | cyclic[Ile-Leu-Asp-Val-NH-CH$_2$-C$_6$H$_4$-CO] | 15–45% water-acetonitrile (65 min.) |
| 130 | Ile-Leu-Asp(OBu$^t$)-Val-NHCH$_2$-(imidazole)-CH$_2$-COOH | 16 | cyclic[Ile-Leu-Asp-Val-NHCH$_2$-(imidazole)-CH$_2$-CO] | 10–40% water-acetonitrile (60 min.) |

TABLE 1-continued

Synthesis and purification of cyclic peptides

| NO: | Precursor | SEQ ID NO: | End Product Cyclic Peptide | High Pressure Liquid Chromatography (HPLC) (Gradient system and time) |
|---|---|---|---|---|
| 131 | D-Leu-Leu-Asp(OBut)-Val- | 17 | 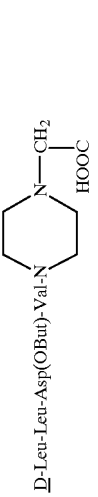 | 10–40% water-acetonitrile (60 min.) |
| 132 | bAla-Ile-Leu-Asp(OBut)-Val- | 18 | 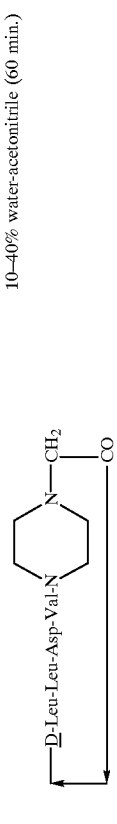 | 10–40% water-acetonitrile (60 min.) |
| 133 | bAla-D-Leu-Leu-Asp(OBut)-Val- | 19 | 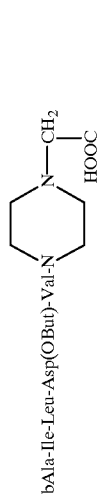 | 10–40% water-acetonitrile (60 min.) |
| 134 | Z-Lys-Ile-Leu-Asp(OBut)-Val-OH | 20 | 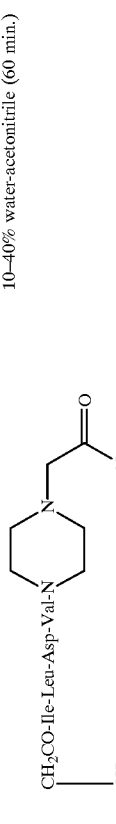 [L-Lys analogue] | 10–40% water-acetonitrile (65 min.) |
| 135 | Z-Orn-D-Ile-Leu-Asp(OBut)-Val-OH | 21 | 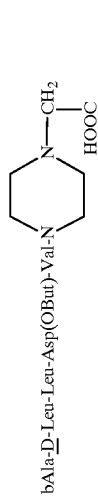 [L-Orn analogue] | 15–55% water-acetonitrile (65 min.) |
| 136 | Z-D-Orn-D-Ile-Leu-Asp(OBut)-Val-OH | 22 | 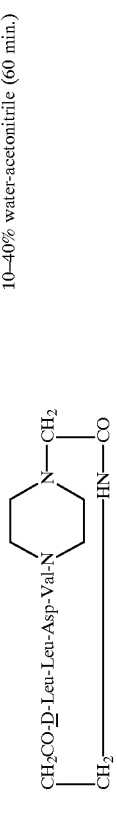 [D-Orn analogue] | 10–40% water-acetonitrile (65 min.) |

TABLE 1-continued

Synthesis and purification of cyclic peptides

| NO: | Precursor | SEQ ID NO: | End Product Cyclic Peptide | High Pressure Liquid Chromatography (HPLC) (Gradient system and time) |
|---|---|---|---|---|
| 137 | Z-Lys-D-Ile-Leu-Asp(OBu$^t$)-Val-OH | 23 | 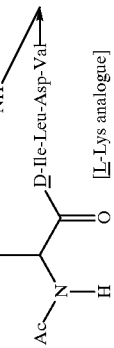 [L-Lys analogue] | 15–55% water-acetonitrile (65 min.) |
| 138 | Z-Dab-D-Ile-Leu-Asp(OBu$^t$)-Val | 24 | 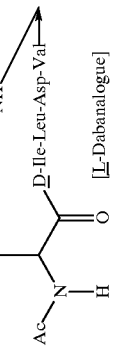 [L-Dab analogue] | 15–55% water-acetonitrile (65 min.) |
| 139 | Z-Dab-Ile-Leu-Asp(OBu$^t$)-Val | 25 | 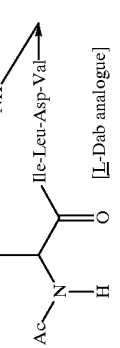 [L-Dab analogue] | 15–55% water-acetonitrile (65 min.) |
| 140 | Z-D-Dab-Ile-Leu-Asp(OBu$^t$)-Val | 26 | 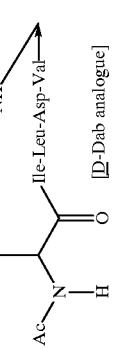 [D-Dab analogue] | 15–55% water-acetonitrile (65 min.) |
| 141 | Z-D-Dab-D-Leu-Leu-Asp(OBu$^t$)-Val | 27 | 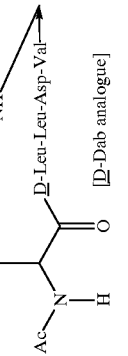 [D-Dab analogue] | 15–55% water-acetonitrile (65 min.) |
| 142 | D-Ile-Leu-Asp(OBu$^t$)-Val-NH-(CH$_2$)$_4$-COOH | 28 |  | 15–55% water-acetonitrile (65 min.) |

TABLE 1-continued

Synthesis and purification of cyclic peptides

| NO: | SEQ ID NO: | Precursor | End Product Cyclic Peptide | High Pressure Liquid Chromatography (HPLC) (Gradient system and time) |
|---|---|---|---|---|
| 143 | 29 | D-Leu-Leu-Asp(OBu$^t$)-Val-NH-(CH$_2$)$_4$-COOH | D-Leu-Leu-Asp-Val-NH(CH$_2$)$_4$CO (cyclic) | 15–55% water-acetonitrile (65 min.) |
| 144 | 30 | D-Val-Leu-Asp(OBu$^t$)-Val-NH-(CH$_2$)$_5$-COOH | D-Val-Leu-Asp-Val-NH(CH$_2$)$_5$CO (cyclic) | 15–40% water-acetonitrile (60 min.) |
| 145 | 31 | MeAla-Leu-Asp(OBu$^t$)-Val-NH-(CH$_2$)$_5$-COOH | MeAla-Leu-Asp-Val-NH(CH$_2$)$_5$CO (cyclic) | 10–40% water-acetonitrile (60 min.) |
| 146 | 32 | MeLeu-Leu-Asp(OBu$^t$)-Val-NH-(CH$_2$)$_5$-COOH | MeLeu-Leu-Asp-Val-NH(CH$_2$)$_5$CO (cyclic) | 10–40% water-acetonitrile (60 min.) |
| 147 | 33 | Ile-t-but-Ala-Asp(OBu$^t$)-Val-NH-(CH$_2$)$_4$-COOH | Ile-t-but-Ala-Asp-Val-NH(CH$_2$)$_4$CO (cyclic) | 15–55% water-acetonitrile (65 min.) |
| 148 | 34 | Ile-Ile-Asp(OBu$^t$)-Val-NH-(CH$_2$)$_4$-COOH | Ile-Ile-Asp-Val-NH(CH$_2$)$_4$CO (cyclic) | 15–55% water-acetonitrile (65 min.) |
| 149 | 35 | Ile-Nle-Asp(OBu$^t$)-Val-NH-(CH$_2$)$_4$-COOH | Ile-Nle-Asp-Val-NH(CH$_2$)$_4$CO (cyclic) | 15–55% water-acetonitrile (65 min.) |
| 150 | 36 | Ile-Val-Asp(OBu$^t$)-Val-NH-(CH$_2$)$_4$-COOH | Ile-Val-Asp-Val-NH(CH$_2$)$_4$CO (cyclic) | 15–55% water-acetonitrile (65 min.) |
| 151 | 37 | Ile-Cha-Asp(OBu$^t$)-Val-NH-(CH$_2$)$_4$-COOH | Ile-Cha-Asp-Val-NH(CH$_2$)$_4$CO (cyclic) | 15–55% water-acetonitrile (65 min.) |
| 152 | 38 | Ile-tert-Leu-Asp(OBu$^t$)-Val-NH-(CH$_2$)$_4$-COOH | Ile-tert-Leu-Asp-Val-NH(CH$_2$)$_4$CO (cyclic) | 15–55% water-acetonitrile (65 min.) |

TABLE 1-continued

Synthesis and purification of cyclic peptides

| NO: | Precursor | SEQ ID NO: | End Product Cyclic Peptide | High Pressure Liquid Chromatography (HPLC) (Gradient system and time) |
|---|---|---|---|---|
| 153 | | 39 | [cyclic peptide with D-Ile-Leu-Asp-Val and D-Lys] | 10–50% water-acetonitrile (65 min.) |
| 154 | Z-Lys-D-Ile-Leu-Asp(OBu)-Val | 40 | [cyclic peptide with D-Ile-Leu-Asp-Val and D-Lys analogue] | 15–55% water-acetonitrile (65 min.) |
| 155 | [structure with D-Ile-Leu-Asp(OBut)-Val and D-Lys] | 41 | [cyclic peptide with CH₃-C(O)-NH- modification, D-Ile-Leu-Asp-Val and D-Lys analogue] | 15–55% water-acetonitrile (65 min.) |
| 156 | [structure with D-Ile-Leu-Asp(OBut)-Val and D-Lys] | 42 | [cyclic peptide with COOH modification, D-Ile-Leu-Asp-Val and D-Lys analogue] | 10–40% water-acetonitrile (65 min.) |
| 157 | [structure with D-Ile-Leu-Asp(OBut)-Val and D-Lys] | 43 | [cyclic peptide with H₃C-CH(CH₃)- modification, D-Ile-Leu-Asp-Val and D-Lys analogue] | 15–55% water-acetonitrile (65 min.) |

TABLE 1-continued
Synthesis and purification of cyclic peptides
| NO: | Precursor | SEQ ID NO: | End Product Cyclic Peptide | High Pressure Liquid Chromatography (HPLC) (Gradient system and time) |
|---|---|---|---|---|
| 158 |  | 44 |  | 15–55% water-acetonitrile (65 min.) |
| 159 |  | 45 |  | 15–55% water-acetonitrile (65 min.) |
| 160 |  | 46 |  | 15–55% water-acetonitrile (65 min.) |
| 161 |  | 47 |  | 15–55% water-acetonitrile (65 min.) |

TABLE 1-continued

Synthesis and purification of cyclic peptides

| NO: | Precursor | SEQ ID NO: | End Product Cyclic Peptide | High Pressure Liquid Chromatography (HPLC) (Gradient system and time) |
|---|---|---|---|---|
| 162 | H-N(H)-[D-Lys]-C(=O)-D-Leu-Leu-Asp(OBu$^t$)-Val-NH-(end) | 48 | Glu-N(H)-[D-Lys analogue]-C(=O)-D-Leu-Leu-Asp-Val-NH- | 15–55% water-acetonitrile (65 min.) |
| 163 | H-N(H)-[D-Lys]-C(=O)-D-Leu-Leu-Asp(OBu$^t$)-Val-NH- | 49 | Pyr-N(H)-[D-Lys analogue]-C(=O)-D-Leu-Leu-Asp-Val-NH- | 15–55% water-acetonitrile (65 min.) |
| 164 | Glu(OBu$^t$)-Ile-Leu-Asp(OBu$^t$)-Val-Pro-NH-(CH$_2$)$_2$-COOH | 50 | c(Glu-Ile-Leu-Asp-Val-Pro-NH-(CH$_2$)$_2$-CO) | 10–50% water-acetonitrile (60 min.) |
| 165 | Glu(OBu$^t$)-Ile-Leu-Asp(OBu$^t$)-Val-Pro-NH-(CH$_2$)$_4$-COOH | 51 | c(Glu-Ile-Leu-Asp-Val-Pro-NH-(CH$_2$)$_4$-CO) | 10–50% water-acetonitrile (60 min.) |
| 166 | Glu(OBu$^t$)-Ile-Leu-Asp(OBu$^t$)-Val-Pro-NH-(CH$_2$)$_5$-COOH | 52 | c(Glu-Ile-Leu-Asp-Val-Pro-NH-(CH$_2$)$_5$-CO) | 20–40% water-acetonitrile (60 min.) |
| 167 | Glu(OBu$^t$)-Ile-Leu-Asp(OBu$^t$)-Val-Pro-NH-(CH$_2$)$_7$-COOH | 53 | c(Glu-Ile-Leu-Asp-Val-Pro-NH-(CH$_2$)$_7$-CO) | 10–50% water-acetonitrile (60 min.) |
| 168 | D-Leu-Leu-Asp(OBu$^t$)-Val-NH-(CH$_2$)$_2$-S-CH$_2$-COOH | 54 | D-Leu-Leu-Asp-Val-NHCH$_2$CH$_2$-S-CH$_2$ (cyclic, OC-) | 10–50% water-acetonitrile (60 min.) |
| 169 | MeIle-Leu-Asp(OBu$^t$)-Val-NH-(CH$_2$)$_4$-COOH | 55 | MeIle-Leu-Asp-Val-NH(CH$_2$)$_4$CO (cyclic) | 15–40% water-acetonitrile (65 min.) |
| 170 | D-tert-Leu-Asp(OBu$^t$)-Val-NH-(CH$_2$)$_4$-COOH | 56 | (CH$_3$)$_2$C(CH$_3$)-D-HN-CO-Leu-Asp-Val-NH(CH$_2$)$_4$CO (cyclic) | 15–55% water-acetonitrile (65 min.) |

TABLE 1-continued

Synthesis and purification of cyclic peptides

| NO: | Precursor | SEQ ID NO: | End Product Cyclic Peptide | High Pressure Liquid Chromatography (HPLC) (Gradient system and time) |
|---|---|---|---|---|
| 171 | D-Leu-Leu-Asp-Val-NHCH$_2$—S—CH$_2$—OC | 57 | D-Leu-Leu-Asp-Val-NHCH$_2$—SO—CH$_2$—OC | 10–50% water-acetonitrile (60 min.) |
| 172 | Ile-Leu-Asp(OBu$^t$)-Val-NH-(CH$_2$)$_2$-S-(CH$_2$)$_2$-COOH | 58 | Ile-Leu-Asp-Val-NH—CH$_2$—CH$_2$—S—CH$_2$—OC | 10–50% water-acetonitrile (60 min.) |
| 173 | Gly-D-Leu-Asp(OBu$^t$)-Val-Gly | 59 | c(D-Leu-Leu-Asp-Val-Gly-Gly) | 10–50% water-acetonitrile (60 min.) |
| 174 | β-Ala-D-Leu-Leu-Asp(OBu$^t$)-Val-β-Ala | 60 | c(D-Leu-Leu-Asp-Val-β-Ala-β-Ala) | 10–40% water-acetonitrile (60 min.) |
| 175 | Gly-D-Leu-Leu-Asp(OBu$^t$)-Val-β-Ala | 61 | c(D-Leu-Leu-Asp-Val-β-Ala-Gly) | 10–40% water-acetonitrile (60 min.) |
| 176 | Leu-Asp(OBu$^t$)-Val-β-Ala-MeAla-D-Leu | 62 | c(D-Leu-Leu-Asp-Val-β-Ala-MeAla) | 10–40% water-acetonitrile (60 min.) |
| 177 | Leu-Asp(OBu$^t$)-Val-β-Ala-Pro-D-Leu | 63 | c(D-Leu-Leu-Asp-Val-β-Ala-Pro) | 10–50% water-acetonitrile (60 min.) |
| 178 | D-Ala-D-Leu-Leu-Asp(OBu$^t$)-Val-D-Ala | 64 | c(D-Leu-Leu-Asp-Val-D-Ala-D-Ala) | 10–40% water-acetonitrile (60 min.) |
| 179 | NH$_2$-(CH$_2$)$_5$-CO-D-Leu-Leu-Asp(OBu$^t$)-Val-β-Ala | 65 | c(D-Leu-Leu-Asp-Val-β-Ala-NH-(CH$_2$)$_5$-CO) | 10–40% water-acetonitrile (60 min.) |
| 180 | D-Ala-D-Leu-Leu-Asp(OBu$^t$)-Val-β-Ala | 66 | c(D-Leu-Leu-Asp-Val-β-Ala-D-Ala) | 10–40% water-acetonitrile (60 min.) |
| 181 | Leu-Asp(OBu$^t$)-Val-Pro-Pro-D-Leu | 67 | c(D-Leu-Leu-Asp-Val-Pro-Pro) | 10–40% water-acetonitrile (60 min.) |
| 182 | Leu-Asp(OBu$^t$)-Val-Pro-D-Pro-D-Leu | 68 | c(D-Leu-Leu-Asp-Val-Pro-D-Pro) | 20–60% water-acetonitrile (60 min.) |
| 183 | Ile-Leu-Asp(OBu$^t$)-Leu-NH(CH$_2$)$_4$COOH | 69 | Ile-Asp-Leu-NH(CH$_2$)$_4$CO | 15–45% water-acetonitrile (65 min.) |
| 184 | NH$_2$—HC—CH$_2$—CH$_2$—CO——Ile-Leu-Asp(OBu$^t$)-Val CO——NH$_2$ | 70 | CO——Ile-Leu-Asp-Val-NH——CH——CONH$_2$ CH$_2$ | 10–50% water-acetonitrile (60 min.) |
| 185 | Ile-Leu-Asp(OBu$^t$)-Phe-NH(CH$_2$)$_4$COOH | 71 | Ile-Leu-Asp-Phe-NH(CH$_2$)$_4$CO | 20–45% water-acetonitrile (65 min.) |
| 186 | β-Ala-Ile-Leu-Asp(OBu$^t$)-Val-NH(CH$_2$)$_4$COOH | 72 | c(Ile-Leu-Asp-Val-NH(CH$_2$)$_4$-CO-β-Ala) | 10–40% water-acetonitrile (60 min.) |
| 187 | NH(CH$_2$)$_2$-CO-Pro-MeIle-Leu-Asp(OBu$^t$)-Val | 73 | c(MeIle-Leu-Asp-Val-β-Ala-Pro) | 10–40% water-acetonitrile (60 min.) |
| 188 | NH(CH$_2$)$_2$-CO-D-Ala-MeIle-Leu-Asp(OBu$^t$)-Val | 74 | c(MeIle-Leu-Asp-Val-β-Ala-D-Ala) | 10–50% water-acetonitrile (60 min.) |
| 189 | D-Ala-Val-D-Ala-MeIle-Leu-Asp(OBu$^t$)-Val | 75 | c(MeIle-Leu-Asp-Val-D-Ala-D-Ala) | 10–50% water-acetonitrile (60 min.) |

TABLE 1-continued

Synthesis and purification of cyclic peptides

| NO: | Precursor | SEQ ID NO: | End Product Cyclic Peptide | High Pressure Liquid Chromatography (HPLC) (Gradient system and time) |
|---|---|---|---|---|
| 190 | NH(CH$_2$)$_2$-CO-D-Orn-MeIle-Leu-Asp(OBu$^t$)-Val | 76 | c(MeIle-Leu-Asp-Val-β-Ala-D-Orn) | 10–35% water-acetonitrile (60 min.) |
| 191 | NH(CH$_2$)$_2$-CO-D-Lys-MeIle-Leu-Asp(OBu$^t$)-Val | 77 | c(MeIle-Leu-Asp-Val-β-Ala-D-Lys) | 10–35% water-acetonitrile (60 min.) |
| 192 | (structure) | 78 | (structure) | 15–30% water-acetonitrile (65 min.) |
| 193 | (structure) | 79 | (structure) | 15–30% water-acetonitrile (65 min.) |
| 194 | (structure) | 80 | (structure) | 10–50% water-acetonitrile (60 min.) |
| 195 | (structure) | 81 | (structure) | 15–30% water-acetonitrile (65 min.) |

TABLE 1-continued

Synthesis and purification of cyclic peptides

| NO: | Precursor | SEQ ID NO: | End Product Cyclic Peptide | High Pressure Liquid Chromatography (HPLC) (Gradient system and time) |
|---|---|---|---|---|
| 196 | | 82 | | 10–40% water-acetonitrile (60 min.) |
| 197 | | 83 | | 10–40% water-acetonitrile (60 min.) |
| 198 | | 84 | | 10–35% water-acetonitrile (60 min.) |
| 199 | | 85 | | 5–25% water-acetonitrile (60 min.) |
| 200 | | 86 | | 5–25% water-acetonitrile (60 min.) |

TABLE 1-continued

Synthesis and purification of cyclic peptides

| SEQ ID NO: | Precursor | End Product Cyclic Peptide | High Pressure Liquid Chromatography (HPLC) (Gradient system and time) |
|---|---|---|---|
| 201 | D-Lys(Boc)-Ile-Leu-Asp(OBut)-Val-N(piperidine)-CH₂-COOH | Ile-Leu-Asp-Val-N(piperidine)-CO, cyclized to D-Lys | 5–25% water-acetonitrile (60 min.) |
| 202 | MeIle-Leu-Asp(OBut)-Val-D-Lys(Pmc)-N(piperidine)-CH₂-COOH | MeIle-Leu-Asp-Val-D-Arg-N(piperidine)-CH₂-CO cyclic | 15–30% water-acetonitrile (60 min.) |
| 203 | D-Arg(Pmc)-MeIle-Leu-Asp(OBut)-Val-N(piperidine)-CH₂-COOH | D-Arg-MeIle-Leu-Asp-Val-N(piperidine)-CH₂-CO cyclic | 10–30% water-acetonitrile (65 min.) |
| 204 | D-Arg(Pmc)-D-Ala-MeIle-Leu-Asp(OBut)-Val | c(MeIle-Leu-Asp-Val-D-Arg-D-Ala) | 10–50% water-acetonitrile (60 min.) |
| 205 | D-Ala-D-Arg(Pmc)-MeIle-Leu-Asp(OBut)-Val | c(MeIle-Leu-Asp-Val-D-Ala-D-Arg) | 10–50% water-acetonitrile (60 min.) |
| 206 | D-Orn(Boc)-D-Ala-MeIle-Leu-Asp(OBut)-Val | c(MeIle-Leu-Asp-Val-D-Orn-D-Ala) | Purified as the protected peptide |
| 207 | D-Lys(Boc)-D-Ala-MeIle-Leu-Asp(OBut)-Val | c(MeIle-Leu-Asp-Val-D-Lys-D-Ala) | 10–35% water-acetonitrile (60 min.) |
| 208 | D-Ala-D-Lys(Boc)-MeIle-Leu-Asp(OBut)-Val | c(MeIle-Leu-Asp-Val-D-Ala-D-Lys) | 10–40% water-acetonitrile (60 min.) |
| 209 | D-Lys(Boc)-D-Lys(Boc)-MeIle-Leu-Asp(OBut)-Val | c(MeIle-Leu-Asp-Val-D-Lys-D-Lys) | 10–30% water-acetonitrile (60 min.) |
| 210 | D-Phe-D-Lys(Boc)-MeIle-Leu-Asp(OBut)-Val | c(MeIle-Leu-Asp-Val-D-Phe-D-Lys) | 10–40% water-acetonitrile (60 min.) |
| 211 | D-Phe-D-Arg(Pmc)-MeIle-Leu-Asp(OBut)-Val | c(MeIle-Leu-Asp-Val-D-Phe-D-Arg) | 10–50% water-acetonitrile (60 min.) |
| 212 | D-Trp-D-Arg(Pmc)-MeIle-Leu-Asp(OBut)-Val | c(MeIle-Leu-Asp-Val-D-Trp-D-Arg) | 10–50% water-acetonitrile (60 min.) |
| 213 | D-Trp-D-Lys(Boc)-MeIle-Leu-Asp(OBut)-Val | c(MeIle-Leu-Asp-Val-D-Trp-D-Lys) | 10–40% water-acetonitrile (60 min.) |
| 214 | D-His(Trt)-D-Lys(Boc)-MeIle-Leu-Asp(OBut)-Val | c(MeIle-Leu-Asp-Val-D-His-D-Lys) | 10–35% water-acetonitrile (60 min.) |
| 215 | D-Arg(Pmc)-D-Arg(Pmc)-MeIle-Leu-Asp(OBut)-Val | c(MeIle-Leu-Asp-Val-D-Arg-D-Arg) | 10–30% water-acetonitrile (60 min.) |
| 216 | D-His(Trt)-D-Arg(Pmc)-MeIle-Leu-Asp-Val | c(MeIle-Leu-Asp-Val-D-His-D-Arg) | 15–30% water-acetonitrile (60 min.) |
| 217 | D-Arg(Pmc)-D-His(Trt)-MeIle-Leu-Asp-Val | c(MeIle-Leu-Asp-Val-D-Arg-D-His) | 15–30% water-acetonitrile (60 min.) |
| 218 | D-Ala-D-Orn-MeIle-Leu-Asp-Val | c(MeIle-Leu-Asp-Val-D-Ala-D-Orn) | 15–30% water-acetonitrile (65 min.) |
| 219 | D-Orn-D-Orn-MeIle-Leu-Asp-Val | c(MeIle-Leu-Asp-Val-D-Orn-D-Orn) | Purified as the protected peptide |
| 220 | c(MeIle-Leu-Asp(OBut)-Val-D-Arg(Pmc)-D-Ala) | c(MeIle-Leu-Asp-Val-D-Arg(Pmc)-D-Ala) | |
| 221 | c(MeIle-Leu-Asp(OBut)-Val-D-Ala-D-Arg(Pmc)) | c(MeIle-Leu-Asp-Val-D-Ala-D-Arg(Pmc)) | |

TABLE 1-continued

Synthesis and purification of cyclic peptides

| NO: | Precursor | SEQ ID NO: | End Product Cyclic Peptide | High Pressure Liquid Chromatography (HPLC) (Gradient system and time) |
|---|---|---|---|---|
| 222 | c(MeIle-Leu-Asp(OBut)-Val-D-Phe-D-Arg(Pmc)) | 108 | c(MeIle-Leu-Asp-Val-D-Phe-D-Arg(Pmc)) | |
| 223 | c(MeIle-Leu-Asp(OBut)-Val-D-Trp-D-Arg(Pmc)) | 109 | c(MeIle-Leu-Asp-Val-D-Trp-D-Arg(Pmc)) | |
| 224 | c(MeIle-Leu-Asp-Val-D-Orn-D-Ala) | 110 | c(MeIle-Leu-Asp-Val-D-Orn(Et$_2$)-D-Ala) | 25-40% water-acetonitrile (60 min.) |
| 225 | c(MeIle-Leu-Asp-Val-D-Orn-D-Ala) | 111 | c(MeIle-Leu-Asp-Val-D-Orn(CHMe$_2$)-D-Ala) | 25-40% water-acetonitrile (60 min.) |
| 226 | c(MeIle-Leu-Asp-Val-D-Orn-D-Ala) | 112 | c(MeIle-Leu-Asp-Val-D-Orn(cyclohexyl)-D-Ala) | 25-40% water-acetonitrile (60 min.) |
| 227 | c(MeIle-Leu-Asp-Val-D-Orn-D-Ala) | 113 | c(MeIle-Leu-Asp-Val-D-Orn(p-Cl-benzyl)-D-Ala) | 25-40% water-acetonitrile (60 min.) |
| 228 | c(MeIle-Leu-Asp-Val-D-Lys-D-Lys) | 114 | c(MeIle-Leu-Asp-Val-D-Lys(CHMe$_2$)-D-Lys(CHMe$_2$)) | 10-40% water-acetonitrile (60 min.) |

TABLE 2

Synthesis and Characterisation of the Cyclic Peptides

| Comp. No. | End Product Cyclic Peptide | Amino Acid Analysis (Acid hydrolysis - 6N HCl containing 1% phenol, 24 hours, 130° C.) | HPLC Retention Time (Min.) | Mass Spectroscopy (M+H)+ |
|---|---|---|---|---|
| 1 | c(Ile-Leu-Asp-Val-NH—(CH$_2$)$_3$—CO) | Asp 0.97, Val 0.95, Ile 1.01, Leu 1.05 | 22.36 Novapak column, 10–60% (30 min.) | 526 |
| 2 | c(Ile-Leu-Asp-Val-NH—(CH$_2$)$_4$—CO) | Asp 1.01, Val 0.95, Ile 1.0, Leu 1.05 | 16.9 Novapak colunm 10–60% (30 min.) | 540 |
| 3 | c(Ile-Leu-Asp-Val-NH—(CH$_2$)$_5$—CO) | Asp 1.01, Val 0.97, Ile 1.0, Leu 1.03 | 18.03 Novapak column, 10–60% (30 min.) | 554 |
| 4 | c(Ile-Leu-Asp-Val-NH—(CH$_2$)$_7$—CO) | Asp 1.05, Val 0.98, Ile 0.95, Leu 1.04 | 21.04 Novapak column 10–60% (30 min.) | 582 |
| 5 | c(D-Ile-Leu-Asp-Val-NH—(CH$_2$)$_5$—CO) | Asp 1.01, Val 0.98, Ile 1.0, Leu 1.01 | 15.8 10–60% (30 min.) | 554 |
| 6 | c(D-Leu-Leu-Asp-Val-NH—(CH$_2$)$_5$—CO) | Asp 1.01, Val 0.97, Leu 2.03 | 16.28 10–60% (30 min.) | 554 |
| 7 | cyclo[Pro-Leu-Asp-Val-NH(CH$_2$)$_5$CO] | Asp 1.00, Pro 1.05, Val 0.95, Leu 1.01, Leu 1.04, Ahx 0.97 | 16.81 10–60% (30 min.) | 538 |
| 8 | cyclo[Gly-Leu-Asp-Val-NH(CH$_2$)$_5$CO] | Asp 1.00, Gly 1.04, Val 0.95, Leu 1.02, Leu 1.04, Ahx 0.97 | 12.31 10–60% (30 min.) | 498 |
| 9 | cyclo[t-Leu-Leu-Asp-Val-NH(CH$_2$)$_5$CO] | Asp 0.97, Val 0.99, Leu 1.01, Ahx 1.05, t-Leu | 21.57 10–60% (30 min.) | 554 |
| 10 | cyclo[t-butyl-Ala-Leu-Asp-Val-NH(CH$_2$)$_5$CO] | Asp 0.97, Val 0.99, Leu 1.0l, Ahx 1.05, t-butyl-Ala | 22.66 10–60% (30 min.) | 568 |
| 11 | Ac-NH-CH(CH$_2$CH$_2$CH$_2$CH$_2$NH-)-CO-Ile-Leu-Asp-Val→ [D-Lys analogue] | Asp 1.02, Val 0.98, Leu 1.01, Ile 0.99, Lys 0.99 | 18.91 10–60% (30 min.) | 611 |
| 12 | Ac-NH-CH(CH$_2$CH$_2$CH$_2$NH-)-CO-Ile-Leu-Asp-Val→ [D-Orn analogue] | Asp 1.02, Val 1.00, Leu 0.97, Ile 0.96, Orn 1.03 | 17.95 10–60% (30 min.) | 597 |
| 13 | Ac-NH-CH(CH$_2$CH$_2$CH$_2$NH-)-CO-Ile-Leu-Asp-Val→ [L-Orn analogue] | Asp 1.02, Val 0.98, Leu 1.01, Ile 0.99, Lys 0.99 | 12.69 10–60% (30 min.) | 597 |

TABLE 2-continued

Synthesis and Characterisation of the Cyclic Peptides

| Comp. No. | End Product Cyclic Peptide | Amino Acid Analysis (Acid hydrolysis - 6N HCl containing 1% phenol, 24 hours, 130° C.) | HPLC Retention Time (Min.) | Mass Spectroscopy (M+H)+ |
|---|---|---|---|---|
| 14 | [structure: Ac-NH-CH(-CH2CH2CH2CH2-NH-)-CO-D-Ile-Leu-Asp-Val- cyclized] [D-Lys analogue] | Asp 1.00, Val 0.95, Leu 1.03, Ile 1.00, Lys 0.97 | 17.71 10–60% (30 min.) | 611 |
| 15 | [structure: Ile-Leu-Asp-Val- linked to 4-aminomethylbenzoyl, cyclic] | Asp 1.05, Val 1.02, Ile 0.98, Leu 1.04, Lys 0.97, 4-aminomethylbenzoic acid present but not estimated. | 21.37 10–60% (30 min.) | 574 |
| 16 | [structure: Ile-Leu-Asp-Val-NHCH2—CH2-(imidazole)-N-CH2-CO cyclic] | Asp 1.02, Val 0.96, Ile 0.95, Leu 1.05 | 18.01 10–60% (30 min.) | 592.6 |
| 17 | [structure: D-Leu-Leu-Asp-Val-N(piperazine)N-CH2-CO cyclic] | Asp 1.03, Val 1.00, Leu 2.03 | 16.43 10–60% (30 min.) | 567.5 |
| 18 | [structure: CH2CO-Ile-Leu-Asp-Val-N(piperazine)N-CH2-CO-NH- with CH2 branch] | Asp 1.00, Val 1.04, Ile 0.97, Leu 0.99, β-Ala 0.96 | 16.82 10–60% (30 min.) | 638.4 |
| 19 | [structure: CH2CO-D-Leu-Leu-Asp-Val-N(piperazine)N-CH2-...-HN-CO with CH2 branch] | Asp 1.02, Val 1.05, Leu 1.96, β-Ala 0.95 | 18.70 10–60% (30 min.) | 638.3 |
| 20 | [structure: Ac-NH-CH(-CH2CH2CH2CH2-NH-)-CO-Ile-Leu-Asp-Val- cyclic] [L-Lys analogue] | Asp 1.01, Val 0.98, Ile 1.01, Leu 1.01, Lys 0.97 | 17.94 10–60% (30 min.) | 611 |
| 21 | [structure: Ac-NH-CH(-CH2CH2CH2-NH-)-CO-D-Ile-Leu-Asp-Val- cyclic] [L-Orn analogue] | Asp 1.04, Val 0.95, Ile 0.95, Leu 1.00, Orn 1.02 | 17.43 10–60% (30 min.) | 597 |
| 22 | [structure: Ac-NH-CH(-CH2CH2CH2-NH-)-CO-D-Ile-Leu-Asp-Val- cyclic] [D-Orn analogue] | Asp 1.03, Val 0.95, Ile 0.99, Leu 0.98, Orn 1.00 | 16.85 10–60% (30 min.) | 597 |

TABLE 2-continued

Synthesis and Characterisation of the Cyclic Peptides

| Comp. No. | End Product Cyclic Peptide | Amino Acid Analysis (Acid hydrolysis - 6N HCl containing 1% phenol, 24 hours, 130° C.) | HPLC Retention Time (Min.) | Mass Spectroscopy (M+H)+ |
| --- | --- | --- | --- | --- |
| 23 | Ac-NH-CH(-(CH2)4-NH-)-C(=O)-D-Ile-Leu-Asp-Val- [L-Lys analogue] | Asp 1.02, Val 0.97, Ile 1.04, Leu 1.01, Lys 0.97 | 17.96 10–60% (30 min.) | 611 |
| 24 | Ac-NH-CH(-(CH2)2-NH-)-C(=O)-D-Ile-Leu-Asp-Val- [L-Dab analogue] | Asp 1.03, Val 0.97, Ile 0.95, Leu 1.00, Dab 1.02 | 17.41 10–60% (30 min.) | 583 |
| 25 | Ac-NH-CH(-(CH2)2-NH-)-C(=O)-Ile-Leu-Asp-Val- [L-Dab analogue] | Asp 1.04, Val 0.96, Ile 0.98, Leu 1.00, Dab 1.01 | 20.26 10–60% (30 min.) | 583.5 |
| 26 | Ac-NH-CH(-(CH2)2-NH-)-C(=O)-Ile-Leu-Asp-Val- [D-Dab analogue] | Asp 1.00, Val 0.96, Ile 0.98, Leu 1.01, Dab 1.05 | 19.49 10–60% (30 min.) | 583.6 |
| 27 | Ac-NH-CH(-(CH2)2-NH-)-C(=O)-D-Leu-Leu-Asp-Val- [D-Dab analogue] | Asp 1.03, Val 0.99, Leu 1.98, Dab 0.99 | 17.79 10–60% (30 min.) | 583 |
| 28 | ⌐D-Ile-Leu-Asp-Val-NH(CH2)4CO⌐ | Asp 1.02, Val 0.98, Ile 1.03, Leu 1.01 | 19.02 10–60% (30 min.) | 540 |
| 29 | ⌐D-Leu-Leu-Asp-Val-NH(CH2)4CO⌐ | Asp 1.03, Val 0.96, Leu 2.01 | 19.56 10–60% (30 min.) | 540 |
| 30 | ⌐D-Val-Leu-Asp-Val-NH(CH2)5CO⌐ | Asp 1.03, Val 1.95, Leu 1.02, Aminohexanoic acid 1.01 | 17.81 10–60% (30 min.) | 540 |
| 31 | ⌐MeAla-Leu-Asp-Val-NH(CH2)5CO⌐ | Asp 1.02, Val 1.0, Leu 1.0, Aminohexanoic acid 0.98 | 16.83 10–60% (30 min.) | 526 |
| 32 | ⌐MeLeu-Leu-Asp-Val-NH(CH2)5CO⌐ | Asp 1.03, Val 1.03, Leu 1.02, Aminohexanoic acid 1.03 | 23.55 10–60% (30 min.) | 568 |
| 33 | ⌐Ile-t-but-Ala-Asp-Val-NH(CH2)4CO⌐ | Asp 0.97, Val 0.95, Ile 0.96, Aminovaleric acid 1.04 | 23.47 10–60% (30 min.) | 554 |
| 34 | ⌐Ile-Ile-Asp-Val-NH(CH2)4CO⌐ | Asp 1.05, Val 0.96, Ile 1.95, Aminovaleric acid 1.04 | 18.88 10–60% (30 min.) | 540 |

TABLE 2-continued

Synthesis and Characterisation of the Cyclic Peptides

| Comp. No. | End Product Cyclic Peptide | Amino Acid Analysis (Acid hydrolysis - 6N HCl containing 1% phenol, 24 hours, 130° C.) | HPLC Retention Time (Min.) | Mass Spectroscopy (M+H)+ |
|---|---|---|---|---|
| 35 | ⎡→Ile-Nle-Asp-Val-NH(CH₂)₄CO→⎤ (cyclic) | Asp 1.00, Val 0.95, Ile 0.99, Nle 0.99, Aminovaleric acid 0.94 | 21.36 10–60% (30 min.) | 540 |
| 36 | ⎡→Ile-Val-Asp-Val-NH(CH₂)₄CO→⎤ (cyclic) | Asp 0.95, Val 1.93, Ile 0.97, Aminovaleric acid 1.05 | 17.30 10–60% (30 min.) | 526 |
| 37 | ⎡→Ile-Cha-Asp-Val-NH(CH₂)₄CO→⎤ (cyclic) | Asp *1.02, Val 0.98, Ile 1.00, Aminovaleric acid 1.04 | 25.37 10–60% (30 min.) | 580 |
| 38 | ⎡→Ile-tert-Leu-Asp-Val-NH(CH₂)₄CO→⎤ (cyclic) | Asp 0.97, Val 0.95, Ile 0.96, Aminovaleric acid 1.04 | 18.45 10–60% (30 min.) | 540 |
| 39 | [D-Lys] structure: H₂N-CH(-D-Ile-Leu-Asp-Val→)-(CH₂)₄-NH← | Asp 1.05, Val 0.98, Ile 0.99, Leu 1.02 Lys 0.97 | 15.83 10–60% (30 min.) | 569.3 |
| 40 | [D-Lys analogue] structure: Z-NH-CH(-D-Ile-Leu-Asp-Val→)-(CH₂)₄-NH← | Asp 1.04, Val 0.98, Ile 0.95, Leu 0.99 Lys 1.02 | 26.65 10–60% (30 min.) | 703 |
| 41 | [D-Lys analogue] structure: CH₃-C(=O)-NH-CH(-D-Ile-Leu-Asp-Val→)-(CH₂)₄-NH← | Asp 1.04, Val 1.01, Ile 0.96, Leu 1.03, Lys 0.98 | 19.23 10–60% (30 min.) | 625.5 |
| 42 | [D-Lys analogue] structure: HOOC-(CH₂)₂-C(=O)-NH-CH(-D-Ile-Leu-Asp-Val→)-(CH₂)₄-NH← | Asp 1.02, Val 0.97, Ile 0.99, Leu 1.02, Lys 0.99 | 17.51 10–60% (30 min.) | 669.5 |
| 43 | [D-Lys analogue] structure: (CH₃)₂CH-CH₂-C(=O)-NH-CH(-D-Ile-Leu-Asp-Val→)-(CH₂)₄-NH← | Asp 1.03, Val 1.04, Ile 1.01, Leu 1.02 Lys 0.97 | 22.74 10–60% (30min.) | 653.6 |

TABLE 2-continued

Synthesis and Characterisation of the Cyclic Peptides

| Comp. No. | End Product Cyclic Peptide | Amino Acid Analysis (Acid hydrolysis - 6N HCl containing 1% phenol, 24 hours, 130° C.) | HPLC Retention Time (Min.) | Mass Spectroscopy (M+H)+ |
|---|---|---|---|---|
| 44 | [structure: NH₂-CH₂CH₂-C(=O)-NH-CH(-(CH₂)₄-NH-)-C(=O)-D-Leu-Leu-Asp-Val→ cyclized to NH] [D-Lys analogue] | Asp 1.04, Val 0.98, Leu 2.01, Lys 0.95 | 16.31 10–60% (30 min.) | 640.5 |
| 45 | [structure: (H₃C-CH₂)₂N-CH(-(CH₂)₄-NH-)-C(=O)-D-Leu-Leu-Asp-Val→] [D-Lys analogue] | Asp 1.01, Val 0.96, Leu 1.96, Lys 0.95 | 18.01 10–60% (30 min.) | 625.6 |
| 46 | [structure: benzyl-NH-CH(-(CH₂)₄-NH-)-C(=O)-D-Leu-Leu-Asp-Val→] [D-Lys analogue] | Asp 1.05, Val 0.96, Leu 2.01, Lys 0.95 | 21.22 10–60% (30 min.) | 659.6 |
| 47 | [structure: 3-pyridyl-C(=O)-NH-CH(-(CH₂)₄-NH-)-C(=O)-D-Leu-Leu-Asp-Val→] [D-Lys analogue] | Asp 1.02, Val 0.97, Leu 1.99, Lys 0.96 | 17.77 10–60% (30 min.) | 674 |
| 48 | [structure: Glu-NH-CH(-(CH₂)₄-NH-)-C(=O)-D-Leu-Leu-Asp-Val→] [D-Lys analogue] | Asp 1.03, Glu 1.00, Val 0.96, Leu 1.95, Lys 0.97 | 16.43 10–60% (30 min.) | 698.6 |
| 49 | [structure: Pyr-NH-CH(-(CH₂)₄-NH-)-C(=O)-D-Leu-Leu-Asp-Val→] [D-Lys analogue] | Asp 1.04, Glu 1.00, Val 0.95, Leu 2.03, Lys 0.97 | 17.50 10–60% (30 min.) | 680.6 |
| 50 | c(Glu-Ile-Leu-Asp-Val-Pro-NH—(CH²)₂—CO) | Asp 1.00, Glu 1.02, Pro 1.07, Val 0.99, Leu 1.03, Ile 1.03, β-Ala 1.08 | 11.93 20–80% (40 min.) | 737.8 |
| 51 | c(Glu-Ile-Leu-Asp-Val-Pro-NH—(CH₂)₄—CO) | Asp 1.00, Glu 1.0, Pro 1.01, Val 0.95, Ile 0.97, Leu 1.03. | 11.53 20–80% (40 min.) | 765.9 |
| 52 | c(Glu-Ile-Leu-Asp-Val-Pro-NH—(CH₂)₅—CO) | Asp 1.00, Glu 1.0, Pro 1.01, Val 0.96, Ile 0.96, Leu 1.00. | 15.22 20–80% (40 min.) | 779.9 |
| 53 | c(Glu-Ile-Leu-Asp-Val-Pro-NH—(CH₂)₇—CO) | Asp 1.00, Glu 1.04, Pro 1.04, Val 0.95, Ile 1.03, Leu 1.05. | 17.78 20–80% (40 min.) | 807.9 |
| 54 | [structure: cyclic OC—...—CH₂-S-CH₂CH₂-NH-Val-Asp-Leu-D-Leu→] | Asp 1.00, Val 0.95, Leu 2.03. | 14.23 20–80% (40 min.) | (M–H)⁻ 556 |

TABLE 2-continued

Synthesis and Characterisation of the Cyclic Peptides

| Comp. No. | End Product Cyclic Peptide | Amino Acid Analysis (Acid hydrolysis - 6N HCl containing 1% phenol, 24 hours, 130° C.) | HPLC Retention Time (Min.) | Mass Spectroscopy (M+H)+ |
|---|---|---|---|---|
| 55 | ⌐—MeIle-Leu-Asp-Val-NH(CH₂)₄CO—⌐ (cyclic) | Asp 0.98, Val 0.95, Leu 1.04, Aminovaleric acid 1.05. | 21.83 10–60% (30 min.) | (M–H)⁻ 552.4 |
| 56 | [structure with t-Bu-like D-amino acid]—Leu-Asp-Val-NH(CH₂)₄CO— (cyclic) | Asp 0.99, Val 0.95, Leu 1.01, Aminovaleric acid 1.05. | 19.25 10–60% (30 min.) | (M–H)⁻ 538.5 |
| 57 | ⌐—D-Leu-Leu-Asp-Val-NHCH₂CH₂—SO, OC———CH₂ (cyclic) | Asp 1.00, Val 0.95, Leu 2.03. | 10.25 20–50% (40 min.) | (M–H)⁻ 572.9 |
| 58 | ⌐—Ile-Leu-Asp-Val-NH—CH₂—CH₂—S, OC———CH₂———CH₂ (cyclic) | Asp 1.00, Val 0.96, Ile 0.99, Leu 1.02. | 13.37 20–80% (40 min.) | (M–H)⁻ 570.5 |
| 59 | c(D-Leu-Leu-Asp-Val-Gly-Gly) | Asp 1.04, Gly 2.04, Val 0.95, Leu 2.0. | 14.07 20–80% (40 min.) | (M–H)⁻ 553 |
| 60 | c(D-Leu-Leu-Asp-Val-β-Ala-β-Ala) | Asp 1.04, Val 0.96, Leu 1.96, β-Ala 2.0. | 12.20 20–80% (40 min.) | (M–H)⁻ 581.6 |
| 61 | c(D-Leu-Leu-Asp-Val-β-Ala-Gly) | Asp 1.05, Gly 1.04, Val 1.0, Leu 1.05, β-Ala 0.96. | 12.20 20–80% (40 min.) | (M–H)⁻ 567.4 |
| 62 | c(D-Leu-Leu-Asp-Val-β-Ala-MeAla) | Asp 1.03, Val 1.0, Leu 1.98, β-Ala 0.96. | 11.52 20–80% (40 min.) | (M–H)⁻ 595.8 |
| 63 | c(D-Leu-Leu-Asp-Val-β-Ala-Pro) | Asp 1.0, Pro 1.01, Val 0.95, Leu 2.0, β-Ala 1.03. | 14.4 20–80% (40 min.) | (M–H)⁻ 607.5 |
| 64 | c(D-Leu-Leu-Asp-Val-D-Ala-D-Ala) | Asp 1.05, Ala 2.05, Val 1.0, Leu 1.98. | 9.1 20–80% (40 min.) | 583.6 |
| 65 | c(D-Leu-Leu-Asp-Val-β-Ala-NH—(CH₂)₃—CO) | Asp 1.04, Val 0.97, Leu 2.0, β-Ala 0.97. | 10.11 20–80% (40 min.) | (M–H)⁻ 595.5 |
| 66 | c(D-Leu-Leu-Asp-Val-β-Ala-D-Ala) | Asp 1.03, Ala 1.02, Val 1.0, Leu 2.02, β-Ala 0.99. | 9.1 20–80% (40 min.) | (M–H)⁻ 581.8 |
| 67 | c(D-Leu-Leu-Asp-Val-Pro-Pro) | Asp 1.04, Pro 2.0, Val 0.95, Leu 1.97. | 10.6 20–80% (40 min.) | (M–H)⁻ 633.5 |
| 68 | c(D-Leu-Leu-Asp-Val-Pro-D-Pro) | Asp 1.04, Pro 2.0, Val 0.96, Leu 2.0. | 10.35 20–80% (40 min.) | (M–H)⁻ 633.4 |
| 69 | ⌐—Ile-Leu-Asp-Leu-NH(CH₂)₄CO—⌐ (cyclic) | Ile 0.96, Asp 1.01, Leu 2.02, Aminovaleric acid 1.01. | 22.93 10–60% (30 min.) | 554.4 |
| 70 | CO-Ile-Leu-Asp-Val-NH—CH—CONH₂, CH₂———CH₂ (cyclic) | Ile 0.95, Asp 1.0, Glu 0.99, Val 1.00, Leu 1.02. | 17.9 20–40% (40 min.) | (M–H)⁻ 567.4 |
| 71 | ⌐—Ile-Leu-Asp-Phe-NH(CH₂)₄CO—⌐ (cyclic) | Ile 0.96, Asp 1.04, Leu 1.01, Phe 0.98, Aminovaleric acid 1.04. | 23.46 10–60% (30 min.) | 588.4 |
| 72 | c(Ile-Leu-Asp-Val-NH(CH₂)₄—CO-β-Ala) | Ile 1.04, Asp 1.05, Val 0.96, Leu 1.00, β-Ala 0.96. | 12.44 20–80% (40 min.) | 611.5 |
| 73 | c(MeIle-Leu-Asp-Val-β-Ala-Pro) | Asp 1.05, Val 1.00, Leu 1.00, Pro 0.95, β-Ala 0.98. | 16.66 20–80% (40 min.) | 623.5 |
| 74 | c(MeIle-Leu-Asp-Val-β-Ala-D-Ala) | Asp 1.05, Val 1.00, Leu 0.98, Ala 1.00, β-Ala 0.96. | 15.98 20–80% (40 min.) | (M–H)⁻ 595.4 |
| 75 | c(MeIle-Leu-Asp-Val-D-Ala-D-Ala) | Asp 1.04, Val 0.98, Leu 1.00, Ala 1.96. | 16.24 20–80% (40 min.) | (M–H)⁻ 595.2 |
| 76 | c(MeIle-Leu-Asp-Val-β-Ala-D-Orn) | Asp 1.00, Val 0.95, Leu 1.01, Orn 0.98, β-Ala 0.98. | 13.98 20–50% (40 min.) | 640.4 |
| 77 | c(MeIle-Leu-Asp-Val-β-Ala-D-Lys) | Asp 1.00, Val 0.95, Leu 1.02, Lys 0.98, β-Ala 0.98. | 14.34 20–50% (40 min.) | 654.4 |

TABLE 2-continued

Synthesis and Characterisation of the Cyclic Peptides

| Comp. No. | End Product Cyclic Peptide | Amino Acid Analysis (Acid hydrolysis - 6N HCl containing 1% phenol, 24 hours, 130° C.) | HPLC Retention Time (Min.) | Mass Spectroscopy (M+H)$^+$ |
|---|---|---|---|---|
| 78 | CH$_2$—CO-Ile-Leu-Asp-Val-N(piperazine)N<br>CH$_2$—CH$_2$—NH—CO—CH$_2$ | Ile 0.97, Asp 1.02, Leu 1.01, Val 0.99, γ aminobutyric acid 1.01. | 23.11<br>10–40% (30 min.) | 652.4 |
| 79 | CH$_2$—CO-Ile-Leu-Asp-Val-N(piperazine)N<br>CH$_2$—CH$_2$—CH$_2$—NH—CO—CH$_2$ | Ile 0.97, Asp 1.01, Leu 1.02, Val 0.99, Aminovaleric acid 1.02. | 20.97<br>10–40% (30 min.) | 666.4 |
| 80 | (structure with Ac, Ile-Leu-Asp-Val, piperazine ring) | Ile 0.99, Asp 1.0, Val 0.96, Leu 0.97, Lys 1.0. | 16.2<br>20–80% (40 min.) | (M–H)$^-$<br>749.8 |
| 81 | CO-Ile-Leu-Asp-Val-NHCH$_2$—CH$_2$—(imidazole)—CH$_2$<br>CH$_2$—CH$_2$—NH—CO | Asp 1.04, Val 0.95, Leu 1.03, Ile 0.98. | 23.33<br>10–40% (30 min.) | 663.4 |
| 82 | (piperazine structure with D-Leu-Leu-Asp-Val) [D-Lys analogue] | Asp 1.0, Val 0.96, Leu 1.97, Lys 0.95. | 15.2<br>10–70% (40 min.) | 695.5 |
| 83 | (NH$_2$ structure with D-Leu-Leu-Asp-Val) [D-Lys analogue] | Asp 1.0, Val 0.95, Leu 1.95, Lys 0.97, γ-aminobutyric acid 0.95. | 16.5<br>10–70% (40 min.) | 654.4 |
| 84 | (Arg structure with D-Leu-Leu-Asp-Val) [D-Lys analogue] | Asp 1.0, Val 0.96, Leu 1.94, Lys 0.98, Arg 0.99. | 10.9<br>20–50% (40 min.) | 725.5 |
| 85 | Ile-Leu-Asp-Val-D-Lys-N(piperazine)N<br>CO—CH$_2$ | Asp 1.02, Val 0.98, Leu 1.01, Lys 1.02, Ile 0.96. | 19.61<br>10–40% (30 min.) | 695.5 |

TABLE 2-continued

Synthesis and Characterisation of the Cyclic Peptides

| Comp. No. | End Product Cyclic Peptide | Amino Acid Analysis (Acid hydrolysis - 6N HCl containing 1% phenol, 24 hours, 130° C.) | HPLC Retention Time (Min.) | Mass Spectroscopy $(M+H)^+$ |
|---|---|---|---|---|
| 86 | MeIle-Leu-Asp-Val-D-Lys-N⟨piperazine⟩N / CO—CH$_2$ | Asp 1.01, Val 0.98, Leu 1.01, Lys 1.00. | 21.89<br>10–40% (30 min.) | 709.4 |
| 87 | Ile-Leu-Asp-Val-N⟨piperazine⟩N—CH$_2$ / D-Lys—CO | Asp 1.03, Val 0.95, Leu 1.01, Lys 1.03, Ile 0.98. | 16.08<br>10–40% (30 min.) | 695.4 |
| 88 | MeIle-Leu-Asp-Val-D-Arg-N⟨piperazine⟩N / CO—CH$_2$ | Asp 1.02, Val 0.96, Leu 1.01, Arg 0.96. | 21.49<br>10–40% (30 min.) | 737.4 |
| 89 | D-Arg-MeIle-Leu-Asp-Val-N⟨piperazine⟩N / CO—CH$_2$ | Asp 1.0, Val 0.98, Leu 0.98, Arg 1.04. | 18.47<br>10–40% (30 min.) | 737.4 |
| 90 | c(MeIle-Leu-Asp-Val-D-Arg-D-Ala) | Asp 1.0, Val 0.97, Leu 0.97, Arg 0.95, Ala 0.99. | 13.4<br>20–80% (40 min.) | 682.5 |
| 91 | c(MeIle-Leu-Asp-Val-D-Ala-D-Arg) | Asp 1.0, Val 1.0, Leu 1.0, Arg 1.02, Ala 0.96. | 15.3<br>20–40% (40 min.) | 682.5 |
| 92 | c(MeIle-Leu-Asp-Val-D-Orn-D-Ala) | Asp 1.02, Val 1.0, Leu 1.0, Orn 1.02, Ala 1.02. | 28.26<br>10–40% (30 min.) | 640.5 |
| 93 | c(MeIle-Leu-Asp-Val-D-Lys-D-Ala) | Asp 1.03, Val 1.0, Leu 1.0, Lys 1.04, Ala 1.02. | 12.66<br>20–80% (40 min.) | 654.5 |
| 94 | c(MeIle-Leu-Asp-Val-D-Ala-D-Lys) | Asp 1.02, Val 0.99, Leu 1.01, Lys 1.0, Ala 1.0. | 9.99<br>20–80% (40 min.) | 654.5 |
| 95 | c(MeIle-Leu-Asp-Val-D-Lys-D-Lys) | Asp 1.05, Val 0.99, Leu 1.0, Lys 2.07. | 27.57<br>10–30% (40 min.) | 711.5 |
| 96 | c(MeIle-Leu-Asp-Val-D-Phe-D-Lys) | Asp 1.01, Val 0.99, Leu 1.0, Phe 1.0, Lys 0.99. | 13.29<br>20–80% (40 min.) | 730.5 |
| 97 | c(MeIle-Leu-Asp-Val-D-Phe-D-Arg) | Asp 1.0, Val 0.98, Leu 0.96, Arg 0.96, Phe 0.97. | 14.1<br>20–80% (40 min.) | 758.6 |
| 98 | c(MeIle-Leu-Asp-Val-D-Trp-D-Arg) | Asp 1.0, Val 0.98, Leu 0.96, Arg 0.96, Trp 0.82. | 21.0<br>20–50% (40 min.) | 797.4 |
| 99 | c(MeIle-Leu-Asp-Val-D-Trp-D-Lys) | Asp 1.0, Val 0.96, Leu 0.97, Lys 1.0, Trp 0.77. | 14.0<br>20–80% (40 min.) | 769.4 |
| 100 | c(MeIle-Leu-Asp-Val-D-His-D-Lys) | Asp 1.0, Val 0.95, Leu 0.96, His 0.97, Lys 0.96. | 25.0<br>20–80% (40 min.) | 720.4 |
| 101 | c(MeIle-Leu-Asp-Val-D-Arg-D-Arg) | Asp 1.0, Val 0.98, Leu 1.0, D-Arg 1.94 | 10.7<br>20–40% (40 min.) | 767.3 |
| 102 | c(MeIle-Leu-Asp-Val-D-His-D-Arg) | Asp 0.96, Val 0.98, Leu 1.01, Arg 0.96, His 0.97. | 18.86<br>10–40% (40 min.) | 749.0 |
| 103 | c(MeIle-Leu-Asp-Val-D-Arg-D-His) | Asp 1.0, Val 0.98, Leu 0.97, Arg 0.97, His 0.96. | 17.80<br>10–40% (40 min.) | 749.0 |
| 104 | c(MeIle-Leu-Asp-Val-D-Ala-D-Orn) | Asp 1.0, Val 0.98, Leu 0.96, Ala 0.99, Orn 0.97. | 22.67<br>10–40% (30 min.) | 640.4 |
| 105 | c(MeIle-Leu-Asp-Val-D-Orn-D-Orn) | Asp 1.0, Val 0.98, Leu 0.96, Orn 1.95. | 20.40<br>10–40% (30 min.) | 683.9 |
| 106 | c(MeIle-Leu-Asp-Val-D-Arg(Pmc)-DAla) | Asp 1.0, Val 0.96, Leu 0.96, Arg 0.95, Ala 0.99. | 28.3<br>20–80% (40 min.) | 948.5 |
| 107 | c(MeIle-Leu-Asp-Val-D-Ala-D-Arg(Pmc)) | Asp 1.0, Val 1.0, Leu 1.01, Arg 1.01, Ala 0.97. | 27.3<br>20–80% (40 min.) | 948.5 |
| 108 | c(MeIle-Leu-Asp-Val-D-Phe-D-Arg(Pmc)) | Asp 1.0, Val 0.96, Leu 0.96, Arg 0.95, Phe 0.97. | 31.0<br>20–80% (40 min.) | 1024.6 |
| 109 | c(MeIle-Leu-Asp-Val-D-Trp-D-Arg(Pmc)) | Asp 1.0, Val 0.98, Leu 0.97, Arg 0.97, Trp 0.80. | 31.9<br>20–80% (40 min) | 1063.5 |
| 110 | c(MeIle-Leu-Asp-Val-D-Orn(Et$^2$)-DAla) | Asp 1.01, Val 0.98, Leu 0.99, Orn(Et$_2$) 0.95, Ala 1.03. | 22.25<br>10–60% (30 min.) | 696.6 |
| 111 | c(MeIle-Leu-Asp-Val-D-Orn(CHMe$_2$)-D-Ala) | Asp 0.97, Val 0.95, Leu 1.01, Orn(Pr$^i$) 0.96, Ala 1.05. | 17.70<br>25–40% (30 min.) | 682.5 |

TABLE 2-continued

Synthesis and Characterisation of the Cyclic Peptides

| Comp. No. | End Product Cyclic Peptide | Amino Acid Analysis (Acid hydrolysis - 6N HCl containing 1% phenol, 24 hours, 130° C.) | HPLC Retention Time (Min.) | Mass Spectroscopy (M+H)+ |
|---|---|---|---|---|
| 112 | c(MeIle-Leu-Asp-Val-D-Orn(cyclohexyl)-D-Ala) | Asp 0.99, Val 0.98, Leu 1.0, Ala 1.02. 25–40% (30 min.) | 23.03 | 722.6 |
| 113 | c(MeIle-Leu-Asp-Val-D-Orn(p-Cl-benzyl)-D-Ala) | Asp 1.01, Val 0.98, Leu 0.99, Ala 1.02. 30–70% (30 min.) | 14.36 | 764.4 |
| 114 | c(MeIle-Leu-Asp-Val-D-Lys(CHMe$_2$)-D-Lys(CHMe$_2$)) | Asp 1.03, Val 1.0, Leu 0.99. 10–70% (40 min.) | 16.0 | 795.5 |

Notes on Sequence Listing

Tables 1 & 2 in this specification give a list of Compound Numbers. Sequence listings generated using the Patentin software have to be provided for some patent offices; but this is understood not to be obligatory for D amino acid containing peptides.

Accordingly the Sequence Listing provided in this specification does not include all the peptides included in Tables 1 & 2.

For the sake of convenience and clarity the following text gives a comparison between the Compound Numbers used in Tables 1 & 2 and the SEQ ID NO: given in the Sequence listing.

| Compound Number | SEQ ID NO: |
|---|---|
| 1–85 | 1–85 (note some do contain D amino acid) |
| 86–114 | None because all contain D amino acid |
| 115 | 86 |
| 116 | 87 |
| 117 | 88 |
| 118 | 89 |
| 119–120 | None because all contain D amino acid |
| 121 | 90 |
| 122 | 91 |
| 123 | 92 |
| 124 | 93 |
| 125–126 | None because all contain D amino acid |
| 127 | 94 |
| 128 | None because it contains D amino acids |
| 129 | 95 |
| 130 | 96 |
| 131 | None because it contains a D amino acid |
| 132 | 97 |
| 133 | None because it contains a D amino acid |
| 134 | 98 |
| 135–138 | None because all contain D amino acid |
| 139 | 99 |
| 140–144 | None because all contain D amino acid |
| 145 | 100 |
| 146 | 101 |
| 147 | 102 |
| 148 | 103 |
| 149 | 104 |
| 150 | 105 |
| 151 | 106 |
| 152 | 107 |
| 153–163 | None because all contain D amino acid |
| 164 | 108 |
| 165 | 109 |
| 166 | 110 |
| 167 | 111 |
| 168 | None because it contains D amino acid |
| 169 | 112 |
| 170–1 | None because all contain D amino acid |
| 172 | 113 |
| 173–182 | None because all contain D amino acid |
| 183 | 114 |
| 184 | 115 |
| 185 | 116 |
| 186 | 117 |
| 187 | 118 |
| 188–191 | None because all contain D amino acid |
| 192 | 119 |
| 193 | 120 |
| 194 | 121 |
| 195 | 122 |
| 196–228 | None because all contain D amino acid |

I claim:

1. A cyclic peptide of formula 1

wherein AA1 is an L or D amino acid selected from the group consisting of Ile, Leu, Pro, Gly, Tic, Val, tert-Leu, tert-butyl-Ala, Phe, Nle, Met, Arg, Lys and Ala;

AA2 is an L amino acid selected from Leu, Ile, Phe, Val, tert-Leu, Nle, Cha and tert-butyl-Ala;

AA3 is an L amino acid selected from Asp or Glu;

AA4 is an L amino acid selected from Val, Leu, Ile, Phe, Cha, Nle and Nva;

wherein each amino acid of AA1, AA2, AA3 and AA4 is optionally independently alkylated with a $C_{1-4}$alkyl group;

LINKER represents a linking moiety for linking N terminus of AA1 to C terminus of AA4 to form a cyclic peptide containing a heterocyclic ring having 17 to 30 members;

the cyclic peptide having an $IC_{50}$ of <20 μM in the MOLT-4 cell/fibronectin assay described herein and/or;

the cyclic peptide having an $IC_{50}$ of <100 μM in the MOLT-4 cell/recombinant soluble VCAM-1 assay described herein and;

AA1-4 have the general formula 2

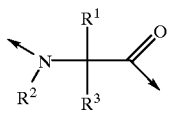

wherein R1 is the amino acid side chain and

R2 and R3, which may be the same or different for each AA1-AA4, independently represent H or $C_{1-4}$alkyl;

or a salt thereof.

2. A cyclic peptide according to claim 1 wherein:

AA1 is selected from Ile and Leu either of which is optionally $\underline{N}$-methylated;

AA2 is Leu;

AA3 is Asp and;

AA4 is Val;

or a salt thereof.

3. A cyclic peptide according to any one of claims 1 and 2 wherein LINKER is a group of formula 4

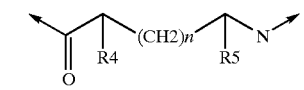

wherein:

n=3–5 and

R4 and R5 represent H or;

R4 represents $NH_2$ optionally substituted with a $C_{1-10}C$(O)— group;

or $NH_2$ is optionally substituted with natural amino acids via α-carboxyl, the $\underline{N}$ terminus of the amino acid optionally being substituted with a $C_{1-10}C(O)$— group;

or $NH_2$ is optionally mono or di substituted with $C_{1-4}$alkyl;

or $NH_2$ is optionally substituted with benzyl, pyridyl, carboxy $C_{2-5}$alkanoyl or amino-$C_{2-5}$alkanoyl, and R5 is H or;

R4 is H and R5 is COOH optionally substituted with $C_{1-4}$alkyl to give an ester or R5 is an amide of formula —CONR6R7 where R6 and R7 independently represent H or $C_{1-4}$alkyl;

or a salt thereof.

4. A cyclic peptide according to any one of claims 1 and 2 in which LINKER represents a dipeptide containing at least one basic amino acid or a salt thereof.

5. A cyclic peptide according to claim 4 in which amino acids in the dipeptide LINKER are $\underline{D}$ amino acids or a salt thereof.

6. A process for the manufacture of a cyclic peptide of formula 1 according to claim 1 selected from:

(a) the removal of one or more conventional peptide protecting groups from a protected cyclic peptide of Formula 3

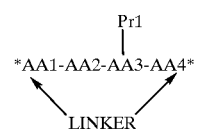

wherein Pr1 represents a protecting group on the acid group in the side chain of AA3 to give a cyclic peptide of the invention of formula I and optionally, simultaneously or subsequently, also removing any additional conventional peptide protecting groups present in the LINKER and optionally if desired converting the product thus obtained into a salt thereof;

(b) the formation of an amide bond by coupling two peptide units, one containing a carboxylic acid group, or a reactive derivative thereof, and the other containing an amino group, such that a protected or unprotected cyclic peptide having the sequence indicated in formula 1 is produced, and if necessary, the protecting groups are removed using process (a) above and optionally if desired converting the product thus obtained into a salt thereof;

(c) for a cyclic peptide according to formula 1, having —S(O)— or —S(O₂)— in the LINKER, oxidising —S—, or additionally —S(O)— in the case of —S(O₂)—, in the LINKER of a precursor cyclic peptide to give a cyclic peptide containing —S(O)— or —S(O₂)— in its LINKER and optionally if desired converting the product thus obtained into a salt thereof.

7. A pharmaceutical composition comprising a cyclic peptide according to claim 1 or 2 and a pharmaceutically acceptable diluent or carrier.

8. A cyclic peptide according to any one of claims 1 and 2, wherein the LINKER has a structure selected from the group consisting of:

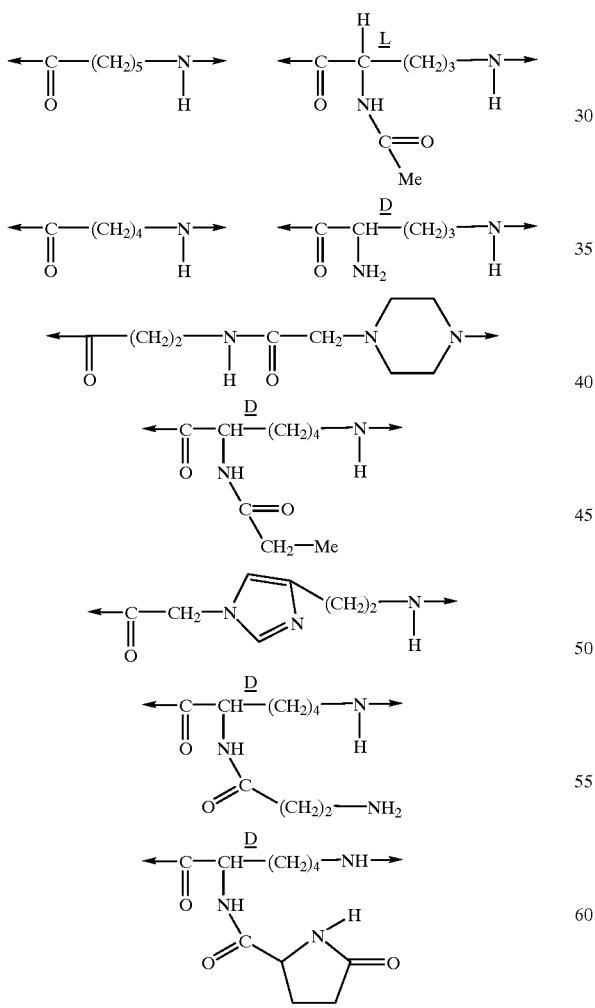
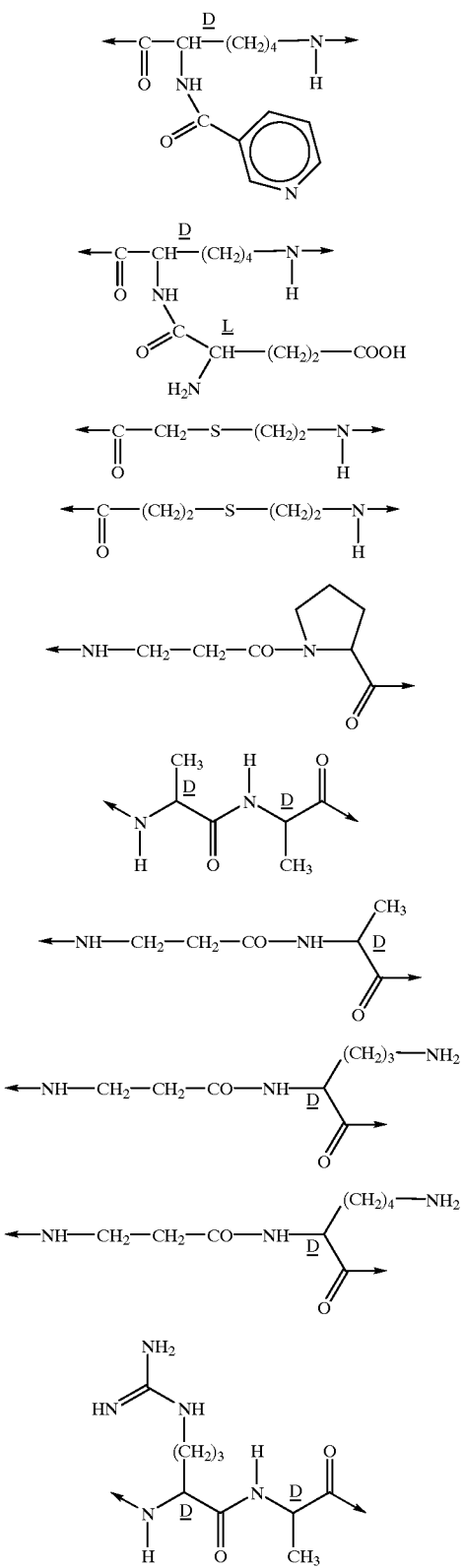

167
-continued
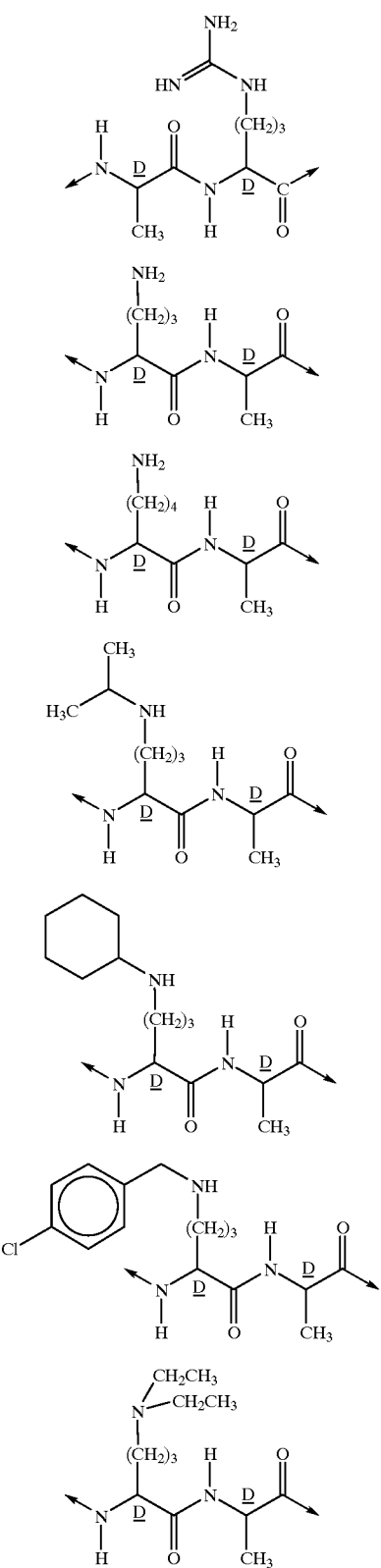
168
-continued
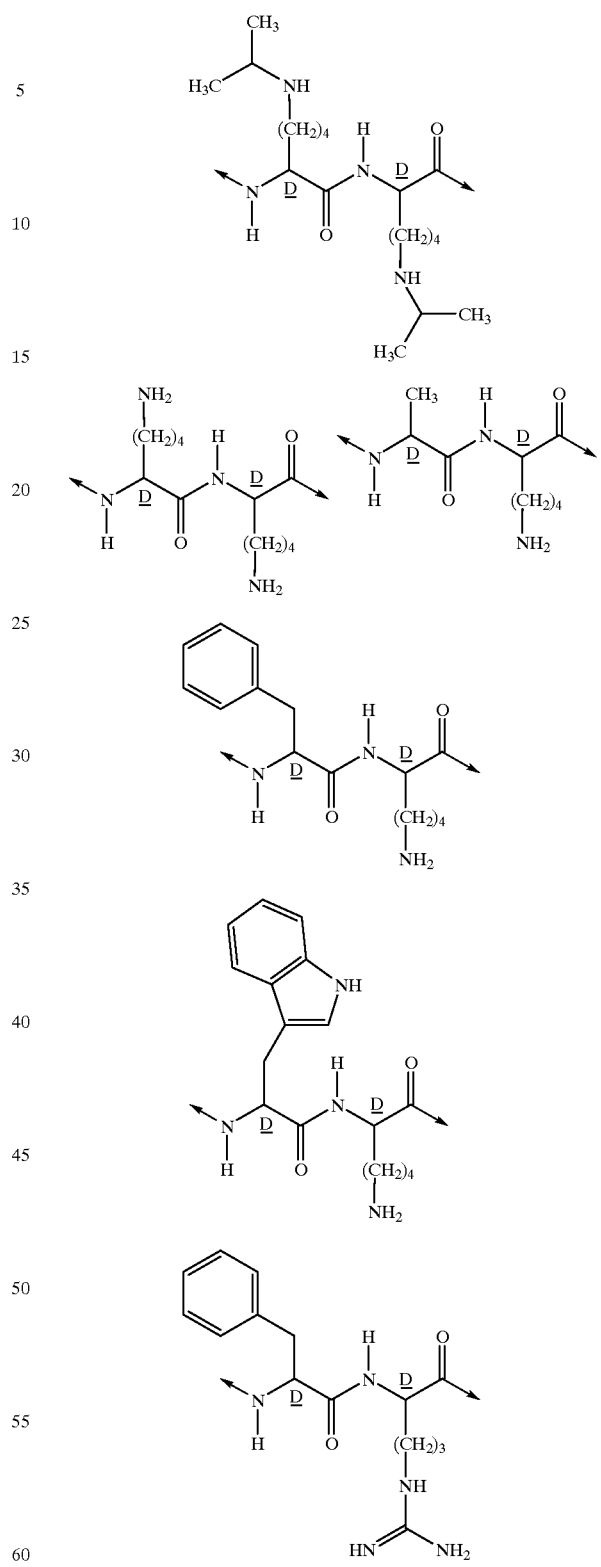

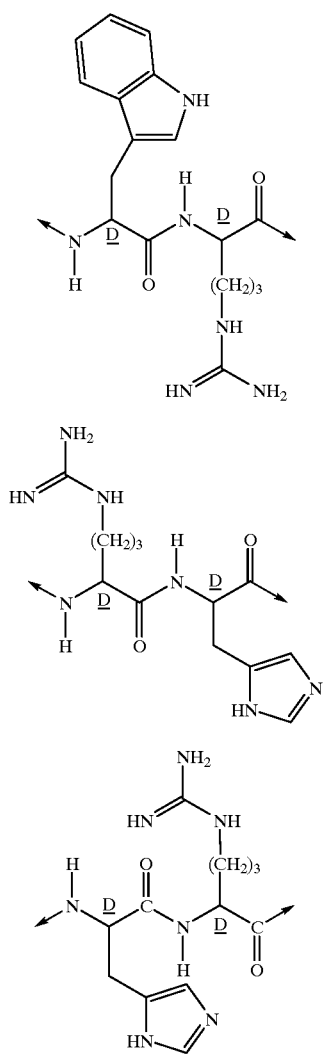
-D-Arg(Pmc)-D-Ala-, -D-Ala-D-Arg(Pmc)-, -D-Phe-D-Arg(Pmc)- and -D-Trp-D-Arg(Pmc)-.
9. A cyclic peptide according to any one of claims 1 and 2, wherein the LINKER has a structure selected from the group consisting of:
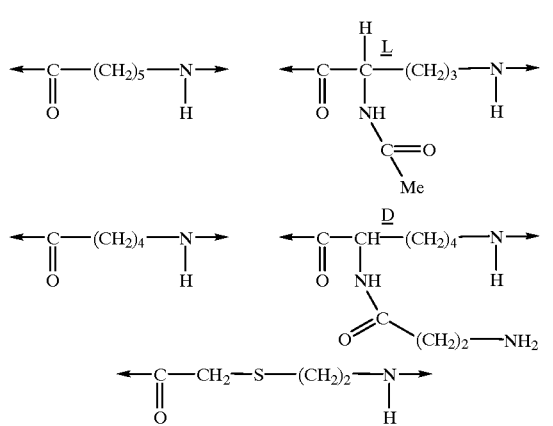
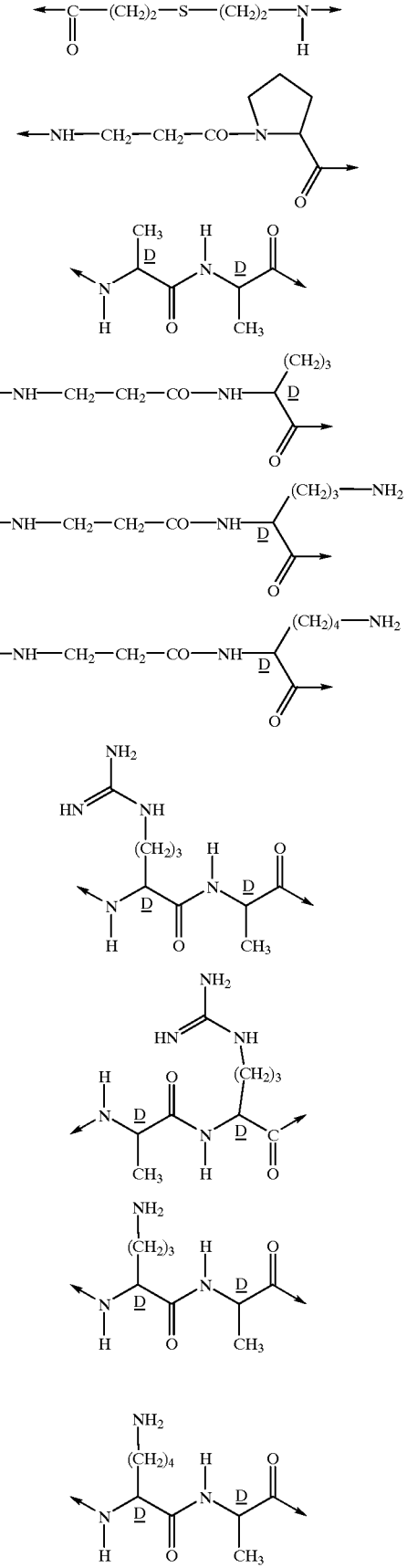

171
-continued
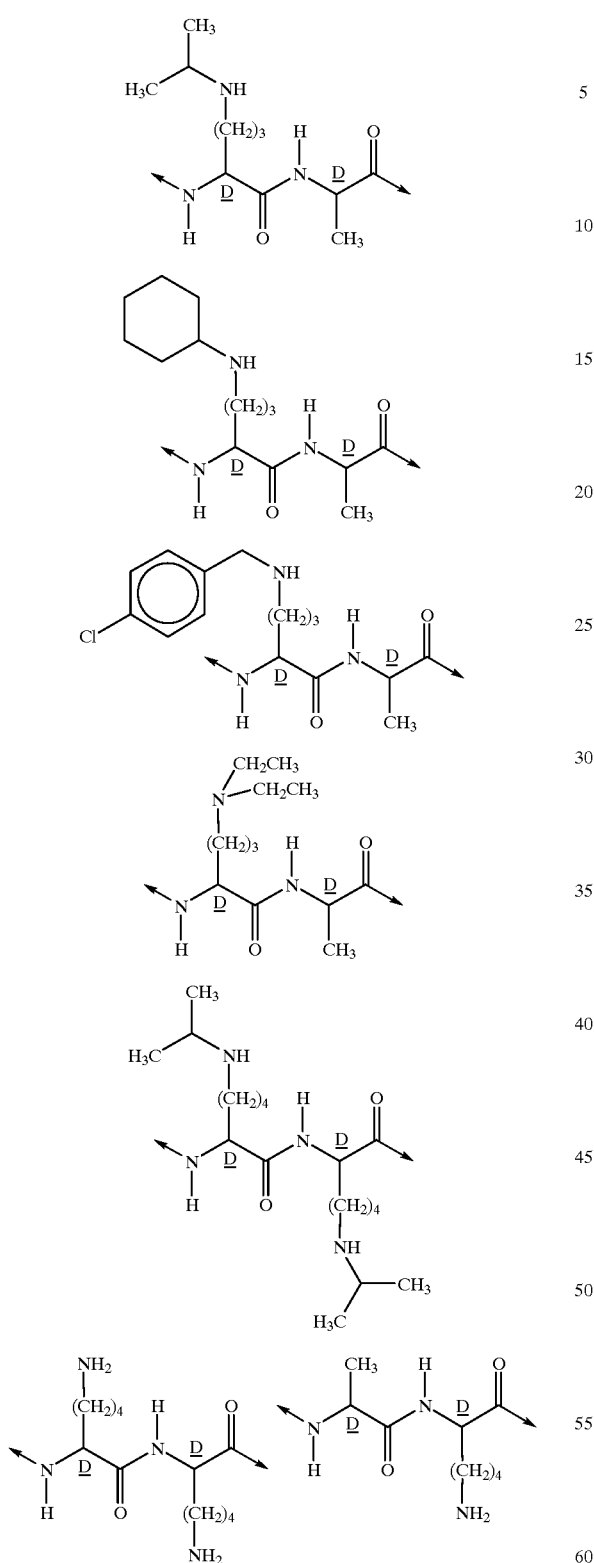
172
-continued
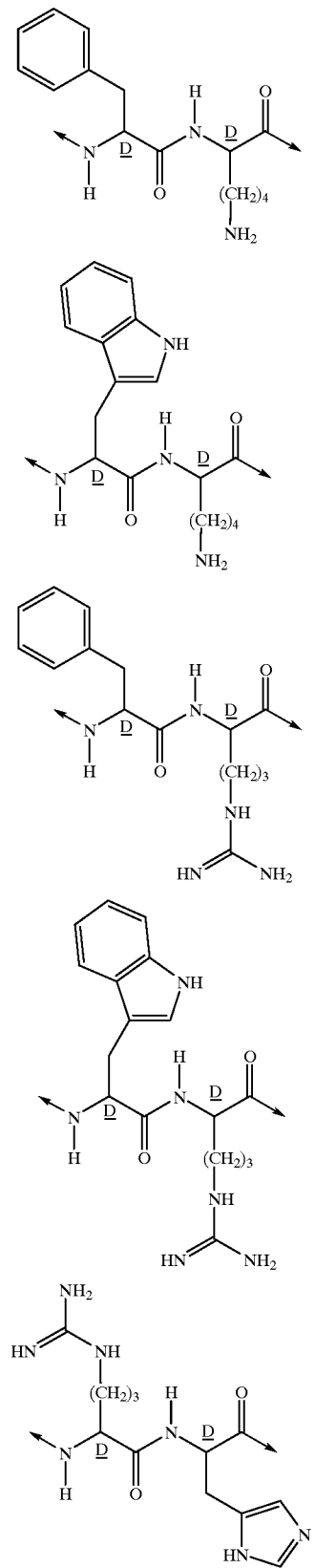

-continued
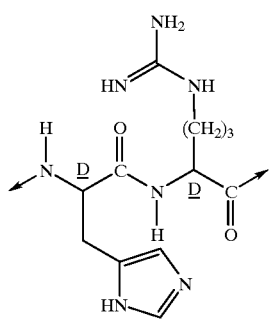
-D-Arg(Pmc)-D-Ala-, -D-Ala-D-Arg(Pmc)-, -D-Phe-D-Arg(Pmc)- and -D-Trp-D-Arg(Pmc)-.
10. A cyclic peptide according to any one of claims 1 and 2 wherein the LINKER has a structure selected from the group consisting of:
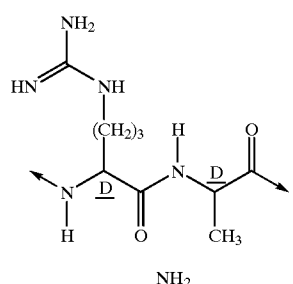
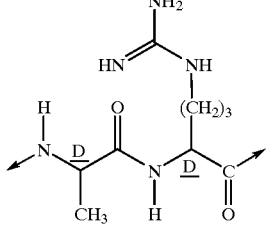
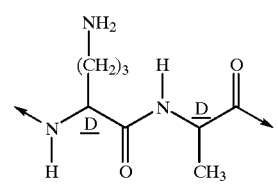
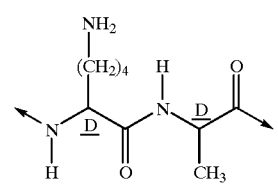
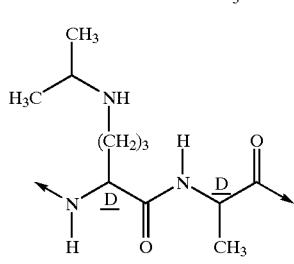
-continued
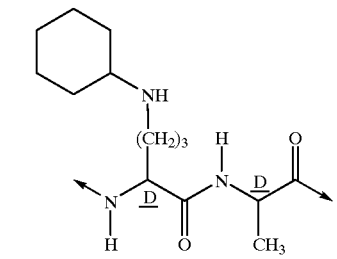
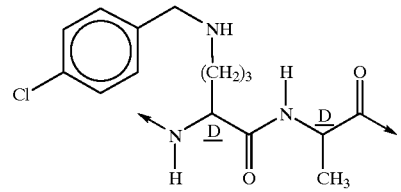
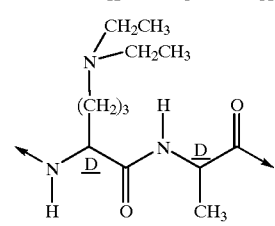
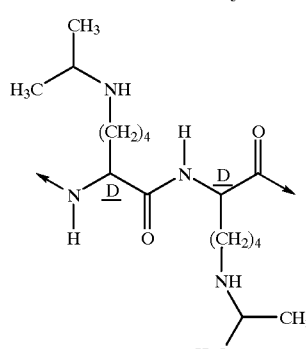
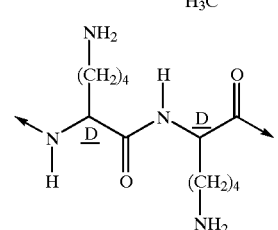
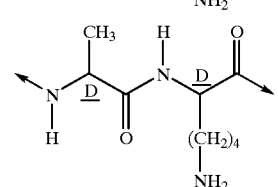
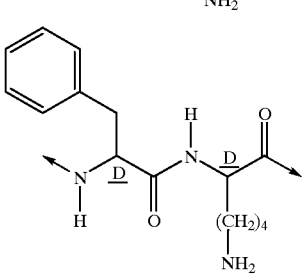

-continued or a salt thereof.

11. A cyclic peptide according to claim 1 selected from the group consisting of:

(Seq I.D. No. 3)
c(Ile-Leu-Asp-Val-NH—(CH$_2$)$_5$—CO—)

(Seq I.D. No. 5)
⎡—D-Ile-Leu-Asp-Val-NH(CH$_2$)$_5$CO—⎤

(Seq I.D. No. 11)
Ac-NH-CH(C(O)-Ile-Leu-Asp-Val)-(CH$_2$)$_4$-NH— [D-Lys analogue]

(Seq I.D. No. 13)
Ac-NH-CH(C(O)-Ile-Leu-Asp-Val)-(CH$_2$)$_3$-NH— [L-Orn analogue]

(Seq I.D. No. 9)
H$_3$C-C(CH$_3$)(CH$_3$)-CH(NH—)-C(O)-Leu-Asp-Val-NH(CH$_2$)$_5$CO—

(Seq I.D. No. 14)
Ac-NH-CH(C(O)-D-Ile-Leu-Asp-Val)-(CH$_2$)$_4$-NH— [D-Lys analogue]

(Seq I.D. No. 22)
Ac-NH-CH(C(O)-D-Ile-Leu-Asp-Val)-(CH$_2$)$_3$-NH— [L-Orn analogue]

(Seq I.D. No. 28)
⎡—D-Ile-Leu-Asp-Val-NH(CH$_2$)$_4$CO—⎤

(Seq I.D. No. 32)
⎡—MeLeu-Leu-Asp-Val-NH(CH$_2$)$_5$CO—⎤

(Seq I.D. 18)
CH$_2$CO-Ile-Leu-Asp-Val-N(piperazine)N-CH$_2$-C(O)-NH-CH$_2$—

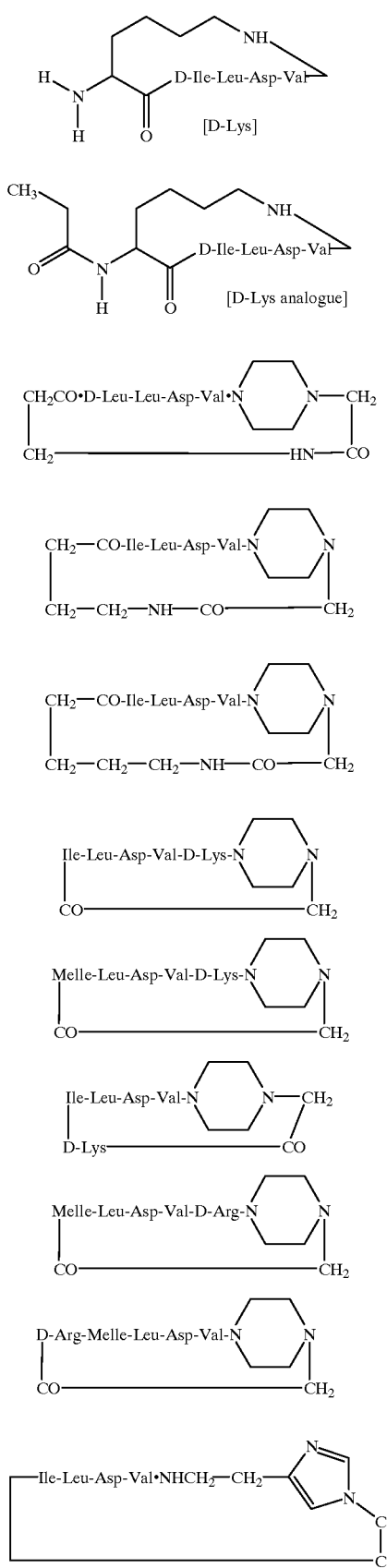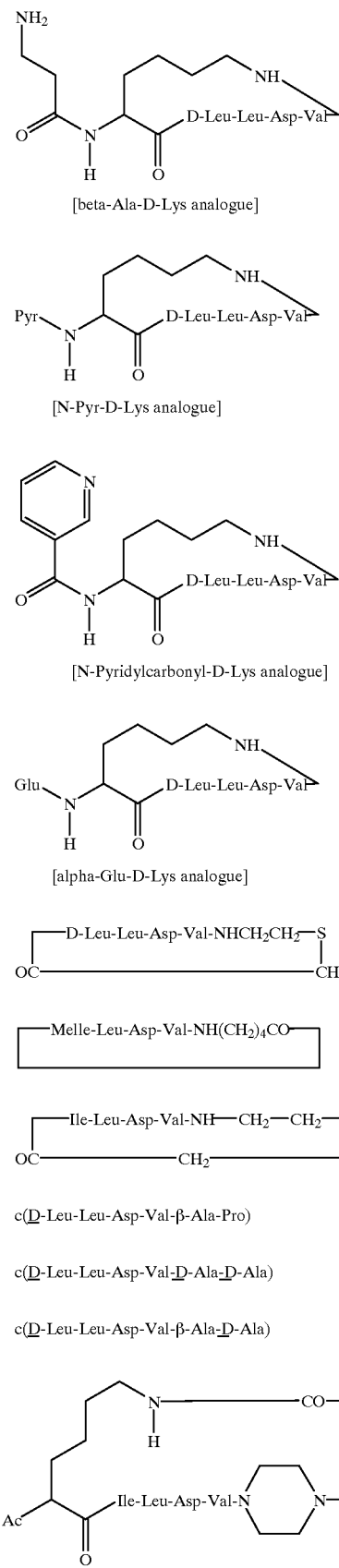

179

-continued c(MeIle-Leu-Asp-Val-β-Ala-Pro) (Seq I.D. 73)

c(MeIle-Leu-Asp-Val-β-Ala-D-Ala) (Seq I.D. 74)

c(MeIle-Leu-Asp-Val-D-Ala-D-Ala) (Seq I.D. 75)

c(MeIle-Leu-Asp-Val-β-Ala-D-Orn) (Seq I.D. 76)

c(MeIle-Leu-Asp-Val-β-Ala-D-Lys) (Seq I.D. 77)

c(MeIle-Leu-Asp-Val-D-Arg-D-Ala)

c(MeIle-Leu-Asp-Val-D-Ala-D-Arg)

c(MeIle-Leu-Asp-Val-D-Orn-D-Ala)

c(MeIle-Leu-Asp-Val-D-Lys-D-Ala)

c(MeIle-Leu-Asp-Val-D-Orn(CHMe$_2$)-D-Ala)

c(MeIle-Leu-Asp-Val-D-Orn(cyclohexyl)-D-Ala)

c(MeIle-Leu-Asp-Val-D-Orn(4-chlorobenzyl)-D-Ala)

c(MeIle-Leu-Asp-Val-D-Orn(Et$_2$)-D-Ala)

c(MeIle-Leu-Asp-Val-D-Lys(CHMe$_2$)-D-LysCHMe2))

c(MeIle-Leu-Asp-Val-D-Lys-D-Lys)

c(MeIle-Leu-Asp-Val-D-Ala-D-Lys)

c(MeIle-Leu-Asp-Val-D-Phe-D-Lys)

c(MeIle-Leu-Asp-Val-D-Trp-D-Lys)

c(MeIle-Leu-Asp-Val-D-Phe-D-Arg)

180

-continued c(MeIle-Leu-Asp-Val-D-Trp-D-Arg)

c(MeIle-Leu-Asp-Val-D-Arg-(Pmc)-D-Ala)

c(MeIle-Leu-Asp-Val-D-Ala-D-Arg(Pmc))

c(MeIle-Leu-Asp-Val-D-Phe-D-Arg(Pmc))

c(MeIle-Leu-Asp-Val-D-Trp-D-Arg(Pmc))

c(MeIle-Leu-Asp-Val-D-His-D-Lys)

c(MeIle-Leu-Asp-Val-D-Arg-D-Arg)

c(MeIle-Leu-Asp-Val-D-His-D-Arg)

c(MeIle-Leu-Asp-Val-D-Arg-D-His)

c(MeIle-Leu-Asp-Val-D-Ala-D-Orn)

c(MeIle-Leu-Asp-Val-D-Orn-D-Orn);

and salts thereof, wherein annotations in square brackets refer to the LINKER portion of the cyclic peptide.

12. A pharmaceutical composition comprising a cyclic peptide defined in claim 11, in a form suitable for parenteral administration and adapted for slow release over a period of at least 5 days.

and salts thereof, wherein annotations in square brackets refer to the LINKER portion of the cyclic peptide.

\* \* \* \* \*

SEQUENCE LISTING (1) GENERAL INFORMATION:

(iii) NUMBER OF SEQUENCES: 122

(2) INFORMATION FOR SEQ ID NO: 1:

(i) SEQUENCE CHARACTERISTICS:
      (A) LENGTH: 5 amino acids
      (B) TYPE: amino acid

```
              (C) STRANDEDNESS: single
              (D) TOPOLOGY: circular (ii) MOLECULE TYPE: peptide (ix) FEATURE:
              (A) NAME/KEY: Modified-site
              (B) LOCATION:5
              (D) OTHER INFORMATION:/product= "OTHER"
                  /note= "4-AMINO-BUTYRIC ACID"

(xi) SEQUENCE DESCRIPTION: SEQ ID NO: 1:

Ile Leu Asp Val Xaa
1               5

(2) INFORMATION FOR SEQ ID NO: 2:

(i) SEQUENCE CHARACTERISTICS:
              (A) LENGTH: 5 amino acids
              (B) TYPE: amino acid
              (C) STRANDEDNESS: single
              (D) TOPOLOGY: circular (ii) MOLECULE TYPE: peptide (ix) FEATURE:
              (A) NAME/KEY: Peptide
              (B) LOCATION:5
              (D) OTHER INFORMATION:/product= "OTHER"
                  /note= "4-AMINO-PENTANOIC ACID"

(xi) SEQUENCE DESCRIPTION: SEQ ID NO: 2:

Ile Leu Asp Val Xaa
1               5

(2) INFORMATION FOR SEQ ID NO: 3:

(i) SEQUENCE CHARACTERISTICS:
              (A) LENGTH: 5 amino acids
              (B) TYPE: amino acid
              (C) STRANDEDNESS: single
              (D) TOPOLOGY: circular (ii) MOLECULE TYPE: peptide (ix) FEATURE:
              (A) NAME/KEY: Peptide
              (B) LOCATION:5
              (D) OTHER INFORMATION:/product= "OTHER"
                  /note= "6-AMINO-HEXANOIC ACID"

(xi) SEQUENCE DESCRIPTION: SEQ ID NO: 3:

Ile Leu Asp Val Xaa
1               5

(2) INFORMATION FOR SEQ ID NO: 4:

(i) SEQUENCE CHARACTERISTICS:
              (A) LENGTH: 5 amino acids
              (B) TYPE: amino acid
              (C) STRANDEDNESS: single
              (D) TOPOLOGY: circular (ii) MOLECULE TYPE: peptide (ix) FEATURE:
              (A) NAME/KEY: Peptide
              (B) LOCATION:5
              (D) OTHER INFORMATION:/product= "OTHER"
                  /note= "7-AMINO-HEPTANOIC ACID"

(xi) SEQUENCE DESCRIPTION: SEQ ID NO: 4:
```

```
Ile Leu Asp Val Xaa
1               5

(2) INFORMATION FOR SEQ ID NO: 5:

(i) SEQUENCE CHARACTERISTICS:
        (A) LENGTH: 5 amino acids
        (B) TYPE: amino acid
        (C) STRANDEDNESS: single
        (D) TOPOLOGY: circular (ii) MOLECULE TYPE: peptide (ix) FEATURE:
        (A) NAME/KEY: Peptide
        (B) LOCATION:5
        (D) OTHER INFORMATION:/product= "OTHER"
            /note= "7-AMINO-HEXANOIC ACID"

(ix) FEATURE:
        (A) NAME/KEY: Peptide
        (B) LOCATION:1
        (D) OTHER INFORMATION:/product= "OTHER"
            /note= "D CONFIGURATION"

(xi) SEQUENCE DESCRIPTION: SEQ ID NO: 5:

Ile Leu Asp Val Xaa
1               5

(2) INFORMATION FOR SEQ ID NO: 6:

(i) SEQUENCE CHARACTERISTICS:
        (A) LENGTH: 5 amino acids
        (B) TYPE: amino acid
        (C) STRANDEDNESS: single
        (D) TOPOLOGY: circular (ii) MOLECULE TYPE: peptide (ix) FEATURE:
        (A) NAME/KEY: Peptide
        (B) LOCATION:1
        (D) OTHER INFORMATION:/product= "OTHER"
            /note= "D CONFIGURATION"

(ix) FEATURE:
        (A) NAME/KEY: Peptide
        (B) LOCATION:5
        (D) OTHER INFORMATION:/product= "OTHER"
            /note= "6-AMINO-HEXANOIC ACID"

(xi) SEQUENCE DESCRIPTION: SEQ ID NO: 6:

Leu Leu Asp Val Xaa
1               5

(2) INFORMATION FOR SEQ ID NO: 7:

(i) SEQUENCE CHARACTERISTICS:
        (A) LENGTH: 5 amino acids
        (B) TYPE: amino acid
        (C) STRANDEDNESS: single
        (D) TOPOLOGY: circular (ii) MOLECULE TYPE: peptide (ix) FEATURE:
        (A) NAME/KEY: Peptide
        (B) LOCATION:5
        (D) OTHER INFORMATION:/product= "OTHER"
            /note= "6-AMINO-HEXANOIC ACID"

(xi) SEQUENCE DESCRIPTION: SEQ ID NO: 7:

Pro Leu Asp Val Xaa
```

```
(2) INFORMATION FOR SEQ ID NO: 8:

(i) SEQUENCE CHARACTERISTICS:
        (A) LENGTH: 5 amino acids
        (B) TYPE: amino acid
        (C) STRANDEDNESS: single
        (D) TOPOLOGY: circular (ii) MOLECULE TYPE: peptide (ix) FEATURE:
        (A) NAME/KEY: Peptide
        (B) LOCATION:5
        (D) OTHER INFORMATION:/product= "OTHER"
            /note= "6-AMINO-HEXANOIC ACID"

(xi) SEQUENCE DESCRIPTION: SEQ ID NO: 8:

Gly Leu Asp Val Xaa
1               5

(2) INFORMATION FOR SEQ ID NO: 9:

(i) SEQUENCE CHARACTERISTICS:
        (A) LENGTH: 5 amino acids
        (B) TYPE: amino acid
        (C) STRANDEDNESS: single
        (D) TOPOLOGY: circular (ii) MOLECULE TYPE: peptide (ix) FEATURE:
        (A) NAME/KEY: Peptide
        (B) LOCATION:1
        (D) OTHER INFORMATION:/product= "OTHER"
            /note= "TERTIARY LEUCINE"

(ix) FEATURE:
        (A) NAME/KEY: Peptide
        (B) LOCATION:5
        (D) OTHER INFORMATION:/product= "OTHER"
            /note= "6-AMINO-HEXANOIC ACID"

(xi) SEQUENCE DESCRIPTION: SEQ ID NO: 9:

Xaa Leu Asp Val Xaa
1               5

(2) INFORMATION FOR SEQ ID NO: 10:

(i) SEQUENCE CHARACTERISTICS:
        (A) LENGTH: 5 amino acids
        (B) TYPE: amino acid
        (C) STRANDEDNESS: single
        (D) TOPOLOGY: circular (ii) MOLECULE TYPE: peptide (ix) FEATURE:
        (A) NAME/KEY: Peptide
        (B) LOCATION:1
        (D) OTHER INFORMATION:/product= "OTHER"
            /note= "TERT-BUTYL-ALANINE"

(ix) FEATURE:
        (A) NAME/KEY: Peptide
        (B) LOCATION:5
        (D) OTHER INFORMATION:/product= "OTHER"
            /note= "6-AMINO-HEXANOIC ACID"

(xi) SEQUENCE DESCRIPTION: SEQ ID NO: 10:

Xaa Leu Asp Val Xaa
1               5
```

(2) INFORMATION FOR SEQ ID NO: 11:

(i) SEQUENCE CHARACTERISTICS:
        (A) LENGTH: 5 amino acids
        (B) TYPE: amino acid
        (C) STRANDEDNESS: single
        (D) TOPOLOGY: circular (ii) MOLECULE TYPE: peptide (ix) FEATURE:
        (A) NAME/KEY: Peptide
        (B) LOCATION:1
        (D) OTHER INFORMATION:/product= "OTHER"
            /note= "N-ACETYL-D-LYSINE"

(xi) SEQUENCE DESCRIPTION: SEQ ID NO: 11:

Xaa Ile Leu Asp Val
1               5

(2) INFORMATION FOR SEQ ID NO: 12:

(i) SEQUENCE CHARACTERISTICS:
        (A) LENGTH: 5 amino acids
        (B) TYPE: amino acid
        (C) STRANDEDNESS: single
        (D) TOPOLOGY: circular (ii) MOLECULE TYPE: peptide (ix) FEATURE:
        (A) NAME/KEY: Peptide
        (B) LOCATION:1
        (D) OTHER INFORMATION:/product= "OTHER"
            /note= "N-ACETYL-D-ORNITHINE"

(xi) SEQUENCE DESCRIPTION: SEQ ID NO: 12:

Xaa Ile Leu Asp Val
1               5

(2) INFORMATION FOR SEQ ID NO: 13:

(i) SEQUENCE CHARACTERISTICS:
        (A) LENGTH: 5 amino acids
        (B) TYPE: amino acid
        (C) STRANDEDNESS: single
        (D) TOPOLOGY: circular (ii) MOLECULE TYPE: peptide (ix) FEATURE:
        (A) NAME/KEY: Peptide
        (B) LOCATION:1
        (D) OTHER INFORMATION:/product= "OTHER"
            /note= "N-ACETYL-ORNITHINE"

(xi) SEQUENCE DESCRIPTION: SEQ ID NO: 13:

Xaa Ile Leu Asp Val
1               5

(2) INFORMATION FOR SEQ ID NO: 14:

(i) SEQUENCE CHARACTERISTICS:
        (A) LENGTH: 5 amino acids
        (B) TYPE: amino acid
        (C) STRANDEDNESS: single
        (D) TOPOLOGY: circular (ii) MOLECULE TYPE: peptide (ix) FEATURE:

```
            (A) NAME/KEY: Peptide
            (B) LOCATION:1
            (D) OTHER INFORMATION:/product= "OTHER"
                /note= "N-ACETYL-D-LYSINE"

(ix) FEATURE:
            (A) NAME/KEY: Peptide
            (B) LOCATION:2
            (D) OTHER INFORMATION:/product= "OTHER"
                /note= "D CONFIGURATION"

(xi) SEQUENCE DESCRIPTION: SEQ ID NO: 14:

Xaa Ile Leu Asp Val
1               5

(2) INFORMATION FOR SEQ ID NO: 15:

(i) SEQUENCE CHARACTERISTICS:
            (A) LENGTH: 5 amino acids
            (B) TYPE: amino acid
            (C) STRANDEDNESS: single
            (D) TOPOLOGY: circular (ii) MOLECULE TYPE: peptide (ix) FEATURE:
            (A) NAME/KEY: Peptide
            (B) LOCATION:5
            (D) OTHER INFORMATION:/product= "OTHER"
                /note= "4-AMINOMETHYL-BENZOIC ACID"

(xi) SEQUENCE DESCRIPTION: SEQ ID NO: 15:

Ile Leu Asp Val Xaa
1               5

(2) INFORMATION FOR SEQ ID NO: 16:

(i) SEQUENCE CHARACTERISTICS:
            (A) LENGTH: 5 amino acids
            (B) TYPE: amino acid
            (C) STRANDEDNESS: single
            (D) TOPOLOGY: circular (ii) MOLECULE TYPE: peptide (ix) FEATURE:
            (A) NAME/KEY: Peptide
            (B) LOCATION:5
            (D) OTHER INFORMATION:/product= "OTHER"
                /note= "(4-(2-AMINOETHYL)-IMIDAZOL-1-YL)-
                ACETIC ACID"

(xi) SEQUENCE DESCRIPTION: SEQ ID NO: 16:

Ile Leu Asp Val Xaa
1               5

(2) INFORMATION FOR SEQ ID NO: 17:

(i) SEQUENCE CHARACTERISTICS:
            (A) LENGTH: 5 amino acids
            (B) TYPE: amino acid
            (C) STRANDEDNESS: single
            (D) TOPOLOGY: circular (ii) MOLECULE TYPE: peptide (ix) FEATURE:
            (A) NAME/KEY: Peptide
            (B) LOCATION:1
            (D) OTHER INFORMATION:/product= "OTHER"
                /note= "D CONFIGURATION"

(ix) FEATURE:
```

```
            (A) NAME/KEY: Peptide
            (B) LOCATION:5
            (D) OTHER INFORMATION:/product= "OTHER"
                /note= "PIPERAZINYL-1-YL-ACETIC ACID"

(xi) SEQUENCE DESCRIPTION: SEQ ID NO: 17:

Leu Leu Asp Val Xaa
1               5

(2) INFORMATION FOR SEQ ID NO: 18:

(i) SEQUENCE CHARACTERISTICS:
        (A) LENGTH: 6 amino acids
        (B) TYPE: amino acid
        (C) STRANDEDNESS: single
        (D) TOPOLOGY: circular (ii) MOLECULE TYPE: peptide (ix) FEATURE:
        (A) NAME/KEY: Peptide
        (B) LOCATION:5
        (D) OTHER INFORMATION:/product= "OTHER"
            /note= "PIPERAZINYL-1-YL-ACETIC ACID"

(ix) FEATURE:
        (A) NAME/KEY: Peptide
        (B) LOCATION:6
        (D) OTHER INFORMATION:/product= "bAla"

(xi) SEQUENCE DESCRIPTION: SEQ ID NO: 18:

Ile Leu Asp Val Xaa Ala
1               5

(2) INFORMATION FOR SEQ ID NO: 19:

(i) SEQUENCE CHARACTERISTICS:
        (A) LENGTH: 6 amino acids
        (B) TYPE: amino acid
        (C) STRANDEDNESS: single
        (D) TOPOLOGY: circular (ii) MOLECULE TYPE: peptide (ix) FEATURE:
        (A) NAME/KEY: Peptide
        (B) LOCATION:1
        (D) OTHER INFORMATION:/product= "OTHER"
            /note= "D CONFIGURATION"

(ix) FEATURE:
        (A) NAME/KEY: Peptide
        (B) LOCATION:5
        (D) OTHER INFORMATION:/product= "OTHER"
            /note= "PIPERAZIN-1YL-ACETIC ACID"

(ix) FEATURE:
        (A) NAME/KEY: Peptide
        (B) LOCATION:6
        (D) OTHER INFORMATION:/product= "bAla"

(xi) SEQUENCE DESCRIPTION: SEQ ID NO: 19:

Leu Leu Asp Val Xaa Ala
1               5

(2) INFORMATION FOR SEQ ID NO: 20:

(i) SEQUENCE CHARACTERISTICS:
        (A) LENGTH: 5 amino acids
        (B) TYPE: amino acid
        (C) STRANDEDNESS: single
        (D) TOPOLOGY: circular
```

```
       (ii) MOLECULE TYPE: peptide (ix) FEATURE:
            (A) NAME/KEY: Peptide
            (B) LOCATION:1
            (D) OTHER INFORMATION:/product= "OTHER"
                /note= "N-ACETYL-D-LYSINE"

(xi) SEQUENCE DESCRIPTION: SEQ ID NO: 20:

Xaa Ile Leu Asp Val
1               5

(2) INFORMATION FOR SEQ ID NO: 21:

(i) SEQUENCE CHARACTERISTICS:
            (A) LENGTH: 5 amino acids
            (B) TYPE: amino acid
            (C) STRANDEDNESS: single
            (D) TOPOLOGY: circular (ii) MOLECULE TYPE: peptide (ix) FEATURE:
            (A) NAME/KEY: Peptide
            (B) LOCATION:1
            (D) OTHER INFORMATION:/product= "OTHER"
                /note= "N-ACETYL-ORNITHINE"

(ix) FEATURE:
            (A) NAME/KEY: Peptide
            (B) LOCATION:2
            (D) OTHER INFORMATION:/product= "OTHER"
                /note= "D-CONFIGURATION"

(xi) SEQUENCE DESCRIPTION: SEQ ID NO: 21:

Xaa Ile Leu Asp Val
1               5

(2) INFORMATION FOR SEQ ID NO: 22:

(i) SEQUENCE CHARACTERISTICS:
            (A) LENGTH: 5 amino acids
            (B) TYPE: amino acid
            (C) STRANDEDNESS: single
            (D) TOPOLOGY: circular (ii) MOLECULE TYPE: peptide (ix) FEATURE:
            (A) NAME/KEY: Peptide
            (B) LOCATION:1
            (D) OTHER INFORMATION:/product= "OTHER"
                /note= "N-ACETYL-D-ORNITHINE"

(ix) FEATURE:
            (A) NAME/KEY: Peptide
            (B) LOCATION:2
            (D) OTHER INFORMATION:/product= "OTHER"
                /note= "D-CONFIGURATION"

(xi) SEQUENCE DESCRIPTION: SEQ ID NO: 22:

Xaa Ile Leu Asp Val
1               5

(2) INFORMATION FOR SEQ ID NO: 23:

(i) SEQUENCE CHARACTERISTICS:
            (A) LENGTH: 5 amino acids
            (B) TYPE: amino acid
            (C) STRANDEDNESS: single
            (D) TOPOLOGY: circular (ii) MOLECULE TYPE: peptide
```

```
        (ix) FEATURE:
              (A) NAME/KEY: Peptide
              (B) LOCATION:1
              (D) OTHER INFORMATION:/product= "OTHER"
                    /note= "N-ACETYL-LYSINE"

(ix) FEATURE:
              (A) NAME/KEY: Peptide
              (B) LOCATION:2
              (D) OTHER INFORMATION:/product= "OTHER"
                    /note= "D-CONFIGURATION"

(xi) SEQUENCE DESCRIPTION: SEQ ID NO: 23:

Xaa Ile Leu Asp Val
1               5

(2) INFORMATION FOR SEQ ID NO: 24:

(i) SEQUENCE CHARACTERISTICS:
              (A) LENGTH: 5 amino acids
              (B) TYPE: amino acid
              (C) STRANDEDNESS: single
              (D) TOPOLOGY: circular (ii) MOLECULE TYPE: peptide (ix) FEATURE:
              (A) NAME/KEY: Peptide
              (B) LOCATION:1
              (D) OTHER INFORMATION:/product= "OTHER"
                    /note= "N-ACETYL-2,4-DIAMINO-BUTYRIC ACID"

(ix) FEATURE:
              (A) NAME/KEY: Peptide
              (B) LOCATION:2
              (D) OTHER INFORMATION:/product= "OTHER"
                    /note= "D-CONFIGURATION"

(xi) SEQUENCE DESCRIPTION: SEQ ID NO: 24:

Xaa Ile Leu Asp Val
1               5

(2) INFORMATION FOR SEQ ID NO: 25:

(i) SEQUENCE CHARACTERISTICS:
              (A) LENGTH: 5 amino acids
              (B) TYPE: amino acid
              (C) STRANDEDNESS: single
              (D) TOPOLOGY: circular (ii) MOLECULE TYPE: peptide (ix) FEATURE:
              (A) NAME/KEY: Peptide
              (B) LOCATION:1
              (D) OTHER INFORMATION:/product= "OTHER"
                    /note= "N-ACETYL-2,4-DIAMINO-BUTYRIC ACID"

(xi) SEQUENCE DESCRIPTION: SEQ ID NO: 25:

Xaa Ile Leu Asp Val
1               5

(2) INFORMATION FOR SEQ ID NO: 26:

(i) SEQUENCE CHARACTERISTICS:
              (A) LENGTH: 5 amino acids
              (B) TYPE: amino acid
              (C) STRANDEDNESS: single
              (D) TOPOLOGY: circular (ii) MOLECULE TYPE: peptide
```

```
    (ix) FEATURE:
          (A) NAME/KEY: Peptide
          (B) LOCATION:1
          (D) OTHER INFORMATION:/product= "OTHER"
              /note= "N-ACETYL-2,4-DIAMINO-BUTYRIC ACID, D
              CONFIGURATION"

(xi) SEQUENCE DESCRIPTION: SEQ ID NO: 26:

Xaa Ile Leu Asp Val
1               5

(2) INFORMATION FOR SEQ ID NO: 27:

(i) SEQUENCE CHARACTERISTICS:
         (A) LENGTH: 5 amino acids
         (B) TYPE: amino acid
         (C) STRANDEDNESS: single
         (D) TOPOLOGY: circular (ii) MOLECULE TYPE: peptide (ix) FEATURE:
         (A) NAME/KEY: Peptide
         (B) LOCATION:1
         (D) OTHER INFORMATION:/product= "OTHER"
             /note= "N-ACETYL-2,4-DIAMINO-BUTYRIC ACID, D
             CONFIGURATION"

(ix) FEATURE:
         (A) NAME/KEY: Peptide
         (B) LOCATION:2
         (D) OTHER INFORMATION:/product= "OTHER"
             /note= "D CONFIGURATION"

(xi) SEQUENCE DESCRIPTION: SEQ ID NO: 27:

Xaa Leu Leu Asp Val
1               5

(2) INFORMATION FOR SEQ ID NO: 28:

(i) SEQUENCE CHARACTERISTICS:
         (A) LENGTH: 5 amino acids
         (B) TYPE: amino acid
         (C) STRANDEDNESS: single
         (D) TOPOLOGY: circular (ii) MOLECULE TYPE: peptide (ix) FEATURE:
         (A) NAME/KEY: Peptide
         (B) LOCATION:1
         (D) OTHER INFORMATION:/product= "OTHER"
             /note= "D CONFIGURATION"

(ix) FEATURE:
         (A) NAME/KEY: Peptide
         (B) LOCATION:5
         (D) OTHER INFORMATION:/product= "OTHER"
             /note= "5-AMINO-PENTANOIC ACID"

(xi) SEQUENCE DESCRIPTION: SEQ ID NO: 28:

Ile Leu Asp Val Xaa
1               5

(2) INFORMATION FOR SEQ ID NO: 29:

(i) SEQUENCE CHARACTERISTICS:
         (A) LENGTH: 5 amino acids
         (B) TYPE: amino acid
         (C) STRANDEDNESS: single
         (D) TOPOLOGY: circular (ii) MOLECULE TYPE: peptide
```

-continued

```
    (ix) FEATURE:
         (A) NAME/KEY: Peptide
         (B) LOCATION:1
         (D) OTHER INFORMATION:/product= "OTHER"
              /note= "D CONFIGURATION"

(ix) FEATURE:
         (A) NAME/KEY: Peptide
         (B) LOCATION:5
         (D) OTHER INFORMATION:/product= "OTHER"
              /note= "5-AMINO-PENTANOIC ACID"

(xi) SEQUENCE DESCRIPTION: SEQ ID NO: 29:

Leu Leu Asp Val Xaa
1               5

(2) INFORMATION FOR SEQ ID NO: 30:

(i) SEQUENCE CHARACTERISTICS:
         (A) LENGTH: 5 amino acids
         (B) TYPE: amino acid
         (C) STRANDEDNESS: single
         (D) TOPOLOGY: circular (ii) MOLECULE TYPE: peptide (ix) FEATURE:
         (A) NAME/KEY: Peptide
         (B) LOCATION:1
         (D) OTHER INFORMATION:/product= "OTHER"
              /note= "D CONFIGURATION"

(ix) FEATURE:
         (A) NAME/KEY: Peptide
         (B) LOCATION:5
         (D) OTHER INFORMATION:/product= "OTHER"
              /note= "6-AMINO-HEXANOIC ACID"

(xi) SEQUENCE DESCRIPTION: SEQ ID NO: 30:

Val Leu Asp Val Xaa
1               5

(2) INFORMATION FOR SEQ ID NO: 31:

(i) SEQUENCE CHARACTERISTICS:
         (A) LENGTH: 5 amino acids
         (B) TYPE: amino acid
         (C) STRANDEDNESS: single
         (D) TOPOLOGY: circular (ii) MOLECULE TYPE: peptide (ix) FEATURE:
         (A) NAME/KEY: Peptide
         (B) LOCATION:1
         (D) OTHER INFORMATION:/product= "OTHER"
              /note= "N-METHYL-ALANINE"

(ix) FEATURE:
         (A) NAME/KEY: Peptide
         (B) LOCATION:5
         (D) OTHER INFORMATION:/product= "OTHER"
              /note= "6-AMINO-HEXANOIC ACID"

(xi) SEQUENCE DESCRIPTION: SEQ ID NO: 31:

Xaa Leu Asp Val Xaa
1               5

(2) INFORMATION FOR SEQ ID NO: 32:

(i) SEQUENCE CHARACTERISTICS:
         (A) LENGTH: 5 amino acids
```

```
            (B) TYPE: amino acid
            (C) STRANDEDNESS: single
            (D) TOPOLOGY: circular (ii) MOLECULE TYPE: peptide (ix) FEATURE:
            (A) NAME/KEY: Peptide
            (B) LOCATION:1
            (D) OTHER INFORMATION:/product= "OTHER"
                /note= "N-METHYL-LEUCINE"

(ix) FEATURE:
            (A) NAME/KEY: Peptide
            (B) LOCATION:5
            (D) OTHER INFORMATION:/product= "OTHER"
                /note= "6-AMINO-HEXANOIC ACID"

(xi) SEQUENCE DESCRIPTION: SEQ ID NO: 32:

Xaa Leu Ala Val Xaa
1               5

(2) INFORMATION FOR SEQ ID NO: 33:

(i) SEQUENCE CHARACTERISTICS:
            (A) LENGTH: 5 amino acids
            (B) TYPE: amino acid
            (C) STRANDEDNESS: single
            (D) TOPOLOGY: circular (ii) MOLECULE TYPE: peptide (ix) FEATURE:
            (A) NAME/KEY: Peptide
            (B) LOCATION:2
            (D) OTHER INFORMATION:/product= "OTHER"
                /note= "TERT-BUTYL-ALANINE"

(ix) FEATURE:
            (A) NAME/KEY: Peptide
            (B) LOCATION:5
            (D) OTHER INFORMATION:/product= "OTHER"
                /note= "5-AMINO-HEXANOIC ACID"

(xi) SEQUENCE DESCRIPTION: SEQ ID NO: 33:

Ile Xaa Asp Val Xaa
1               5

(2) INFORMATION FOR SEQ ID NO: 34:

(i) SEQUENCE CHARACTERISTICS:
            (A) LENGTH: 5 amino acids
            (B) TYPE: amino acid
            (C) STRANDEDNESS: single
            (D) TOPOLOGY: circular (ii) MOLECULE TYPE: peptide (ix) FEATURE:
            (A) NAME/KEY: Peptide
            (B) LOCATION:5
            (D) OTHER INFORMATION:/product= "OTHER"
                /note= "5-AMINO-PENTANOIC ACID"

(xi) SEQUENCE DESCRIPTION: SEQ ID NO: 34:

Ile Ile Asp Val Xaa
1               5

(2) INFORMATION FOR SEQ ID NO: 35:

(i) SEQUENCE CHARACTERISTICS:
            (A) LENGTH: 5 amino acids
            (B) TYPE: amino acid
```

(C) STRANDEDNESS: single
            (D) TOPOLOGY: circular (ii) MOLECULE TYPE: peptide (ix) FEATURE:
            (A) NAME/KEY: Peptide
            (B) LOCATION:2
            (D) OTHER INFORMATION:/product= "Nle"

(ix) FEATURE:
            (A) NAME/KEY: Peptide
            (B) LOCATION:5
            (D) OTHER INFORMATION:/product= "OTHER"
                /note= "5-AMINO-PENTANOIC ACID"

(xi) SEQUENCE DESCRIPTION: SEQ ID NO: 35:

Ile Leu Asp Val Xaa
1               5

(2) INFORMATION FOR SEQ ID NO: 36:

(i) SEQUENCE CHARACTERISTICS:
            (A) LENGTH: 5 amino acids
            (B) TYPE: amino acid
            (C) STRANDEDNESS: single
            (D) TOPOLOGY: circular (ii) MOLECULE TYPE: peptide (ix) FEATURE:
            (A) NAME/KEY: Peptide
            (B) LOCATION:5
            (D) OTHER INFORMATION:/note= "5-AMINO-PENTANOIC
                ACID"

(xi) SEQUENCE DESCRIPTION: SEQ ID NO: 36:

Ile Val Asp Val Xaa
1               5

(2) INFORMATION FOR SEQ ID NO: 37:

(i) SEQUENCE CHARACTERISTICS:
            (A) LENGTH: 5 amino acids
            (B) TYPE: amino acid
            (C) STRANDEDNESS: single
            (D) TOPOLOGY: circular (ii) MOLECULE TYPE: peptide (ix) FEATURE:
            (A) NAME/KEY: Peptide
            (B) LOCATION:2
            (D) OTHER INFORMATION:/product= "OTHER"
                /note= "CYCLOHEXYL-ALANINE"

(ix) FEATURE:
            (A) NAME/KEY: Peptide
            (B) LOCATION:5
            (D) OTHER INFORMATION:/product= "OTHER"
                /note= "5-AMINO-PENTANOIC ACID"

(xi) SEQUENCE DESCRIPTION: SEQ ID NO: 37:

Ile Xaa Asp Val Xaa
1               5

(2) INFORMATION FOR SEQ ID NO: 38:

(i) SEQUENCE CHARACTERISTICS:
            (A) LENGTH: 5 amino acids
            (B) TYPE: amino acid
            (C) STRANDEDNESS: single
            (D) TOPOLOGY: circular

```
        (ii) MOLECULE TYPE: peptide (ix) FEATURE:
             (A) NAME/KEY: Peptide
             (B) LOCATION:2
             (D) OTHER INFORMATION:/product= "OTHER"
                   /note= "TERT-LEUCINE"

(ix) FEATURE:
             (A) NAME/KEY: Peptide
             (B) LOCATION:5
             (D) OTHER INFORMATION:/product= "OTHER"
                   /note= "5-AMINO-PENTANOIC ACID"

(xi) SEQUENCE DESCRIPTION: SEQ ID NO: 38:

Ile Xaa Asp Val Xaa
1               5

(2) INFORMATION FOR SEQ ID NO: 39:

(i) SEQUENCE CHARACTERISTICS:
             (A) LENGTH: 5 amino acids
             (B) TYPE: amino acid
             (C) STRANDEDNESS: single
             (D) TOPOLOGY: circular (ii) MOLECULE TYPE: peptide (ix) FEATURE:
             (A) NAME/KEY: Peptide
             (B) LOCATION:1
             (D) OTHER INFORMATION:/product= "OTHER"
                   /note= "D CONFIGURATION"

(ix) FEATURE:
             (A) NAME/KEY: Peptide
             (B) LOCATION:2
             (D) OTHER INFORMATION:/product= "OTHER"
                   /note= "D CONFIGURATION"

(xi) SEQUENCE DESCRIPTION: SEQ ID NO: 39:

Lys Ile Leu Asp Val
1               5

(2) INFORMATION FOR SEQ ID NO: 40:

(i) SEQUENCE CHARACTERISTICS:
             (A) LENGTH: 5 amino acids
             (B) TYPE: amino acid
             (C) STRANDEDNESS: single
             (D) TOPOLOGY: circular (ii) MOLECULE TYPE: peptide (ix) FEATURE:
             (A) NAME/KEY: Peptide
             (B) LOCATION:1
             (D) OTHER INFORMATION:/product= "OTHER"
                   /note= "Z-D-LYSINE"

(ix) FEATURE:
             (A) NAME/KEY: Peptide
             (B) LOCATION:2
             (D) OTHER INFORMATION:/product= "OTHER"
                   /note= "D-CONFIGURATION"

(xi) SEQUENCE DESCRIPTION: SEQ ID NO: 40:

Xaa Ile Leu Asp Val
1               5

(2) INFORMATION FOR SEQ ID NO: 41:
```

(i) SEQUENCE CHARACTERISTICS:
        (A) LENGTH: 5 amino acids
        (B) TYPE: amino acid
        (C) STRANDEDNESS: single
        (D) TOPOLOGY: circular (ii) MOLECULE TYPE: peptide (ix) FEATURE:
        (A) NAME/KEY: Peptide
        (B) LOCATION:1
        (D) OTHER INFORMATION:/product= "OTHER"
            /note= "N(CH3-CH2-CO)-LYSINE, D
            CONFIGURATION"

(ix) FEATURE:
        (A) NAME/KEY: Peptide
        (B) LOCATION:2
        (D) OTHER INFORMATION:/product= "OTHER"
            /note= "D-CONFIGURATION"

(xi) SEQUENCE DESCRIPTION: SEQ ID NO: 41:

Xaa Ile Leu Asp Val
1               5

(2) INFORMATION FOR SEQ ID NO: 42:

(i) SEQUENCE CHARACTERISTICS:
        (A) LENGTH: 5 amino acids
        (B) TYPE: amino acid
        (C) STRANDEDNESS: single
        (D) TOPOLOGY: circular (ii) MOLECULE TYPE: peptide (ix) FEATURE:
        (A) NAME/KEY: Peptide
        (B) LOCATION:1
        (D) OTHER INFORMATION:/product= "OTHER"
            /note= "N(HOOC-CH2-CH2-CO)-LYSINE, D
            CONFIGURATION"

(ix) FEATURE:
        (A) NAME/KEY: Peptide
        (B) LOCATION:2
        (D) OTHER INFORMATION:/product= "OTHER"
            /note= "D CONFIGURATION"

(xi) SEQUENCE DESCRIPTION: SEQ ID NO: 42:

Xaa Ile Leu Asp Val
1               5

(2) INFORMATION FOR SEQ ID NO: 43:

(i) SEQUENCE CHARACTERISTICS:
        (A) LENGTH: 5 amino acids
        (B) TYPE: amino acid
        (C) STRANDEDNESS: single
        (D) TOPOLOGY: circular (ii) MOLECULE TYPE: peptide (ix) FEATURE:
        (A) NAME/KEY: Peptide
        (B) LOCATION:1
        (D) OTHER INFORMATION:/product= "OTHER"
            /note= "N(Me2.CH.CO)-LYSINE, D CONFIGURATION"

(ix) FEATURE:
        (A) NAME/KEY: Peptide
        (B) LOCATION:2
        (D) OTHER INFORMATION:/product= "OTHER"
            /note= "D CONFIGURATION"

(xi) SEQUENCE DESCRIPTION: SEQ ID NO: 43:

```
Xaa Ile Leu Asp Val
1               5

(2) INFORMATION FOR SEQ ID NO: 44:

(i) SEQUENCE CHARACTERISTICS:
        (A) LENGTH: 5 amino acids
        (B) TYPE: amino acid
        (C) STRANDEDNESS: single
        (D) TOPOLOGY: circular (ii) MOLECULE TYPE: peptide (ix) FEATURE:
        (A) NAME/KEY: Peptide
        (B) LOCATION:1
        (D) OTHER INFORMATION:/product= "OTHER"
            /note= "N(H2N.CH2.CH2.CO)-LYSINE, D
            CONFIGURATION"

(ix) FEATURE:
        (A) NAME/KEY: Peptide
        (B) LOCATION:2
        (D) OTHER INFORMATION:/product= "OTHER"
            /note= "D CONFIGURATION"

(xi) SEQUENCE DESCRIPTION: SEQ ID NO: 44:

Xaa Leu Leu Asp Val
1               5

(2) INFORMATION FOR SEQ ID NO: 45:

(i) SEQUENCE CHARACTERISTICS:
        (A) LENGTH: 5 amino acids
        (B) TYPE: amino acid
        (C) STRANDEDNESS: single
        (D) TOPOLOGY: circular (ii) MOLECULE TYPE: peptide (ix) FEATURE:
        (A) NAME/KEY: Peptide
        (B) LOCATION:1
        (D) OTHER INFORMATION:/product= "OTHER"
            /note= "N(DIETHYL)-LYSINE, D CONFIGURATION"

(ix) FEATURE:
        (A) NAME/KEY: Peptide
        (B) LOCATION:2
        (D) OTHER INFORMATION:/product= "OTHER"
            /note= "D CONFIGURATION"

(xi) SEQUENCE DESCRIPTION: SEQ ID NO: 45:

Xaa Leu Leu Asp Val
1               5

(2) INFORMATION FOR SEQ ID NO: 46:

(i) SEQUENCE CHARACTERISTICS:
        (A) LENGTH: 5 amino acids
        (B) TYPE: amino acid
        (C) STRANDEDNESS: single
        (D) TOPOLOGY: circular (ii) MOLECULE TYPE: peptide (ix) FEATURE:
        (A) NAME/KEY: Peptide
        (B) LOCATION:1
        (D) OTHER INFORMATION:/product= "OTHER"
            /note= "N-BENZYL-LYSINE, D CONFIGURATION"

(ix) FEATURE:
```

```
            (A) NAME/KEY: Peptide
            (B) LOCATION:2
            (D) OTHER INFORMATION:/product= "OTHER"
                /note= "D CONFIGURATION"

(xi) SEQUENCE DESCRIPTION: SEQ ID NO: 46:

Xaa Leu Leu Asp Val
1               5

(2) INFORMATION FOR SEQ ID NO: 47:

(i) SEQUENCE CHARACTERISTICS:
        (A) LENGTH: 5 amino acids
        (B) TYPE: amino acid
        (C) STRANDEDNESS: single
        (D) TOPOLOGY: circular (ii) MOLECULE TYPE: peptide (ix) FEATURE:
        (A) NAME/KEY: Peptide
        (B) LOCATION:1
        (D) OTHER INFORMATION:/product= "OTHER"
            /note= "N(PYRIDYL-CARBONYL)-LYSINE, D
            CONFIGURATION"

(ix) FEATURE:
        (A) NAME/KEY: Peptide
        (B) LOCATION:2
        (D) OTHER INFORMATION:/product= "OTHER"
            /note= "D CONFIGURATION"

(xi) SEQUENCE DESCRIPTION: SEQ ID NO: 47:

Xaa Leu Leu Asp Val
1               5

(2) INFORMATION FOR SEQ ID NO: 48:

(i) SEQUENCE CHARACTERISTICS:
        (A) LENGTH: 5 amino acids
        (B) TYPE: amino acid
        (C) STRANDEDNESS: single
        (D) TOPOLOGY: circular (ii) MOLECULE TYPE: peptide (ix) FEATURE:
        (A) NAME/KEY: Peptide
        (B) LOCATION:1
        (D) OTHER INFORMATION:/product= "OTHER"
            /note= "N-(L-GLU)-D-LYSINE"

(ix) FEATURE:
        (A) NAME/KEY: Peptide
        (B) LOCATION:2
        (D) OTHER INFORMATION:/product= "OTHER"
            /note= "D CONFIGURATION"

(xi) SEQUENCE DESCRIPTION: SEQ ID NO: 48:

Xaa Leu Leu Asp Val
1               5

(2) INFORMATION FOR SEQ ID NO: 49:

(i) SEQUENCE CHARACTERISTICS:
        (A) LENGTH: 5 amino acids
        (B) TYPE: amino acid
        (C) STRANDEDNESS: single
        (D) TOPOLOGY: circular (ii) MOLECULE TYPE: peptide (ix) FEATURE:
```

```
            (A) NAME/KEY: Peptide
            (B) LOCATION:1
            (D) OTHER INFORMATION:/product= "OTHER"
                /note= "N(PYROGLUTAMIC ACID)-D-LYSINE"

(ix) FEATURE:
            (A) NAME/KEY: Peptide
            (B) LOCATION:2
            (D) OTHER INFORMATION:/product= "OTHER"
                /note= "D CONFIGURATION"

(xi) SEQUENCE DESCRIPTION: SEQ ID NO: 49:

Xaa Leu Leu Asp Val
1               5

(2) INFORMATION FOR SEQ ID NO: 50:

(i) SEQUENCE CHARACTERISTICS:
            (A) LENGTH: 7 amino acids
            (B) TYPE: amino acid
            (C) STRANDEDNESS: single
            (D) TOPOLOGY: circular (ii) MOLECULE TYPE: peptide (ix) FEATURE:
            (A) NAME/KEY: Peptide
            (B) LOCATION:7
            (D) OTHER INFORMATION:/product= "OTHER"
                /note= "3-AMINO-PROPIONIC ACID"

(xi) SEQUENCE DESCRIPTION: SEQ ID NO: 50:

Glu Ile Leu Asp Val Pro Xaa
1               5

(2) INFORMATION FOR SEQ ID NO: 51:

(i) SEQUENCE CHARACTERISTICS:
            (A) LENGTH: 7 amino acids
            (B) TYPE: amino acid
            (C) STRANDEDNESS: single
            (D) TOPOLOGY: circular (ii) MOLECULE TYPE: peptide (ix) FEATURE:
            (A) NAME/KEY: Peptide
            (B) LOCATION:7
            (D) OTHER INFORMATION:/product= "OTHER"
                /note= "5-AMINO-PENTANOIC ACID"

(xi) SEQUENCE DESCRIPTION: SEQ ID NO: 51:

Glu Ile Leu Asp Val Pro Xaa
1               5

(2) INFORMATION FOR SEQ ID NO: 52:

(i) SEQUENCE CHARACTERISTICS:
            (A) LENGTH: 7 amino acids
            (B) TYPE: amino acid
            (C) STRANDEDNESS: single
            (D) TOPOLOGY: circular (ii) MOLECULE TYPE: peptide (ix) FEATURE:
            (A) NAME/KEY: Peptide
            (B) LOCATION:7
            (D) OTHER INFORMATION:/product= "OTHER"
                /note= "6-AMINO-HEXANOIC ACID"

(xi) SEQUENCE DESCRIPTION: SEQ ID NO: 52:
```

```
Glu Ile Leu Asp Val Pro Xaa
1               5

(2) INFORMATION FOR SEQ ID NO: 53:

(i) SEQUENCE CHARACTERISTICS:
        (A) LENGTH: 7 amino acids
        (B) TYPE: amino acid
        (C) STRANDEDNESS: single
        (D) TOPOLOGY: circular (ii) MOLECULE TYPE: peptide (ix) FEATURE:
        (A) NAME/KEY: Peptide
        (B) LOCATION:7
        (D) OTHER INFORMATION:/product= "OTHER"
            /note= "8-AMINO-OCTANOIC ACID"

(xi) SEQUENCE DESCRIPTION: SEQ ID NO: 53:

Glu Ile Leu Asp Val Pro Xaa
1               5

(2) INFORMATION FOR SEQ ID NO: 54:

(i) SEQUENCE CHARACTERISTICS:
        (A) LENGTH: 5 amino acids
        (B) TYPE: amino acid
        (C) STRANDEDNESS: single
        (D) TOPOLOGY: circular (ii) MOLECULE TYPE: peptide (ix) FEATURE:
        (A) NAME/KEY: Peptide
        (B) LOCATION:1
        (D) OTHER INFORMATION:/product= "OTHER"
            /note= "D CONFIGURATION"

(ix) FEATURE:
        (A) NAME/KEY: Peptide
        (B) LOCATION:5
        (D) OTHER INFORMATION:/product= "OTHER"
            /note= "-NH.CH2.CH2.S.CH2.CO-"

(xi) SEQUENCE DESCRIPTION: SEQ ID NO: 54:

Leu Leu Asp Val Xaa
1               5

(2) INFORMATION FOR SEQ ID NO: 55:

(i) SEQUENCE CHARACTERISTICS:
        (A) LENGTH: 5 amino acids
        (B) TYPE: amino acid
        (C) STRANDEDNESS: single
        (D) TOPOLOGY: circular (ii) MOLECULE TYPE: peptide (ix) FEATURE:
        (A) NAME/KEY: Peptide
        (B) LOCATION:5
        (D) OTHER INFORMATION:/product= "Methyl substituted Ile at position 1"
            /note= "5-AMINO-PENTANOIC ACID"

(xi) SEQUENCE DESCRIPTION: SEQ ID NO: 55:

Ile Leu Asp Val Xaa
1               5

(2) INFORMATION FOR SEQ ID NO: 56:

(i) SEQUENCE CHARACTERISTICS:
```

```
        (A) LENGTH: 5 amino acids
        (B) TYPE: amino acid
        (C) STRANDEDNESS: single
        (D) TOPOLOGY: circular (ii) MOLECULE TYPE: peptide (ix) FEATURE:
        (A) NAME/KEY: Peptide
        (B) LOCATION:1
        (D) OTHER INFORMATION:/product= "OTHER"
            /note= "TERT-LEUCINE, D CONFIGURATION"

(ix) FEATURE:
        (A) NAME/KEY: Peptide
        (B) LOCATION:5
        (D) OTHER INFORMATION:/product= "OTHER"
            /note= "5-AMINO-PENTOIC ACID"

(xi) SEQUENCE DESCRIPTION: SEQ ID NO: 56:

Xaa Leu Asp Val Xaa
1               5

(2) INFORMATION FOR SEQ ID NO: 57:

(i) SEQUENCE CHARACTERISTICS:
        (A) LENGTH: 5 amino acids
        (B) TYPE: amino acid
        (C) STRANDEDNESS: single
        (D) TOPOLOGY: circular (ii) MOLECULE TYPE: peptide (ix) FEATURE:
        (A) NAME/KEY: Peptide
        (B) LOCATION:1
        (D) OTHER INFORMATION:/product= "OTHER"
            /note= "D CONFIGURATION"

(ix) FEATURE:
        (A) NAME/KEY: Peptide
        (B) LOCATION:5
        (D) OTHER INFORMATION:/product= "OTHER"
            /note= "-NH.CH2.CH2.SO.CH2.CO-"

(xi) SEQUENCE DESCRIPTION: SEQ ID NO: 57:

Leu Leu Asp Val Xaa
1               5

(2) INFORMATION FOR SEQ ID NO: 58:

(i) SEQUENCE CHARACTERISTICS:
        (A) LENGTH: 5 amino acids
        (B) TYPE: amino acid
        (C) STRANDEDNESS: single
        (D) TOPOLOGY: circular (ii) MOLECULE TYPE: peptide (ix) FEATURE:
        (A) NAME/KEY: Peptide
        (B) LOCATION:5
        (D) OTHER INFORMATION:/product= "OTHER"
            /note= "-NH.CH2.CH2.S.CH2.CH2.CO-"

(xi) SEQUENCE DESCRIPTION: SEQ ID NO: 58:

Ile Leu Asp Val Xaa
1               5

(2) INFORMATION FOR SEQ ID NO: 59:

(i) SEQUENCE CHARACTERISTICS:
        (A) LENGTH: 6 amino acids
```

(B) TYPE: amino acid
            (C) STRANDEDNESS: single
            (D) TOPOLOGY: circular (ii) MOLECULE TYPE: peptide (ix) FEATURE:
            (A) NAME/KEY: Peptide
            (B) LOCATION:1
            (D) OTHER INFORMATION:/product= "OTHER"
                /note= "D CONFIGURATION"

(xi) SEQUENCE DESCRIPTION: SEQ ID NO: 59:

Leu Leu Asp Val Gly Gly
1               5

(2) INFORMATION FOR SEQ ID NO: 60:

(i) SEQUENCE CHARACTERISTICS:
            (A) LENGTH: 6 amino acids
            (B) TYPE: amino acid
            (C) STRANDEDNESS: single
            (D) TOPOLOGY: circular (ii) MOLECULE TYPE: peptide (ix) FEATURE:
            (A) NAME/KEY: Peptide
            (B) LOCATION:5
            (D) OTHER INFORMATION:/product= "bAla"

(ix) FEATURE:
            (A) NAME/KEY: Peptide
            (B) LOCATION:6
            (D) OTHER INFORMATION:/product= "bAla"

(xi) SEQUENCE DESCRIPTION: SEQ ID NO: 60:

Leu Leu Asp Val Ala Ala
1               5

(2) INFORMATION FOR SEQ ID NO: 61:

(i) SEQUENCE CHARACTERISTICS:
            (A) LENGTH: 6 amino acids
            (B) TYPE: amino acid
            (C) STRANDEDNESS: single
            (D) TOPOLOGY: circular (ii) MOLECULE TYPE: peptide (ix) FEATURE:
            (A) NAME/KEY: Peptide
            (B) LOCATION:1
            (D) OTHER INFORMATION:/product= "OTHER"
                /note= "D CONFIGURATION"

(ix) FEATURE:
            (A) NAME/KEY: Peptide
            (B) LOCATION:5
            (D) OTHER INFORMATION:/product= "bAla"

(xi) SEQUENCE DESCRIPTION: SEQ ID NO: 61:

Leu Leu Asp Val Ala Gly
1               5

(2) INFORMATION FOR SEQ ID NO: 62:

(i) SEQUENCE CHARACTERISTICS:
            (A) LENGTH: 6 amino acids
            (B) TYPE: amino acid
            (C) STRANDEDNESS: single
            (D) TOPOLOGY: circular (ii) MOLECULE TYPE: peptide (ix) FEATURE:
            (A) NAME/KEY: Peptide
            (B) LOCATION:1
            (D) OTHER INFORMATION:/product= "OTHER"
                /note= "D CONFIGURATION"

(ix) FEATURE:
            (A) NAME/KEY: Peptide
            (B) LOCATION:5
            (D) OTHER INFORMATION:/product= "bAla"

(ix) FEATURE:
            (A) NAME/KEY: Peptide
            (B) LOCATION:6
            (D) OTHER INFORMATION:/product= "OTHER"
                /note= "N-METHYL-ALANINE"

(xi) SEQUENCE DESCRIPTION: SEQ ID NO: 62:

Leu Leu Asp Val Ala Xaa
1               5

(2) INFORMATION FOR SEQ ID NO: 63:

(i) SEQUENCE CHARACTERISTICS:
            (A) LENGTH: 6 amino acids
            (B) TYPE: amino acid
            (C) STRANDEDNESS: single
            (D) TOPOLOGY: circular (ii) MOLECULE TYPE: peptide (ix) FEATURE:
            (A) NAME/KEY: Peptide
            (B) LOCATION:1
            (D) OTHER INFORMATION:/product= "OTHER"
                /note= "D CONFIGURATION"

(ix) FEATURE:
            (A) NAME/KEY: Peptide
            (B) LOCATION:5
            (D) OTHER INFORMATION:/product= "bAla"

(xi) SEQUENCE DESCRIPTION: SEQ ID NO: 63:

Leu Leu Asp Val Ala Pro
1               5

(2) INFORMATION FOR SEQ ID NO: 64:

(i) SEQUENCE CHARACTERISTICS:
            (A) LENGTH: 6 amino acids
            (B) TYPE: amino acid
            (C) STRANDEDNESS: single
            (D) TOPOLOGY: circular (ii) MOLECULE TYPE: peptide (ix) FEATURE:
            (A) NAME/KEY: Peptide
            (B) LOCATION:1
            (D) OTHER INFORMATION:/product= "OTHER"
                /note= "D CONFIGURATION"

(ix) FEATURE:
            (A) NAME/KEY: Peptide
            (B) LOCATION:5
            (D) OTHER INFORMATION:/product= "OTHER"
                /note= "D CONFIGURATION"

(ix) FEATURE:
            (A) NAME/KEY: Peptide
            (B) LOCATION:6
            (D) OTHER INFORMATION:/product= "OTHER"
                /note= "D CONFIGURATION"

(xi) SEQUENCE DESCRIPTION: SEQ ID NO: 64:

Leu Leu Asp Val Ala Ala
1               5

(2) INFORMATION FOR SEQ ID NO: 65:

(i) SEQUENCE CHARACTERISTICS:
            (A) LENGTH: 6 amino acids
            (B) TYPE: amino acid
            (C) STRANDEDNESS: single
            (D) TOPOLOGY: circular (ii) MOLECULE TYPE: peptide (ix) FEATURE:
            (A) NAME/KEY: Peptide
            (B) LOCATION:1
            (D) OTHER INFORMATION:/product= "OTHER"
                /note= "D CONFIGURATION"

(ix) FEATURE:
            (A) NAME/KEY: Peptide
            (B) LOCATION:5
            (D) OTHER INFORMATION:/product= "bAla"

(ix) FEATURE:
            (A) NAME/KEY: Peptide
            (B) LOCATION:6
            (D) OTHER INFORMATION:/product= "OTHER"
                /note= "4-AMINO-BUTYRIC ACID"

(xi) SEQUENCE DESCRIPTION: SEQ ID NO: 65:

Leu Leu Asp Val Ala Xaa
1               5

(2) INFORMATION FOR SEQ ID NO: 66:

(i) SEQUENCE CHARACTERISTICS:
            (A) LENGTH: 6 amino acids
            (B) TYPE: amino acid
            (C) STRANDEDNESS: single
            (D) TOPOLOGY: circular (ii) MOLECULE TYPE: peptide (ix) FEATURE:
            (A) NAME/KEY: Peptide
            (B) LOCATION:1
            (D) OTHER INFORMATION:/product= "OTHER"
                /note= "D CONFIGURATION"

(ix) FEATURE:
            (A) NAME/KEY: Peptide
            (B) LOCATION:5
            (D) OTHER INFORMATION:/product= "bAla"

(ix) FEATURE:
            (A) NAME/KEY: Peptide
            (B) LOCATION:6
            (D) OTHER INFORMATION:/product= "OTHER"
                /note= "D CONFIGURATION"

(xi) SEQUENCE DESCRIPTION: SEQ ID NO: 66:

Leu Leu Asp Val Ala Ala
1               5

(2) INFORMATION FOR SEQ ID NO: 67:

(i) SEQUENCE CHARACTERISTICS:
            (A) LENGTH: 6 amino acids
            (B) TYPE: amino acid
            (C) STRANDEDNESS: single (D) TOPOLOGY: circular (ii) MOLECULE TYPE: peptide (ix) FEATURE:
            (A) NAME/KEY: Peptide
            (B) LOCATION:1
            (D) OTHER INFORMATION:/product= "OTHER"
                /note= "D CONFIGURATION"

(xi) SEQUENCE DESCRIPTION: SEQ ID NO: 67:

Leu Leu Asp Val Pro Pro
1               5

(2) INFORMATION FOR SEQ ID NO: 68:

(i) SEQUENCE CHARACTERISTICS:
            (A) LENGTH: 6 amino acids
            (B) TYPE: amino acid
            (C) STRANDEDNESS: single
            (D) TOPOLOGY: circular (ii) MOLECULE TYPE: peptide (ix) FEATURE:
            (A) NAME/KEY: Peptide
            (B) LOCATION:1
            (D) OTHER INFORMATION:/product= "OTHER"
                /note= "D CONFIGURATION"

(ix) FEATURE:
            (A) NAME/KEY: Peptide
            (B) LOCATION:6
            (D) OTHER INFORMATION:/product= "OTHER"
                /note= "D CONFIGURATION"

(xi) SEQUENCE DESCRIPTION: SEQ ID NO: 68:

Leu Leu Asp Val Pro Pro
1               5

(2) INFORMATION FOR SEQ ID NO: 69:

(i) SEQUENCE CHARACTERISTICS:
            (A) LENGTH: 5 amino acids
            (B) TYPE: amino acid
            (C) STRANDEDNESS: single
            (D) TOPOLOGY: circular (ii) MOLECULE TYPE: peptide (ix) FEATURE:
            (A) NAME/KEY: Peptide
            (B) LOCATION:5
            (D) OTHER INFORMATION:/product= "OTHER"
                /note= "5-AMINO-PENTANOIC ACID"

(xi) SEQUENCE DESCRIPTION: SEQ ID NO: 69:

Ile Leu Asp Leu Xaa
1               5

(2) INFORMATION FOR SEQ ID NO: 70:

(i) SEQUENCE CHARACTERISTICS:
            (A) LENGTH: 5 amino acids
            (B) TYPE: amino acid
            (C) STRANDEDNESS: single
            (D) TOPOLOGY: circular (ii) MOLECULE TYPE: peptide (ix) FEATURE:
            (A) NAME/KEY: Peptide
            (B) LOCATION:5

```
            (D) OTHER INFORMATION:/product= "OTHER"
                /note= "-NH.CH(CONH2).CH2.CH2.CO-"

(xi) SEQUENCE DESCRIPTION: SEQ ID NO: 70:

Ile Leu Asp Val Xaa
1               5

(2) INFORMATION FOR SEQ ID NO: 71:

(i) SEQUENCE CHARACTERISTICS:
        (A) LENGTH: 5 amino acids
        (B) TYPE: amino acid
        (C) STRANDEDNESS: single
        (D) TOPOLOGY: circular (ii) MOLECULE TYPE: peptide (ix) FEATURE:
        (A) NAME/KEY: Peptide
        (B) LOCATION:5
        (D) OTHER INFORMATION:/product= "OTHER"
                /note= "5-AMINO-PENTANOIC ACID"

(xi) SEQUENCE DESCRIPTION: SEQ ID NO: 71:

Ile Leu Asp Phe Xaa
1               5

(2) INFORMATION FOR SEQ ID NO: 72:

(i) SEQUENCE CHARACTERISTICS:
        (A) LENGTH: 6 amino acids
        (B) TYPE: amino acid
        (C) STRANDEDNESS: single
        (D) TOPOLOGY: circular (ii) MOLECULE TYPE: peptide (ix) FEATURE:
        (A) NAME/KEY: Peptide
        (B) LOCATION:5
        (D) OTHER INFORMATION:/product= "OTHER"
                /note= "5-AMINO-PENTANOIC ACID"

(ix) FEATURE:
        (A) NAME/KEY: Peptide
        (B) LOCATION:6
        (D) OTHER INFORMATION:/product= "bAla"

(xi) SEQUENCE DESCRIPTION: SEQ ID NO: 72:

Ile Leu Asp Val Xaa Ala
1               5

(2) INFORMATION FOR SEQ ID NO: 73:

(i) SEQUENCE CHARACTERISTICS:
        (A) LENGTH: 6 amino acids
        (B) TYPE: amino acid
        (C) STRANDEDNESS: single
        (D) TOPOLOGY: circular (ii) MOLECULE TYPE: peptide (ix) FEATURE:
        (A) NAME/KEY: Peptide
        (B) LOCATION:1
        (D) OTHER INFORMATION:/product= "MeIle"

(ix) FEATURE:
        (A) NAME/KEY: Peptide
        (B) LOCATION:5
        (D) OTHER INFORMATION:/product= "bAla"

(xi) SEQUENCE DESCRIPTION: SEQ ID NO: 73:
```

```
Ile Leu Asp Val Ala Pro
1               5

(2) INFORMATION FOR SEQ ID NO: 74:

(i) SEQUENCE CHARACTERISTICS:
        (A) LENGTH: 6 amino acids
        (B) TYPE: amino acid
        (C) STRANDEDNESS: single
        (D) TOPOLOGY: circular (ii) MOLECULE TYPE: peptide (ix) FEATURE:
        (A) NAME/KEY: Peptide
        (B) LOCATION:1
        (D) OTHER INFORMATION:/product= "MeIle"

(ix) FEATURE:
        (A) NAME/KEY: Peptide
        (B) LOCATION:5
        (D) OTHER INFORMATION:/product= "bAla"

(ix) FEATURE:
        (A) NAME/KEY: Peptide
        (B) LOCATION:6
        (D) OTHER INFORMATION:/product= "OTHER"
            /note= "D CONFIGURATION"

(xi) SEQUENCE DESCRIPTION: SEQ ID NO: 74:

Ile Leu Asp Val Ala Ala
1               5

(2) INFORMATION FOR SEQ ID NO: 75:

(i) SEQUENCE CHARACTERISTICS:
        (A) LENGTH: 6 amino acids
        (B) TYPE: amino acid
        (C) STRANDEDNESS: single
        (D) TOPOLOGY: circular (ii) MOLECULE TYPE: peptide (ix) FEATURE:
        (A) NAME/KEY: Peptide
        (B) LOCATION:1
        (D) OTHER INFORMATION:/product= "MeIle"

(ix) FEATURE:
        (A) NAME/KEY: Peptide
        (B) LOCATION:5
        (D) OTHER INFORMATION:/product= "OTHER"
            /note= "D-CONFIGURATION"

(ix) FEATURE:
        (A) NAME/KEY: Peptide
        (B) LOCATION:6
        (D) OTHER INFORMATION:/product= "OTHER"
            /note= "D CONFIGURATION"

(xi) SEQUENCE DESCRIPTION: SEQ ID NO: 75:

Ile Leu Asp Val Ala Ala
1               5

(2) INFORMATION FOR SEQ ID NO: 76:

(i) SEQUENCE CHARACTERISTICS:
        (A) LENGTH: 6 amino acids
        (B) TYPE: amino acid
        (C) STRANDEDNESS: single
        (D) TOPOLOGY: circular (ii) MOLECULE TYPE: peptide
```

(ix) FEATURE:
              (A) NAME/KEY: Peptide
              (B) LOCATION:1
              (D) OTHER INFORMATION:/product= "MeIle"

(ix) FEATURE:
              (A) NAME/KEY: Peptide
              (B) LOCATION:5
              (D) OTHER INFORMATION:/product= "bAla"

(ix) FEATURE:
              (A) NAME/KEY: Peptide
              (B) LOCATION:6
              (D) OTHER INFORMATION:/product= "Orn"
                  /note= "D CONFIGURATION"

(xi) SEQUENCE DESCRIPTION: SEQ ID NO: 76:

Ile Leu Asp Val Ala Xaa
1               5

(2) INFORMATION FOR SEQ ID NO: 77:

(i) SEQUENCE CHARACTERISTICS:
              (A) LENGTH: 6 amino acids
              (B) TYPE: amino acid
              (C) STRANDEDNESS: single
              (D) TOPOLOGY: circular (ii) MOLECULE TYPE: peptide (ix) FEATURE:
              (A) NAME/KEY: Peptide
              (B) LOCATION:1
              (D) OTHER INFORMATION:/product= "MeIle"

(ix) FEATURE:
              (A) NAME/KEY: Peptide
              (B) LOCATION:5
              (D) OTHER INFORMATION:/product= "bAla"

(ix) FEATURE:
              (A) NAME/KEY: Peptide
              (B) LOCATION:6
              (D) OTHER INFORMATION:/product= "OTHER"
                  /note= "D CONFIGURATION"

(xi) SEQUENCE DESCRIPTION: SEQ ID NO: 77:

Ile Leu Asp Val Ala Lys
1               5

(2) INFORMATION FOR SEQ ID NO: 78:

(i) SEQUENCE CHARACTERISTICS:
              (A) LENGTH: 6 amino acids
              (B) TYPE: amino acid
              (C) STRANDEDNESS: single
              (D) TOPOLOGY: circular (ii) MOLECULE TYPE: peptide (ix) FEATURE:
              (A) NAME/KEY: Peptide
              (B) LOCATION:5
              (D) OTHER INFORMATION:/product= "OTHER"
                  /note= "PIPERAZINYL-1YL-ACETIC ACID"

(ix) FEATURE:
              (A) NAME/KEY: Peptide
              (B) LOCATION:6
              (D) OTHER INFORMATION:/product= "OTHER"
                  /note= "-NH.CH2.CH2.CH2.CO-"

(xi) SEQUENCE DESCRIPTION: SEQ ID NO: 78:

```
Ile Leu Asp Val Xaa Xaa
1               5

(2) INFORMATION FOR SEQ ID NO: 79:

(i) SEQUENCE CHARACTERISTICS:
        (A) LENGTH: 6 amino acids
        (B) TYPE: amino acid
        (C) STRANDEDNESS: single
        (D) TOPOLOGY: circular (ii) MOLECULE TYPE: peptide (ix) FEATURE:
        (A) NAME/KEY: Peptide
        (B) LOCATION:5
        (D) OTHER INFORMATION:/product= "OTHER"
            /note= "PIPERAZINYL-1-YL-ACETIC ACID"

(ix) FEATURE:
        (A) NAME/KEY: Peptide
        (B) LOCATION:6
        (D) OTHER INFORMATION:/product= "OTHER"
            /note= "-NH.CH2.CH2.CH2.CH2.CO-"

(xi) SEQUENCE DESCRIPTION: SEQ ID NO: 79:

Ile Leu Asp Val Xaa Xaa
1               5

(2) INFORMATION FOR SEQ ID NO: 80:

(i) SEQUENCE CHARACTERISTICS:
        (A) LENGTH: 6 amino acids
        (B) TYPE: amino acid
        (C) STRANDEDNESS: single
        (D) TOPOLOGY: circular (ii) MOLECULE TYPE: peptide (ix) FEATURE:
        (A) NAME/KEY: Peptide
        (B) LOCATION:5
        (D) OTHER INFORMATION:/product= "OTHER"
            /note= "PIPERAZINYL-1YL-PROPIONIC ACID"

(ix) FEATURE:
        (A) NAME/KEY: Peptide
        (B) LOCATION:6
        (D) OTHER INFORMATION:/product= "OTHER"
            /note= "N-ACETYL-LYSINE"

(xi) SEQUENCE DESCRIPTION: SEQ ID NO: 80:

Ile Leu Asp Val Xaa Xaa
1               5

(2) INFORMATION FOR SEQ ID NO: 81:

(i) SEQUENCE CHARACTERISTICS:
        (A) LENGTH: 6 amino acids
        (B) TYPE: amino acid
        (C) STRANDEDNESS: single
        (D) TOPOLOGY: circular (ii) MOLECULE TYPE: peptide (ix) FEATURE:
        (A) NAME/KEY: Peptide
        (B) LOCATION:5
        (D) OTHER INFORMATION:/product= "OTHER"
            /note= "(4-(2-AMINOETHYL)-IMIDAZOL-1-YL)-
            ACETIC ACID"

(ix) FEATURE:
        (A) NAME/KEY: Peptide
```

(B) LOCATION:6
            (D) OTHER INFORMATION:/product= "bAla"

(xi) SEQUENCE DESCRIPTION: SEQ ID NO: 81:

Ile Leu Asp Val Xaa Ala
1               5

(2) INFORMATION FOR SEQ ID NO: 82:

(i) SEQUENCE CHARACTERISTICS:
        (A) LENGTH: 5 amino acids
        (B) TYPE: amino acid
        (C) STRANDEDNESS: single
        (D) TOPOLOGY: circular (ii) MOLECULE TYPE: peptide (ix) FEATURE:
        (A) NAME/KEY: Peptide
        (B) LOCATION:1
        (D) OTHER INFORMATION:/product= "OTHER"
            /note= "N(PIPERAZIN-1-YL-ACETYL)- LYSINE, D
            CONFIGURATION"

(ix) FEATURE:
        (A) NAME/KEY: Peptide
        (B) LOCATION:2
        (D) OTHER INFORMATION:/product= "OTHER"
            /note= "D CONFIGURATION"

(xi) SEQUENCE DESCRIPTION: SEQ ID NO: 82:

Xaa Leu Leu Asp Val
1               5

(2) INFORMATION FOR SEQ ID NO: 83:

(i) SEQUENCE CHARACTERISTICS:
        (A) LENGTH: 5 amino acids
        (B) TYPE: amino acid
        (C) STRANDEDNESS: single
        (D) TOPOLOGY: circular (ii) MOLECULE TYPE: peptide (ix) FEATURE:
        (A) NAME/KEY: Peptide
        (B) LOCATION:1
        (D) OTHER INFORMATION:/product= "OTHER"
            /note= "N(NH2.CH2.CH2.CH2.CO)-LYSINE, D
            CONFIGURATION"

(ix) FEATURE:
        (A) NAME/KEY: Peptide
        (B) LOCATION:2
        (D) OTHER INFORMATION:/product= "OTHER"
            /note= "D CONFIGURATION"

(xi) SEQUENCE DESCRIPTION: SEQ ID NO: 83:

Xaa Leu Leu Asp Val
1               5

(2) INFORMATION FOR SEQ ID NO: 84:

(i) SEQUENCE CHARACTERISTICS:
        (A) LENGTH: 5 amino acids
        (B) TYPE: amino acid
        (C) STRANDEDNESS: single
        (D) TOPOLOGY: circular (ii) MOLECULE TYPE: peptide (ix) FEATURE:
        (A) NAME/KEY: Peptide

```
          (B) LOCATION:1
          (D) OTHER INFORMATION:/product= "OTHER"
              /note= "N(ARG)-D-LYS"

(ix) FEATURE:
          (A) NAME/KEY: Peptide
          (B) LOCATION:2
          (D) OTHER INFORMATION:/product= "OTHER"
              /note= "D CONFIGURATION"

(xi) SEQUENCE DESCRIPTION: SEQ ID NO: 84:

Xaa Leu Leu Asp Val
1               5

(2) INFORMATION FOR SEQ ID NO: 85:

(i) SEQUENCE CHARACTERISTICS:
          (A) LENGTH: 6 amino acids
          (B) TYPE: amino acid
          (C) STRANDEDNESS: single
          (D) TOPOLOGY: circular (ii) MOLECULE TYPE: peptide (ix) FEATURE:
          (A) NAME/KEY: Peptide
          (B) LOCATION:5
          (D) OTHER INFORMATION:/product= "OTHER"
              /note= "D CONFIGURATION"

(ix) FEATURE:
          (A) NAME/KEY: Peptide
          (B) LOCATION:6
          (D) OTHER INFORMATION:/product= "OTHER"
              /note= "PIPERAZINYL-1YL-ACETIC ACID"

(xi) SEQUENCE DESCRIPTION: SEQ ID NO: 85:

Ile Leu Asp Val Lys Xaa
1               5

(2) INFORMATION FOR SEQ ID NO: 86:

(i) SEQUENCE CHARACTERISTICS:
          (A) LENGTH: 5 amino acids
          (B) TYPE: amino acid
          (C) STRANDEDNESS: single
          (D) TOPOLOGY: linear (ii) MOLECULE TYPE: peptide (ix) FEATURE:
          (A) NAME/KEY: Peptide
          (B) LOCATION:3
          (D) OTHER INFORMATION:/product= "OTHER"
              /note= "O-(TERT-BUTYL)-ASP"

(ix) FEATURE:
          (A) NAME/KEY: Peptide
          (B) LOCATION:5
          (D) OTHER INFORMATION:/product= "4Abu"

(ix) FEATURE:
          (A) NAME/KEY: Peptide
          (B) LOCATION:5
          (D) OTHER INFORMATION:/product= "OTHER"
              /note= "-NH.CH2.CH2.CH2.COOH"

(xi) SEQUENCE DESCRIPTION: SEQ ID NO: 86:

Ile Leu Xaa Val Xaa
1               5

(2) INFORMATION FOR SEQ ID NO: 87:
```

```
    (i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:3
        (D) OTHER INFORMATION:/product= "OTHER"
            /note= "O-(TERT-BUTYL)-ASP"

(ix) FEATURE:
        (A) NAME/KEY: Peptide
        (B) LOCATION:5
        (D) OTHER INFORMATION:/product= "OTHER"
            /note= "-NH.CH2.CH2.CH2.CH2.COOH"

(xi) SEQUENCE DESCRIPTION: SEQ ID NO: 87:

Ile Leu Xaa Val Xaa
1               5

(2) INFORMATION FOR SEQ ID NO: 88:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:5
        (D) OTHER INFORMATION:/product= "OTHER"
            /note= "-NH.CH2.CH2.CH2.CH2.CH2.COOH"

(ix) FEATURE:
        (A) NAME/KEY: Peptide
        (B) LOCATION:3
        (D) OTHER INFORMATION:/product= "OTHER"
            /note= "O-(TERT-BUTYL)-ASP"

(xi) SEQUENCE DESCRIPTION: SEQ ID NO: 88:

Ile Leu Xaa Val Xaa
1               5

(2) INFORMATION FOR SEQ ID NO: 89:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:3
        (D) OTHER INFORMATION:/product= "OTHER"
            /note= "O-(TERT-BUTYL)-ASP"

(ix) FEATURE:
        (A) NAME/KEY: Peptide
        (B) LOCATION:5
        (D) OTHER INFORMATION:/product= "OTHER"
            /note= "-NH.CH2.CH2.CH2.CH2.CH2.CH2.COOH"

(xi) SEQUENCE DESCRIPTION: SEQ ID NO: 89:

Ile Leu Xaa Val Xaa
```

```
1               5

(2) INFORMATION FOR SEQ ID NO: 90:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:3
        (D) OTHER INFORMATION:/product= "OTHER"
            /note= "O-(TERT-BUTYL)-ASP"

(ix) FEATURE:
        (A) NAME/KEY: Peptide
        (B) LOCATION:5
        (D) OTHER INFORMATION:/product= "OTHER"
            /note= "-NH.CH2.CH2.CH2.CH2.CH2.COOH"

(xi) SEQUENCE DESCRIPTION: SEQ ID NO: 90:

Pro Leu Xaa Val Xaa
1               5

(2) INFORMATION FOR SEQ ID NO: 91:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:3
        (D) OTHER INFORMATION:/product= "OTHER"
            /note= "O-(TERT-BUTYL)-ASP"

(ix) FEATURE:
        (A) NAME/KEY: Peptide
        (B) LOCATION:5
        (D) OTHER INFORMATION:/product= "OTHER"
            /note= "-NH.CH2.CH2.CH2.CH2.CH2.COOH"

(xi) SEQUENCE DESCRIPTION: SEQ ID NO: 91:

Gly Leu Xaa Val Xaa
1               5

(2) INFORMATION FOR SEQ ID NO: 92:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:1
        (D) OTHER INFORMATION:/product= "OTHER"
            /note= "TERT-LEU"

(ix) FEATURE:
        (A) NAME/KEY: Peptide
        (B) LOCATION:3
        (D) OTHER INFORMATION:/product= "OTHER"
```

/note= "O-(TERT-BUTYL)-ASP"

(ix) FEATURE:
            (A) NAME/KEY: Peptide
            (B) LOCATION:5
            (D) OTHER INFORMATION:/product= "OTHER"
                    /note= "-NH.CH2.CH2.CH2.CH2.CH2.COOH"

(xi) SEQUENCE DESCRIPTION: SEQ ID NO: 92:

Xaa Leu Xaa Val Xaa
1               5

(2) INFORMATION FOR SEQ ID NO: 93:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION:1
            (D) OTHER INFORMATION:/product= "OTHER"
                    /note= "TERT-BUTYL-ALANINE"

(ix) FEATURE:
            (A) NAME/KEY: Peptide
            (B) LOCATION:3
            (D) OTHER INFORMATION:/product= "OTHER"
                    /note= "O-(TERT-BUTYL)-ASP"

(ix) FEATURE:
            (A) NAME/KEY: Peptide
            (B) LOCATION:5
            (D) OTHER INFORMATION:/product= "OTHER"
                    /note= "-NH.CH2.CH2.CH2.CH2.CH2.COOH"

(xi) SEQUENCE DESCRIPTION: SEQ ID NO: 93:

Xaa Leu Xaa Val Xaa
1               5

(2) INFORMATION FOR SEQ ID NO: 94:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION:1
            (D) OTHER INFORMATION:/product= "OTHER"
                    /note= "Z-ORN"

(ix) FEATURE:
            (A) NAME/KEY: Peptide
            (B) LOCATION:4
            (D) OTHER INFORMATION:/product= "OTHER"
                    /note= "O(TERT-BUTYL)-ASP"

(xi) SEQUENCE DESCRIPTION: SEQ ID NO: 94:

Xaa Ile Leu Xaa Val
1               5

(2) INFORMATION FOR SEQ ID NO: 95:

(i) SEQUENCE CHARACTERISTICS:

```
            (A) LENGTH: 5 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION:3
            (D) OTHER INFORMATION:/product= "OTHER"
                /note= "O-(TERT-BUTYL)-ASP"

(ix) FEATURE:
            (A) NAME/KEY: Peptide
            (B) LOCATION:5
            (D) OTHER INFORMATION:/product= "OTHER"
                /note= "4-AMINOMETHYL-BENZOIC ACID"

(xi) SEQUENCE DESCRIPTION: SEQ ID NO: 95:

Ile Leu Xaa Val Xaa
1               5

(2) INFORMATION FOR SEQ ID NO: 96:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION:3
            (D) OTHER INFORMATION:/product= "OTHER"
                /note= "O-(TERT-BUTYL)-ASP"

(ix) FEATURE:
            (A) NAME/KEY: Peptide
            (B) LOCATION:5
            (D) OTHER INFORMATION:/product= "OTHER"
                /note= "(4-(2-AMINOETHYL)-IMIDAZOL-1-YL)-
                ACETIC ACID"

(xi) SEQUENCE DESCRIPTION: SEQ ID NO: 96:

Ile Leu Xaa Val Xaa
1               5

(2) INFORMATION FOR SEQ ID NO: 97:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION:1
            (D) OTHER INFORMATION:/product= "bAla"

(ix) FEATURE:
            (A) NAME/KEY: Peptide
            (B) LOCATION:4
            (D) OTHER INFORMATION:/product= "OTHER"
                /note= "O-(TERT-BUTYL)-ASP"

(ix) FEATURE:
            (A) NAME/KEY: Peptide
            (B) LOCATION:6
            (D) OTHER INFORMATION:/product= "OTHER"
```

/note= "PIPERAZINYL-1YL-ACETIC ACID"

(xi) SEQUENCE DESCRIPTION: SEQ ID NO: 97:

Ala Ile Leu Xaa Val Xaa
1               5

(2) INFORMATION FOR SEQ ID NO: 98:

(i) SEQUENCE CHARACTERISTICS:
      (A) LENGTH: 5 amino acids
      (B) TYPE: amino acid
      (C) STRANDEDNESS: single
      (D) TOPOLOGY: linear (ii) MOLECULE TYPE: peptide (ix) FEATURE:
      (A) NAME/KEY: Peptide
      (B) LOCATION:1
      (D) OTHER INFORMATION:/product= "OTHER"
         /note= "Z-LYS"

(ix) FEATURE:
      (A) NAME/KEY: Peptide
      (B) LOCATION:4
      (D) OTHER INFORMATION:/product= "OTHER"
         /note= "O-(TERT-BUTYL)-ASP"

(xi) SEQUENCE DESCRIPTION: SEQ ID NO: 98:

Xaa Ile Leu Xaa Val
1               5

(2) INFORMATION FOR SEQ ID NO: 99:

(i) SEQUENCE CHARACTERISTICS:
      (A) LENGTH: 5 amino acids
      (B) TYPE: amino acid
      (C) STRANDEDNESS: single
      (D) TOPOLOGY: linear (ii) MOLECULE TYPE: peptide (ix) FEATURE:
      (A) NAME/KEY: Peptide
      (B) LOCATION:1
      (D) OTHER INFORMATION:/product= "OTHER"
         /note= "Z-(2,4-DIAMINO-BUTYRIC ACID)"

(ix) FEATURE:
      (A) NAME/KEY: Peptide
      (B) LOCATION:4
      (D) OTHER INFORMATION:/product= "OTHER"
         /note= "O-(TERT-BUTYL)-ASP"

(xi) SEQUENCE DESCRIPTION: SEQ ID NO: 99:

Xaa Ile Leu Xaa Val
1               5

(2) INFORMATION FOR SEQ ID NO: 100:

(i) SEQUENCE CHARACTERISTICS:
      (A) LENGTH: 5 amino acids
      (B) TYPE: amino acid
      (C) STRANDEDNESS: single
      (D) TOPOLOGY: linear (ii) MOLECULE TYPE: peptide (ix) FEATURE:
      (A) NAME/KEY: Peptide
      (B) LOCATION:1
      (D) OTHER INFORMATION:/product= "OTHER"
         /note= "N-METHYL-ALANINE"

```
        (ix) FEATURE:
              (A) NAME/KEY: Peptide
              (B) LOCATION:3
              (D) OTHER INFORMATION:/product= "OTHER"
                   /note= "O-(TERT-BUTYL)-ASP"

(ix) FEATURE:
              (A) NAME/KEY: Peptide
              (B) LOCATION:5
              (D) OTHER INFORMATION:/product= "OTHER"
                   /note= "-NH.CH2.CH2.CH2.CH2.CH2.COOH"

(xi) SEQUENCE DESCRIPTION: SEQ ID NO: 100:

Xaa Leu Xaa Val Xaa
1               5

(2) INFORMATION FOR SEQ ID NO: 101:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (ix) FEATURE:
              (A) NAME/KEY: Peptide
              (B) LOCATION:1
              (D) OTHER INFORMATION:/product= "OTHER"
                   /note= "N-METHYL-LEUCINE"

(ix) FEATURE:
              (A) NAME/KEY: Peptide
              (B) LOCATION:3
              (D) OTHER INFORMATION:/product= "OTHER"
                   /note= "O-(TERT-BUTYL)-ASP"

(ix) FEATURE:
              (A) NAME/KEY: Peptide
              (B) LOCATION:5
              (D) OTHER INFORMATION:/product= "OTHER"
                   /note= "-NH.CH2.CH2.CH2.CH2.CH2.COOH"

(xi) SEQUENCE DESCRIPTION: SEQ ID NO: 101:

Xaa Leu Xaa Val Xaa
1               5

(2) INFORMATION FOR SEQ ID NO: 102:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (ix) FEATURE:
              (A) NAME/KEY: Peptide
              (B) LOCATION:2
              (D) OTHER INFORMATION:/product= "OTHER"
                   /note= "TERT-BUTYL-ALANINE"

(ix) FEATURE:
              (A) NAME/KEY: Peptide
              (B) LOCATION:3
              (D) OTHER INFORMATION:/product= "OTHER"
                   /note= "O-(TERT-BUTYL)-ASP"

(ix) FEATURE:
              (A) NAME/KEY: Peptide
              (B) LOCATION:5
              (D) OTHER INFORMATION:/product= "OTHER"
```

/note= "-NH.CH2.CH2.CH2.CH2.CH2.COOH"

(xi) SEQUENCE DESCRIPTION: SEQ ID NO: 102:

Ile Xaa Xaa Val Xaa
1               5

(2) INFORMATION FOR SEQ ID NO: 103:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:3
        (D) OTHER INFORMATION:/product= "OTHER"
            /note= "O-(TERT-BUTYL)-ASP"

(ix) FEATURE:
        (A) NAME/KEY: Peptide
        (B) LOCATION:5
        (D) OTHER INFORMATION:/product= "OTHER"
            /note= "-NH.CH2.CH2.CH2.CH2.COOH"

(xi) SEQUENCE DESCRIPTION: SEQ ID NO: 103:

Ile Ile Xaa Val Xaa
1               5

(2) INFORMATION FOR SEQ ID NO: 104:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:2
        (D) OTHER INFORMATION:/product= "Nle"

(ix) FEATURE:
        (A) NAME/KEY: Peptide
        (B) LOCATION:3
        (D) OTHER INFORMATION:/product= "OTHER"
            /note= "O-(TERT-BUTYL)-ASP"

(ix) FEATURE:
        (A) NAME/KEY: Peptide
        (B) LOCATION:5
        (D) OTHER INFORMATION:/product= "OTHER"
            /note= "-NH-CH2.CH2.CH2.CH2.COOH"

(xi) SEQUENCE DESCRIPTION: SEQ ID NO: 104:

Ile Leu Xaa Val Xaa
1               5

(2) INFORMATION FOR SEQ ID NO: 105:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide

```
    (ix) FEATURE:
         (A) NAME/KEY: Peptide
         (B) LOCATION:3
         (D) OTHER INFORMATION:/product= "OTHER"
             /note= "O-(TERT-BUTYL)-ASP"

(ix) FEATURE:
         (A) NAME/KEY: Peptide
         (B) LOCATION:5
         (D) OTHER INFORMATION:/product= "OTHER"
             /note= "-NH.CH2.CH2.CH2.CH2.COOH"

(xi) SEQUENCE DESCRIPTION: SEQ ID NO: 105:

Ile Val Xaa Val Xaa
1               5

(2) INFORMATION FOR SEQ ID NO: 106:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (ix) FEATURE:
         (A) NAME/KEY: Peptide
         (B) LOCATION:2
         (D) OTHER INFORMATION:/product= "OTHER"
             /note= "CYCLOHEXYL-ALANINE"

(ix) FEATURE:
         (A) NAME/KEY: Peptide
         (B) LOCATION:3
         (D) OTHER INFORMATION:/product= "OTHER"
             /note= "O-(TERT-BUTYL)-ASP"

(ix) FEATURE:
         (A) NAME/KEY: Peptide
         (B) LOCATION:5
         (D) OTHER INFORMATION:/product= "OTHER"
             /note= "-NH.CH2.CH2.CH2.CH2.COOH"

(xi) SEQUENCE DESCRIPTION: SEQ ID NO: 106:

Ile Xaa Xaa Val Xaa
1               5

(2) INFORMATION FOR SEQ ID NO: 107:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (ix) FEATURE:
         (A) NAME/KEY: Peptide
         (B) LOCATION:2
         (D) OTHER INFORMATION:/product= "OTHER"
             /note= "TERIARY-LEUCINE"

(ix) FEATURE:
         (A) NAME/KEY: Peptide
         (B) LOCATION:3
         (D) OTHER INFORMATION:/product= "OTHER"
             /note= "O-(TERT-BUTYL)-ASP"

(ix) FEATURE:
         (A) NAME/KEY: Peptide
         (B) LOCATION:5
         (D) OTHER INFORMATION:/product= "OTHER"
             /note= "-NH.CH2.CH2.CH2.CH2.COOH"
```

(xi) SEQUENCE DESCRIPTION: SEQ ID NO: 107:

Ile Xaa Xaa Val Xaa
1               5

(2) INFORMATION FOR SEQ ID NO: 108:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:1
        (D) OTHER INFORMATION:/product= "OTHER"
            /note= "O-(TERT-BUTYL)-GLU"

(ix) FEATURE:
        (A) NAME/KEY: Peptide
        (B) LOCATION:4
        (D) OTHER INFORMATION:/product= "OTHER"
            /note= "O-(TERT-BUTYL)-ASP"

(ix) FEATURE:
        (A) NAME/KEY: Peptide
        (B) LOCATION:7
        (D) OTHER INFORMATION:/product= "OTHER"
            /note= "-NH.CH2.CH2.COOH"

(xi) SEQUENCE DESCRIPTION: SEQ ID NO: 108:

Xaa Ile Leu Xaa Val Pro Xaa
1               5

(2) INFORMATION FOR SEQ ID NO: 109:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:1
        (D) OTHER INFORMATION:/product= "OTHER"
            /note= "O-(TERT-BUTYL)-GLU"

(ix) FEATURE:
        (A) NAME/KEY: Peptide
        (B) LOCATION:4
        (D) OTHER INFORMATION:/product= "OTHER"
            /note= "O-(TERT-BUTYL)-ASP"

(ix) FEATURE:
        (A) NAME/KEY: Peptide
        (B) LOCATION:7
        (D) OTHER INFORMATION:/product= "OTHER"
            /note= "-NH.CH2.CH2.CH2.CH2.COOH"

(xi) SEQUENCE DESCRIPTION: SEQ ID NO: 109:

Xaa Ile Leu Xaa Val Pro Xaa
1               5

(2) INFORMATION FOR SEQ ID NO: 110:

(i) SEQUENCE CHARACTERISTICS:
        (A) LENGTH: 7 amino acids

```
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:1
        (D) OTHER INFORMATION:/product= "OTHER"
            /note= "O-(TERT-BUTYL)-GLU"

(ix) FEATURE:
        (A) NAME/KEY: Peptide
        (B) LOCATION:4
        (D) OTHER INFORMATION:/product= "OTHER"
            /note= "O-(TERT-BUTYL)-ASP"

(ix) FEATURE:
        (A) NAME/KEY: Peptide
        (B) LOCATION:7
        (D) OTHER INFORMATION:/product= "OTHER"
            /note= "-NH.CH2.CH2.CH2.CH2.CH2.COOH"

(xi) SEQUENCE DESCRIPTION: SEQ ID NO: 110:

Xaa Ile Leu Xaa Val Pro Xaa
1               5

(2) INFORMATION FOR SEQ ID NO: 111:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:1
        (D) OTHER INFORMATION:/product= "OTHER"
            /note= "O-(TERT-BUTYL)-GLU"

(ix) FEATURE:
        (A) NAME/KEY: Peptide
        (B) LOCATION:4
        (D) OTHER INFORMATION:/product= "OTHER"
            /note= "O-(TERT-BUTYL)-ASP"

(ix) FEATURE:
        (A) NAME/KEY: Peptide
        (B) LOCATION:7
        (D) OTHER INFORMATION:/product= "OTHER"
            /note= "-NH.CH2.CH2.CH2.CH2.CH2.CH2.CH2.COOH"

(xi) SEQUENCE DESCRIPTION: SEQ ID NO: 111:

Xaa Ile Leu Xaa Val Pro Xaa
1               5

(2) INFORMATION FOR SEQ ID NO: 112:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:1
        (D) OTHER INFORMATION:/product= "MeIle"
```

```
          (ix) FEATURE:
                (A) NAME/KEY: Peptide
                (B) LOCATION:3
                (D) OTHER INFORMATION:/product= "OTHER"
                    /note= "O-(TERT-BUTYL)-ASP"

(ix) FEATURE:
                (A) NAME/KEY: Peptide
                (B) LOCATION:5
                (D) OTHER INFORMATION:/product= "OTHER"
                    /note= "-NH.CH2.CH2.CH2.CH2.COOH"

(xi) SEQUENCE DESCRIPTION: SEQ ID NO: 112:

Ile Leu Xaa Val Xaa
1                 5

(2) INFORMATION FOR SEQ ID NO: 113:

(i) SEQUENCE CHARACTERISTICS:
                (A) LENGTH: 5 amino acids
                (B) TYPE: amino acid
                (C) STRANDEDNESS: single
                (D) TOPOLOGY: linear (ii) MOLECULE TYPE: peptide (ix) FEATURE:
                (A) NAME/KEY: Peptide
                (B) LOCATION:3
                (D) OTHER INFORMATION:/product= "OTHER"
                    /note= "O-(TERT-BUTYL)-ASP"

(ix) FEATURE:
                (A) NAME/KEY: Peptide
                (B) LOCATION:5
                (D) OTHER INFORMATION:/product= "OTHER"
                    /note= "-NH.CH2.CH2.S.CH2.CH2.COOH"

(xi) SEQUENCE DESCRIPTION: SEQ ID NO: 113:

Ile Leu Xaa Val Xaa
1                 5

(2) INFORMATION FOR SEQ ID NO: 114:

(i) SEQUENCE CHARACTERISTICS:
                (A) LENGTH: 5 amino acids
                (B) TYPE: amino acid
                (C) STRANDEDNESS: single
                (D) TOPOLOGY: linear (ii) MOLECULE TYPE: peptide (ix) FEATURE:
                (A) NAME/KEY: Peptide
                (B) LOCATION:3
                (D) OTHER INFORMATION:/product= "OTHER"
                    /note= "O-(TERT-BUTYL)-ASP"

(ix) FEATURE:
                (A) NAME/KEY: Peptide
                (B) LOCATION:5
                (D) OTHER INFORMATION:/product= "OTHER"
                    /note= "-NH.CH2.CH2.CH2.CH2.COOH"

(xi) SEQUENCE DESCRIPTION: SEQ ID NO: 114:

Ile Leu Xaa Leu Xaa
1                 5

(2) INFORMATION FOR SEQ ID NO: 115:

(i) SEQUENCE CHARACTERISTICS:
                (A) LENGTH: 5 amino acids
                (B) TYPE: amino acid
```

```
            (C) STRANDEDNESS: single
            (D) TOPOLOGY: linear (ii) MOLECULE TYPE: peptide (ix) FEATURE:
            (A) NAME/KEY: Peptide
            (B) LOCATION:1
            (D) OTHER INFORMATION:/product= "OTHER"
                /note= "NH2.CH(CO.NH2).CH2.CH2.CO-"

(ix) FEATURE:
            (A) NAME/KEY: Peptide
            (B) LOCATION:4
            (D) OTHER INFORMATION:/product= "OTHER"
                /note= "O-(TERT-BUTYL)-ASP"

(xi) SEQUENCE DESCRIPTION: SEQ ID NO: 115:

Xaa Ile Leu Xaa Val
1               5

(2) INFORMATION FOR SEQ ID NO: 116:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION:3
            (D) OTHER INFORMATION:/product= "OTHER"
                /note= "O-(TERT-BUTYL)-ASP"

(ix) FEATURE:
            (A) NAME/KEY: Peptide
            (B) LOCATION:5
            (D) OTHER INFORMATION:/product= "OTHER"
                /note= "-NH.CH2.CH2.CH2.CH2.COOH"

(xi) SEQUENCE DESCRIPTION: SEQ ID NO: 116:

Ile Leu Xaa Phe Xaa
1               5

(2) INFORMATION FOR SEQ ID NO: 117:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION:1
            (D) OTHER INFORMATION:/product= "bAla"

(ix) FEATURE:
            (A) NAME/KEY: Peptide
            (B) LOCATION:4
            (D) OTHER INFORMATION:/product= "OTHER"
                /note= "O-(TERT-BUTYL)-ASP"

(ix) FEATURE:
            (A) NAME/KEY: Peptide
            (B) LOCATION:6
            (D) OTHER INFORMATION:/product= "OTHER"
                /note= "-NH.CH2.CH2.CH2.CH2.COOH"

(xi) SEQUENCE DESCRIPTION: SEQ ID NO: 117:
```

```
Ala Ile Leu Xaa Val Xaa
1               5
```

(2) INFORMATION FOR SEQ ID NO: 118:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:1
        (D) OTHER INFORMATION:/product= "bAla"

(ix) FEATURE:
        (A) NAME/KEY: Peptide
        (B) LOCATION:3
        (D) OTHER INFORMATION:/product= "MeIle"

(ix) FEATURE:
        (A) NAME/KEY: Peptide
        (B) LOCATION:5
        (D) OTHER INFORMATION:/product= "OTHER"
            /note= "O-(TERT-BUTYL)-ASP"

(xi) SEQUENCE DESCRIPTION: SEQ ID NO: 118:

```
Ala Pro Ile Leu Xaa Val
1               5
```

(2) INFORMATION FOR SEQ ID NO: 119:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:1
        (D) OTHER INFORMATION:/product= "4Abu"

(ix) FEATURE:
        (A) NAME/KEY: Peptide
        (B) LOCATION:4
        (D) OTHER INFORMATION:/product= "OTHER"
            /note= "O-(TERT-BUTYL)-ASP"

(ix) FEATURE:
        (A) NAME/KEY: Peptide
        (B) LOCATION:6
        (D) OTHER INFORMATION:/product= "OTHER"
            /note= "PIPERAZINYL-1-YL-ACETIC ACID"

(xi) SEQUENCE DESCRIPTION: SEQ ID NO: 119:

```
Xaa Ile Leu Xaa Val Xaa
1               5
```

(2) INFORMATION FOR SEQ ID NO: 120:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide

```
    (ix) FEATURE:
         (A) NAME/KEY: Peptide
         (B) LOCATION:1
         (D) OTHER INFORMATION:/product= "OTHER"
             /note= "NH2.CH2.CH2.CH2.CH2.CO-"

(ix) FEATURE:
         (A) NAME/KEY: Peptide
         (B) LOCATION:4
         (D) OTHER INFORMATION:/product= "OTHER"
             /note= "O-(TERT-BUTYL)-ASP"

(ix) FEATURE:
         (A) NAME/KEY: Peptide
         (B) LOCATION:6
         (D) OTHER INFORMATION:/product= "OTHER"
             /note= "PIPERAZINYL-1-YL-ACETIC ACID"

(xi) SEQUENCE DESCRIPTION: SEQ ID NO: 120:

Xaa Ile Leu Xaa Val Xaa
1               5

(2) INFORMATION FOR SEQ ID NO: 121:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
         (A) NAME/KEY: Peptide
         (B) LOCATION:1
         (D) OTHER INFORMATION:/product= "OTHER"
             /note= "NH2.CH2.CH2.CH2.CH2..CH(Z).CO-"

(ix) FEATURE:
         (A) NAME/KEY: Peptide
         (B) LOCATION:4
         (D) OTHER INFORMATION:/product= "OTHER"
             /note= "O-(TERT-BUTYL)-ASP"

(ix) FEATURE:
         (A) NAME/KEY: Peptide
         (B) LOCATION:6
         (D) OTHER INFORMATION:/product= "OTHER"
             /note= "PIPERAZINYL-1-YL-PROPIONIC ACID"

(xi) SEQUENCE DESCRIPTION: SEQ ID NO: 121:

Xaa Ile Leu Xaa Val Xaa
1               5

(2) INFORMATION FOR SEQ ID NO: 122:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
         (A) NAME/KEY: Peptide
         (B) LOCATION:1
         (D) OTHER INFORMATION:/product= "bAla"

(ix) FEATURE:
         (A) NAME/KEY: Peptide
         (B) LOCATION:4
         (D) OTHER INFORMATION:/product= "OTHER"
             /note= "O-(TERT-BUTYL)-ASP"
```

```
(ix) FEATURE:
    (A) NAME/KEY: Peptide
    (B) LOCATION:6
    (D) OTHER INFORMATION:/product= "OTHER"
        /note= "(4-(2-AMINO-ETHYL)-IMIDAZOL-1-YL)-
        ACETIC ACID"

(xi) SEQUENCE DESCRIPTION: SEQ ID NO: 122:

Ala Ile Leu Xaa Val Xaa
1               5
```